US010842872B2

(12) United States Patent
Witham et al.

(10) Patent No.: US 10,842,872 B2
(45) Date of Patent: Nov. 24, 2020

(54) FLUORESCEIN AND BENOXINATE COMPOSITIONS

(71) Applicant: Paragon BioTeck, Inc., Portland, OR (US)

(72) Inventors: Patrick H. Witham, Eugene, OR (US); Sailaja Machiraju, Beaverton, OR (US)

(73) Assignee: PARAGON BIOTECK, INC., Portland, OR (US)

( * ) Notice: Subject to any disclaimer, the term of this patent is extended or adjusted under 35 U.S.C. 154(b) by 0 days.

(21) Appl. No.: 16/820,593

(22) Filed: Mar. 16, 2020

(65) Prior Publication Data

US 2020/0282058 A1 Sep. 10, 2020

Related U.S. Application Data

(63) Continuation of application No. 16/363,985, filed on Mar. 25, 2019, now Pat. No. 10,632,197, which is a continuation of application No. 15/814,186, filed on Nov. 15, 2017, now Pat. No. 10,293,047.

(51) Int. Cl.
| | |
|---|---|
| *A61K 47/10* | (2017.01) |
| *A61K 49/00* | (2006.01) |
| *A61K 31/245* | (2006.01) |
| *A61B 3/16* | (2006.01) |
| *A61K 9/08* | (2006.01) |
| *A61K 9/00* | (2006.01) |
| *A61K 47/02* | (2006.01) |
| *A61K 47/32* | (2006.01) |

(52) U.S. Cl.
CPC ............ *A61K 47/10* (2013.01); *A61B 3/16* (2013.01); *A61K 9/0048* (2013.01); *A61K 9/08* (2013.01); *A61K 31/245* (2013.01); *A61K 47/02* (2013.01); *A61K 47/32* (2013.01); *A61K 49/0004* (2013.01); *A61K 49/006* (2013.01); *A61K 49/0043* (2013.01)

(58) Field of Classification Search
CPC ...... A61K 47/10; A61K 31/245; A61K 47/02; A61K 49/006; A61K 9/0048; A61K 49/0043; A61K 47/32; A61K 9/08; A61K 49/0004; A61B 3/16
See application file for complete search history.

(56) References Cited

U.S. PATENT DOCUMENTS

| | | | |
|---|---|---|---|
| 3,306,820 | A | 2/1967 | Krezanoski et al. |
| 6,218,428 | B1 | 4/2001 | Chynn et al. |
| 7,982,056 | B2 | 7/2011 | Bydlinski et al. |
| 10,293,047 | B1 | 5/2019 | Witham et al. |
| 2018/0036328 | A1 | 2/2018 | Tsubota et al. |

FOREIGN PATENT DOCUMENTS

| | | |
|---|---|---|
| JP | 2009196988 A | 9/2009 |
| WO | 2016196367 A1 | 12/2016 |

OTHER PUBLICATIONS

Bausch & Lomb, product sheet for Fluorescein Sodium and Benoxinate Hydrochloride solution/drops, product marketed as of Jan. 1, 1995 (5 pgs).
PCT/US2018/061379 International Search Report and Written Opinion dated Mar. 8, 2019, 9 pages.
U.S. Appl. No. 15/814,186 Office Action dated Mar. 22, 2018, 7 pages.

*Primary Examiner* — Robert S Cabral
(74) *Attorney, Agent, or Firm* — Procopio, Cory, Hargreaves & Savitch LLP; Xiaofan Yang

(57) ABSTRACT

Compositions comprising a fluorescein component and benoxinate component and the corresponding uses of these compositions are described herein. These compositions have improved storage life and the fluorescein component and/or benoxinate component minimally degrade after 12 to 18 months of storage.

23 Claims, 15 Drawing Sheets

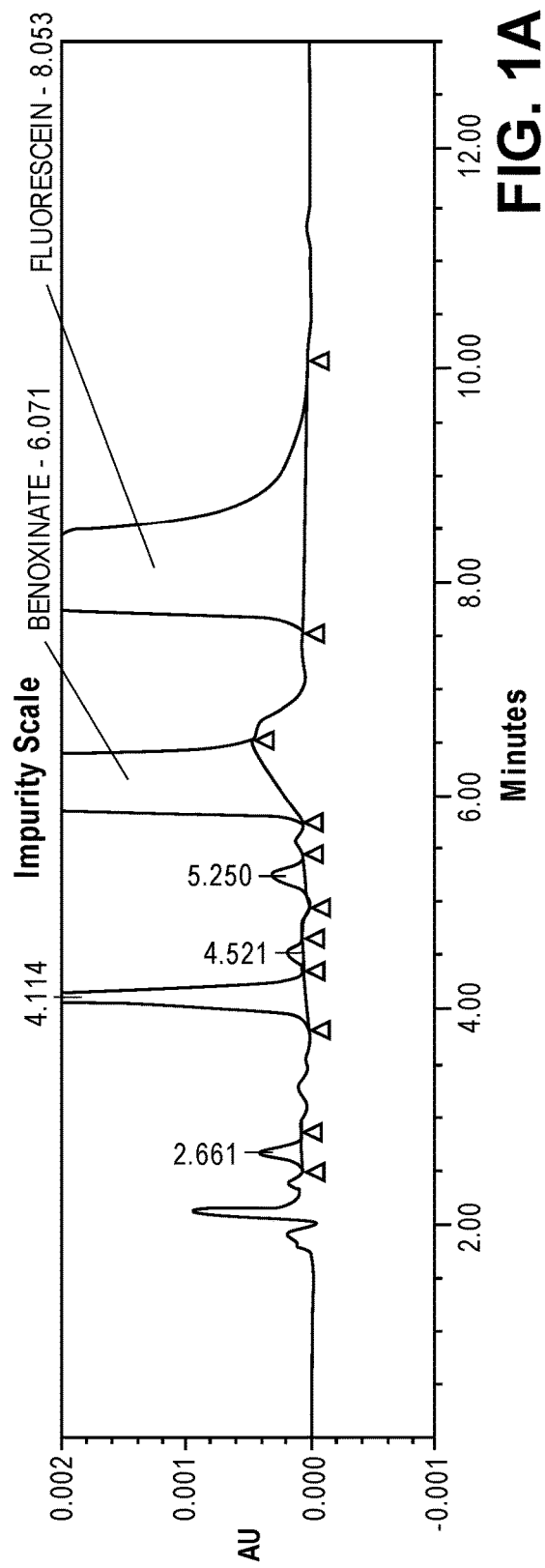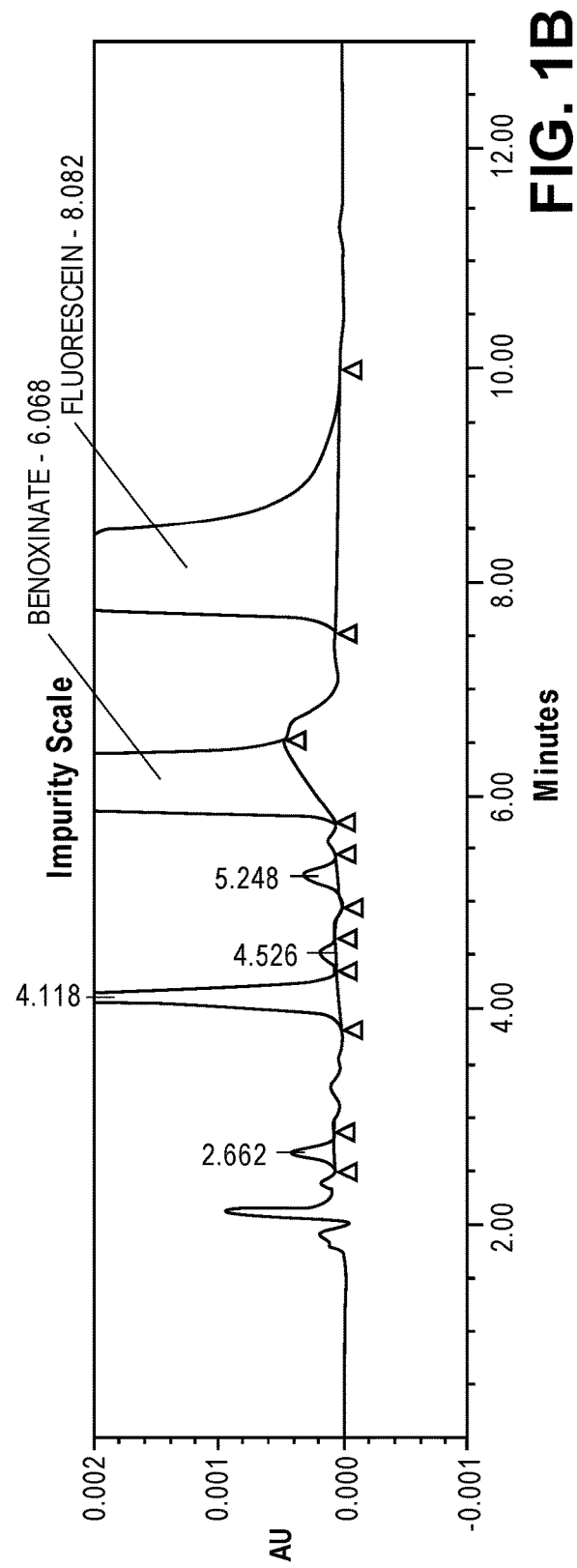

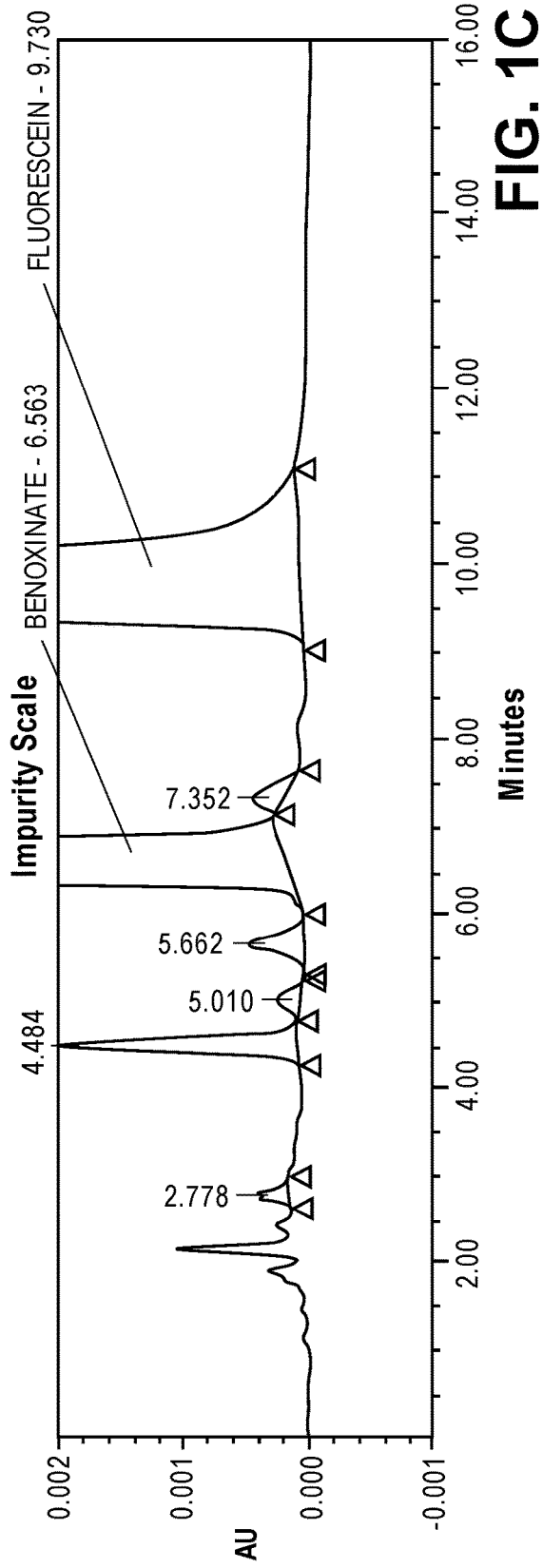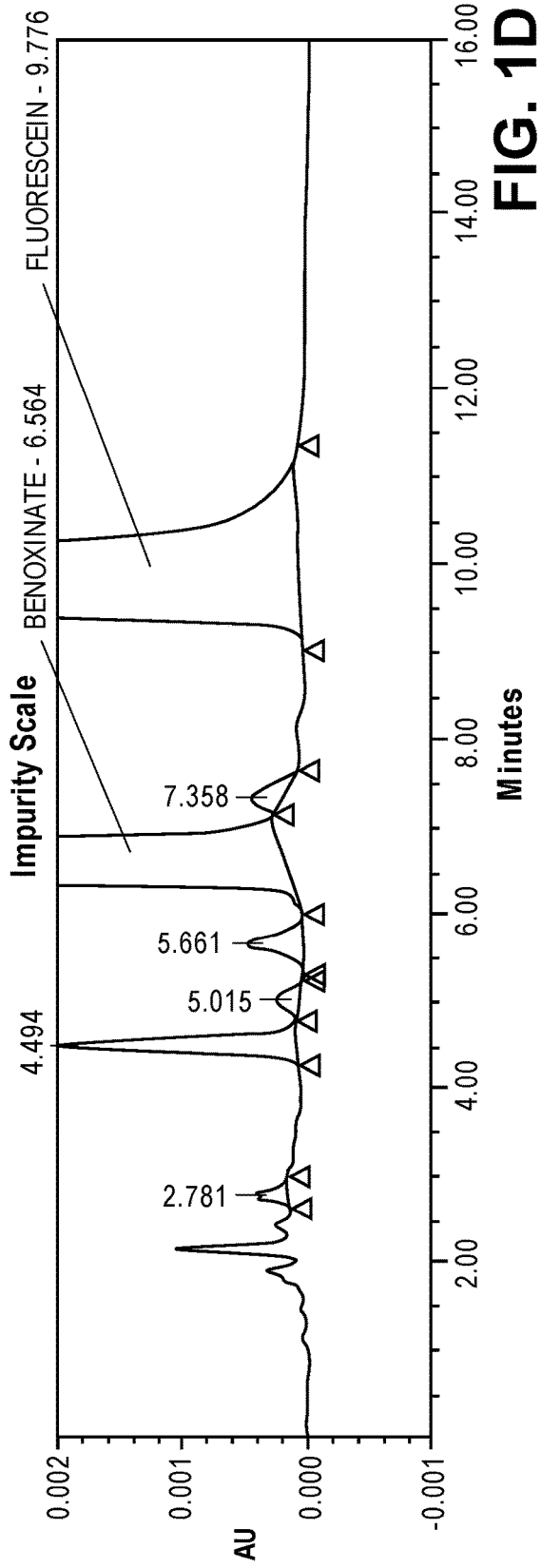

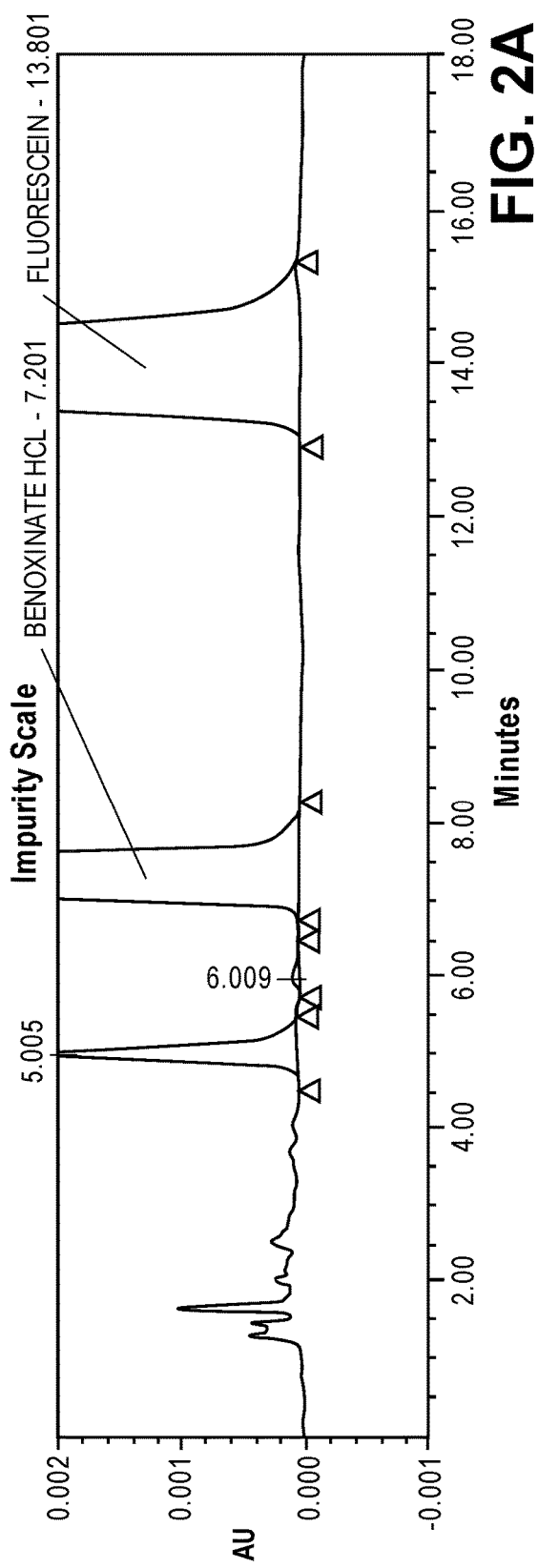
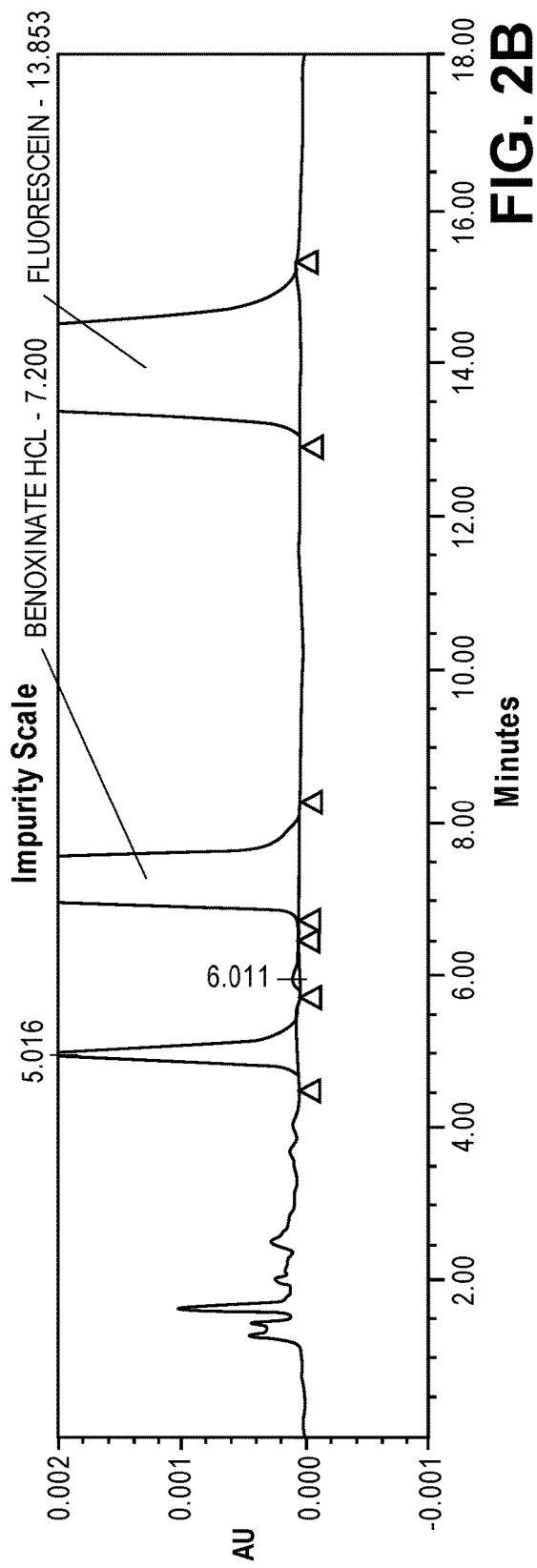

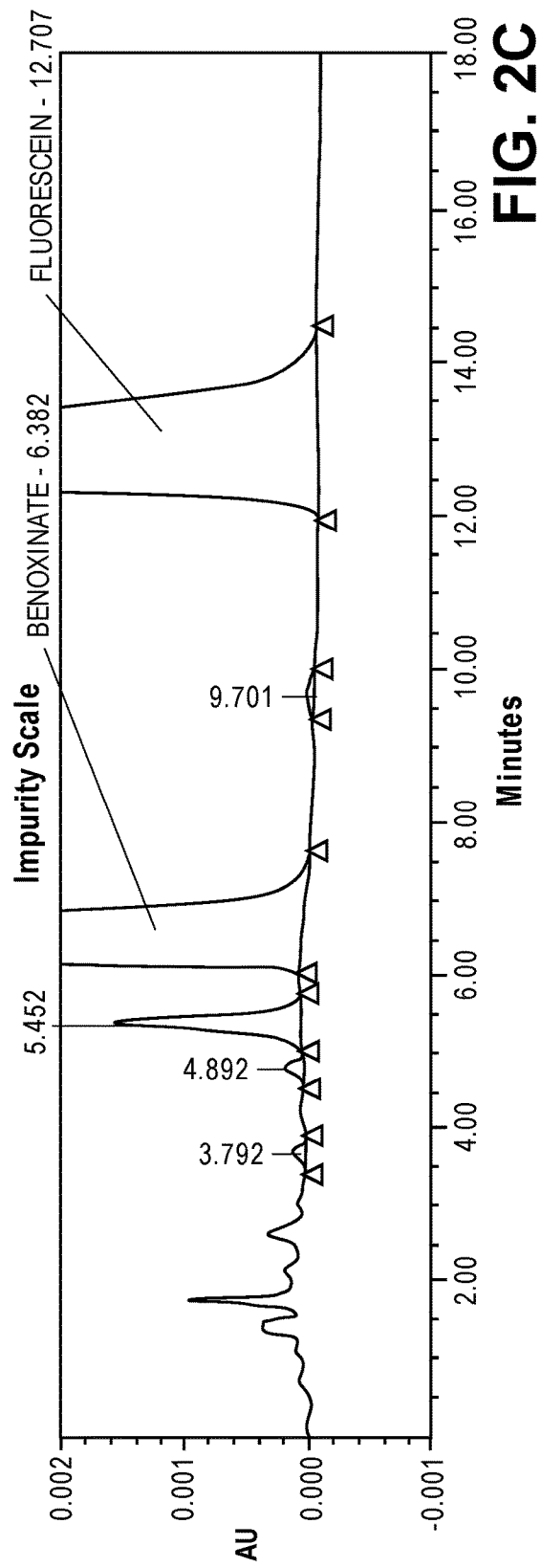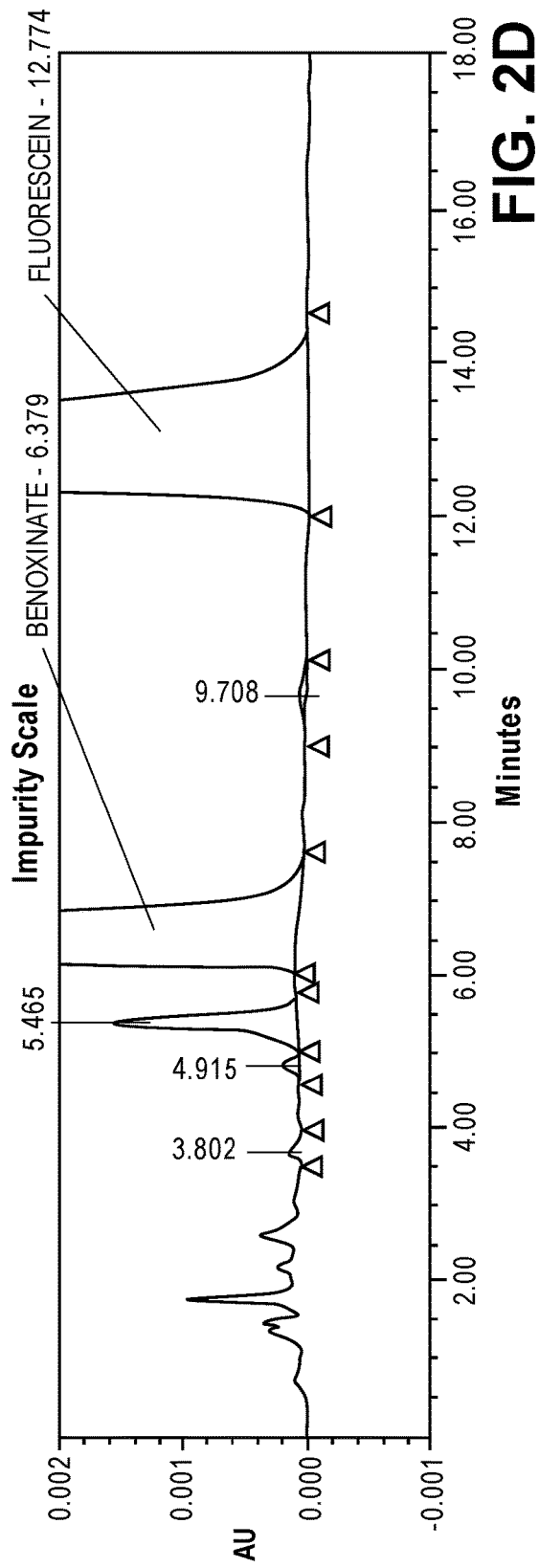

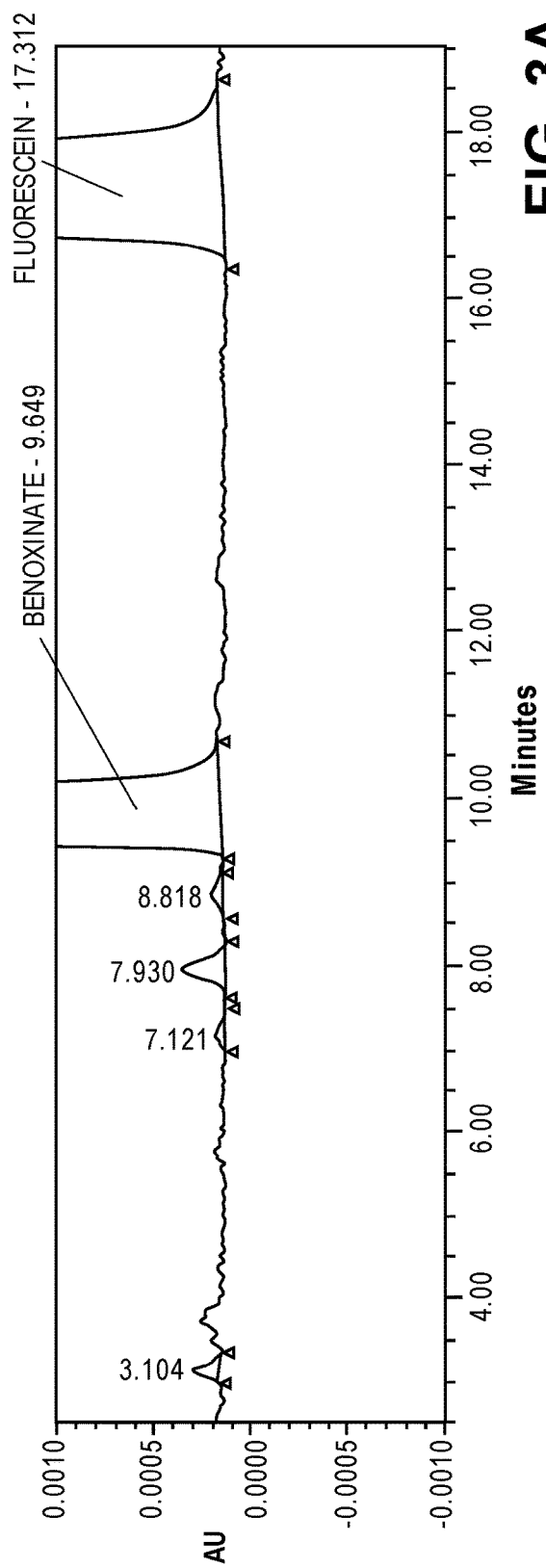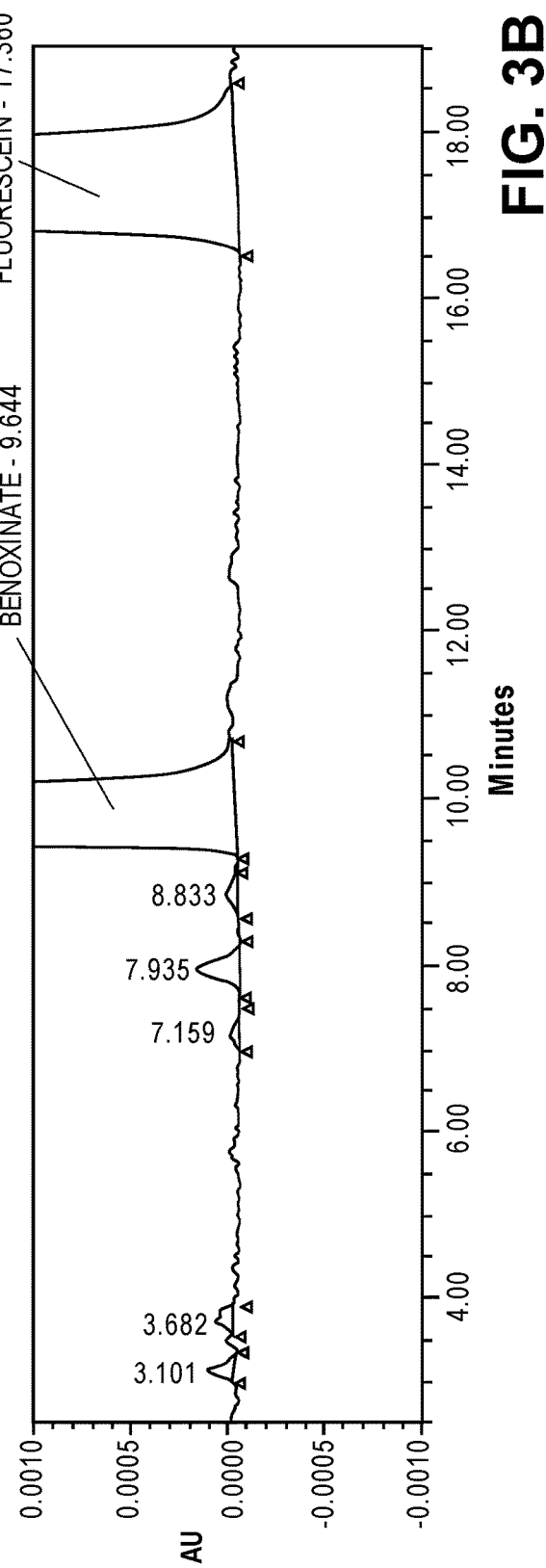

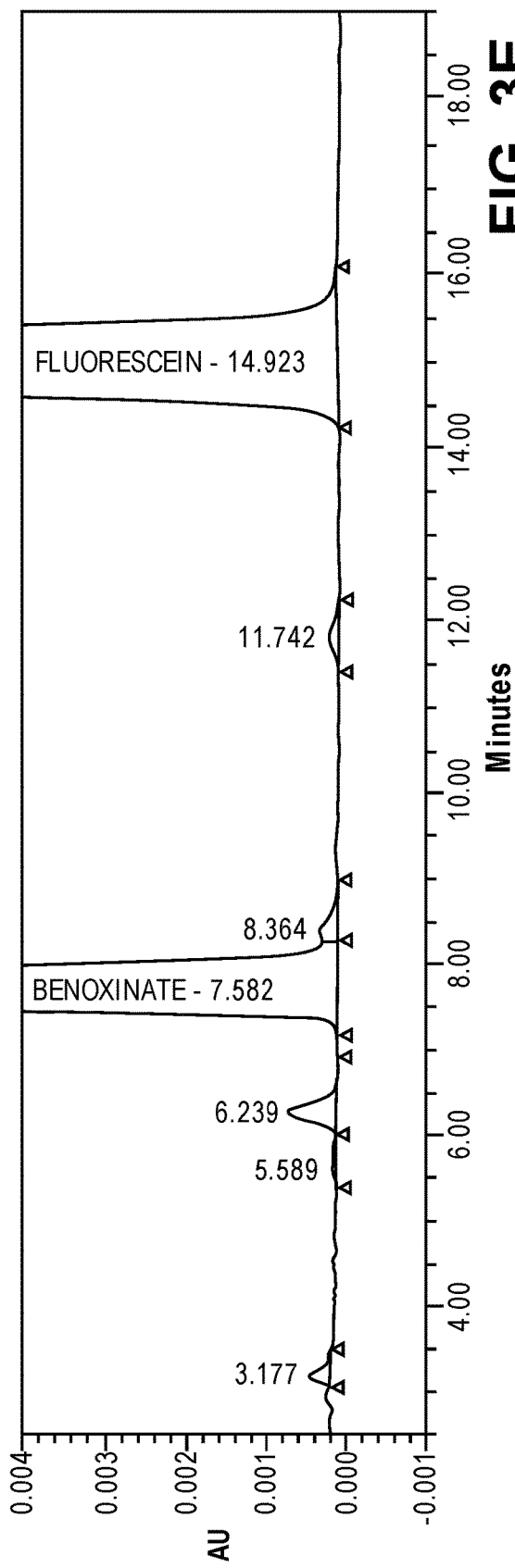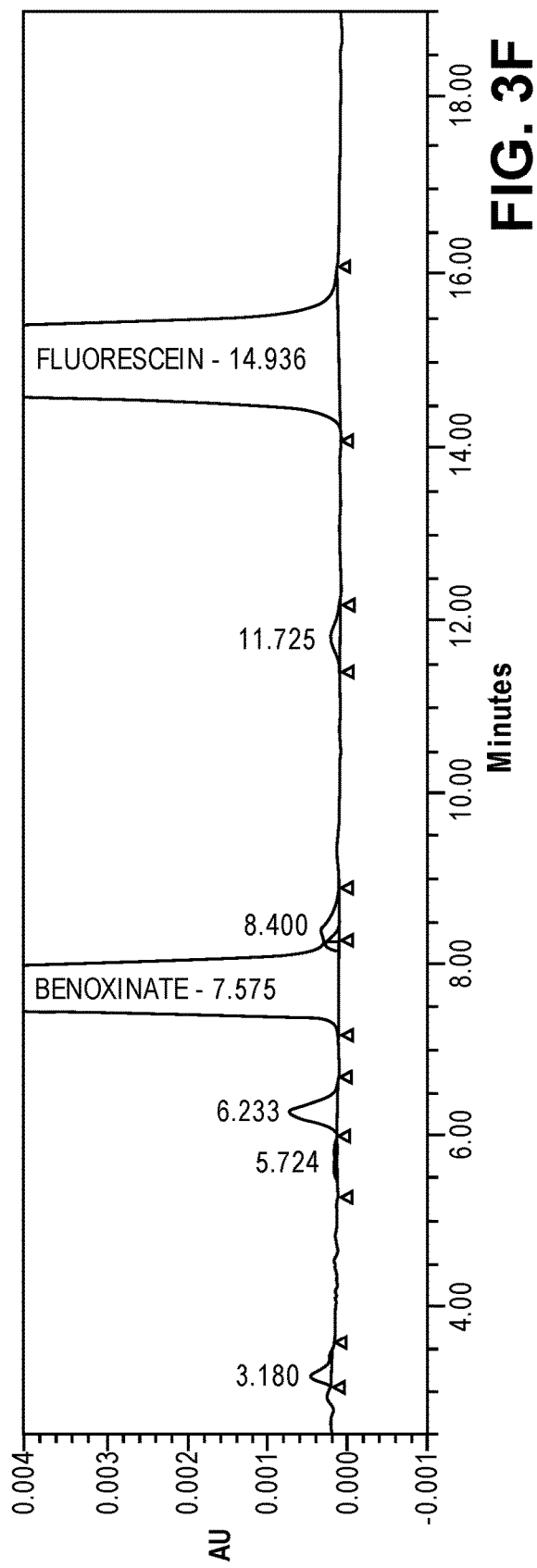

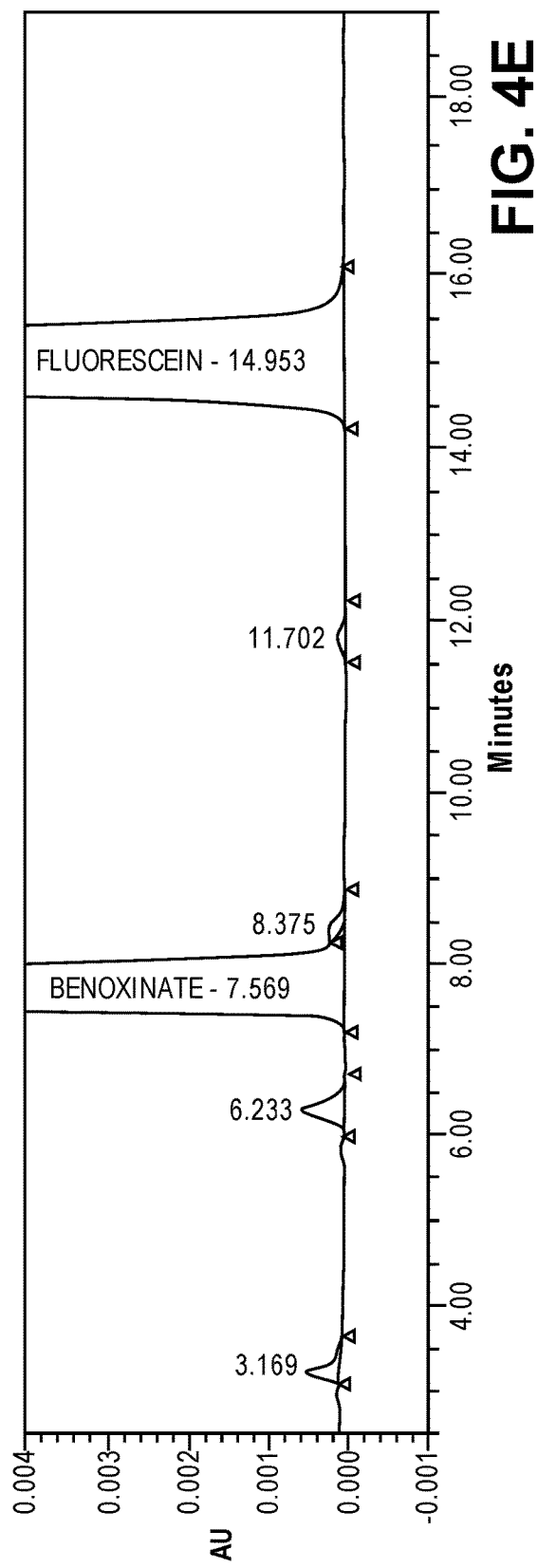
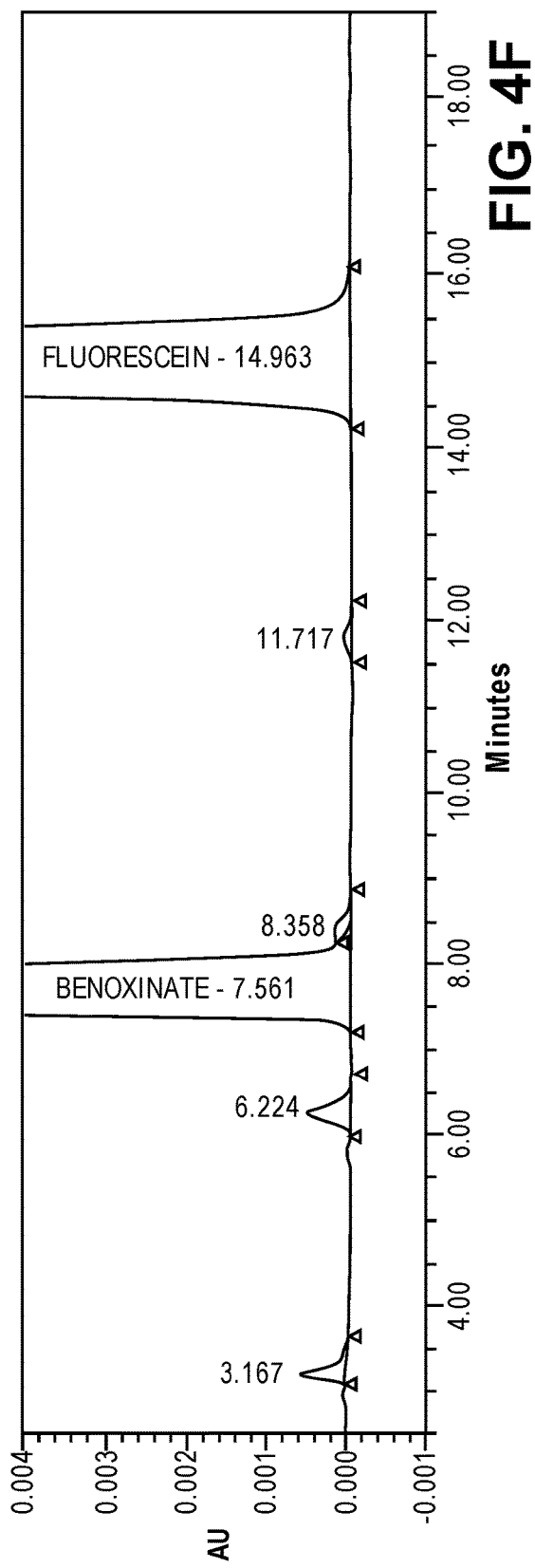

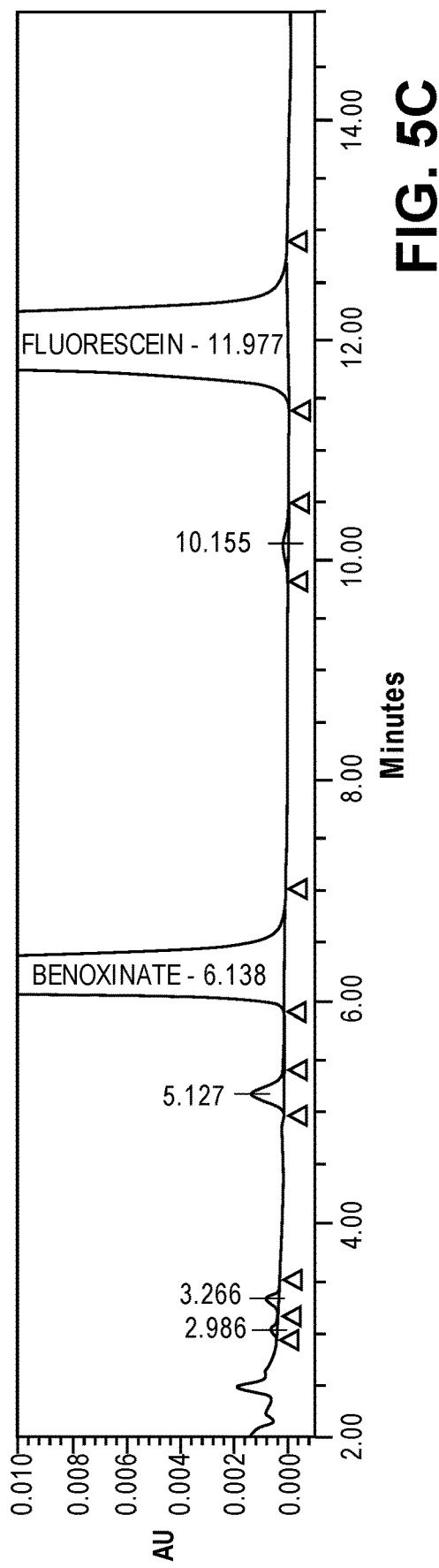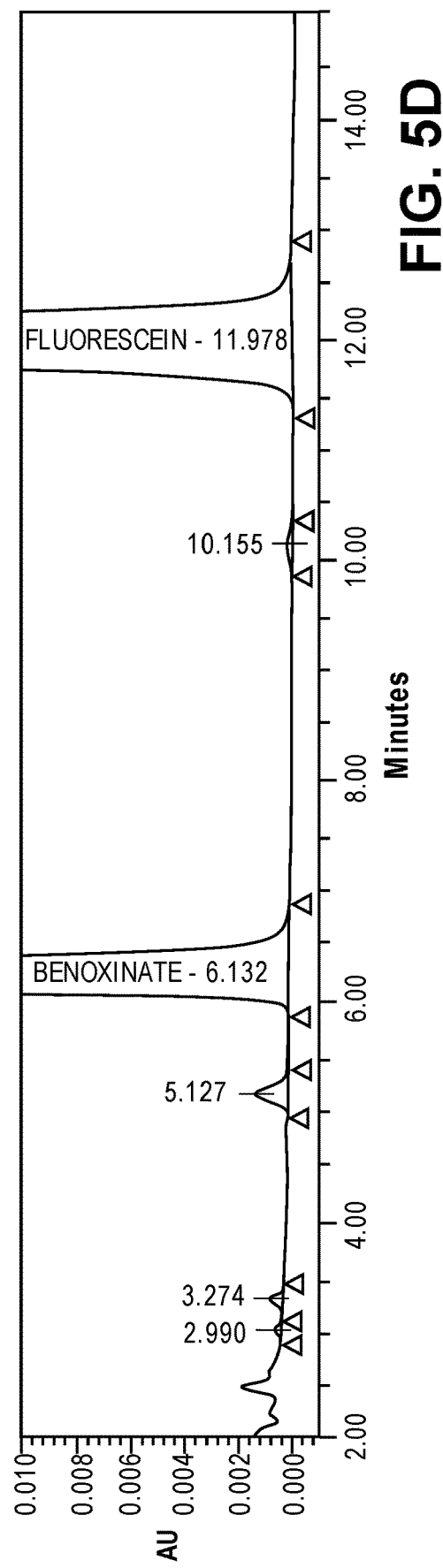

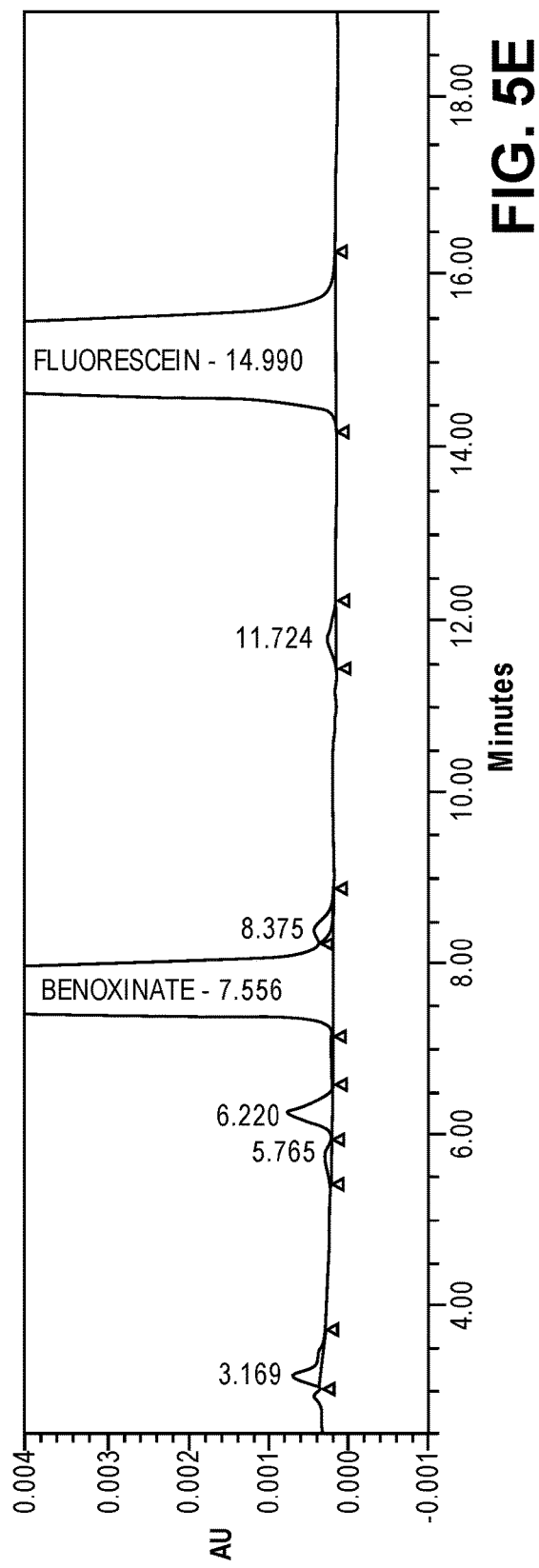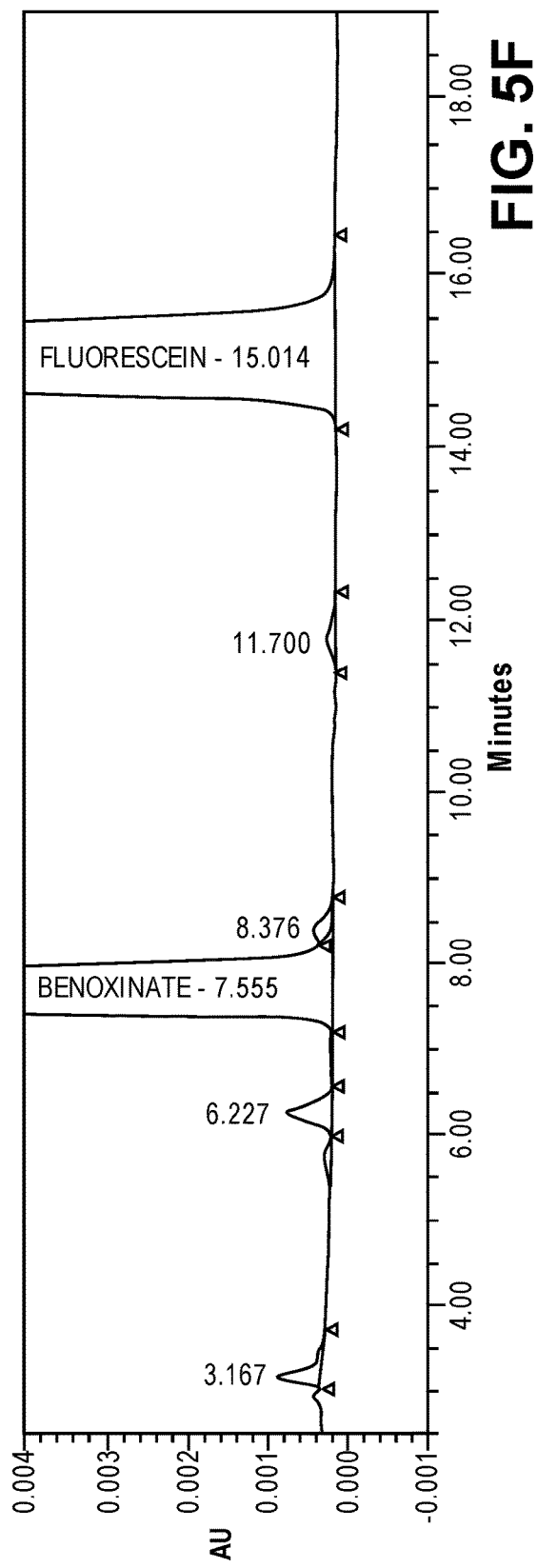

FLUORESCEIN AND BENOXINATE COMPOSITIONS

CROSS REFERENCE TO RELATED APPLICATIONS

This application is a continuation of U.S. application Ser. No. 16/363,985, filed Mar. 25, 2019, which is a continuation of U.S. application Ser. No. 15/814,186, filed Nov. 15, 2017, now U.S. Pat. No. 10,293,047, issued May 21, 2019. The disclosure of each of the prior applications is considered part of, and is incorporated by reference in, the disclosure of this application.

BACKGROUND OF THE DISCLOSURE

Fluorescein, such as fluorescein sodium, is a dye that is widely used as a diagnostic tool in the field of ophthalmology and optometry, and benoxinate, such as benoxinate hydrochloride, is local anesthetic that is also used in ophthalmology. The combination of fluorescein and benoxinate, such as fluorescein sodium and benoxinate hydrochloride, is used in various applications related to the eye, such as tonometry, gonioscopy, removal of corneal foreign bodies and other short corneal or conjunctival procedures.

SUMMARY OF THE DISCLOSURE

Provided in one aspect is a composition comprising: a) a fluorescein component; and b) a benoxinate component; wherein the composition comprises a total impurity of about 1.5% or less by weight, and wherein the total impurity comprises one or more impurities with relative retention times from about 0.10 to about 1.90 under HPLC Method A.

In some embodiments, the total impurity is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 0 months, 12 months, or 18 months of storage. In some embodiments, the total impurity is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 0 months, 12 months, or 18 months of storage.

In some embodiments, the total impurity comprises an impurity with a relative retention time of about 0.43. In some embodiments, the impurity with a relative retention time of about 0.43 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 0 months, 12 months, or 18 months of storage. In some embodiments, the impurity with a relative retention time of about 0.43 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 0 months, 12 months, or 18 months of storage.

In some embodiments, the total impurity comprises an impurity with a relative retention time of about 0.68. In some embodiments, the impurity with a relative retention time of about 0.68 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 0 months, 12 months, or 18 months of storage. In some embodiments, the impurity with a relative retention time of about 0.68 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 0 months, 12 months, or 18 months of storage.

In some embodiments, the total impurity comprises an impurity with a relative retention time of about 0.74. In some embodiments, the impurity with a relative retention time of about 0.74 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 0 months, 12 months, or 18 months of storage. In some embodiments, the impurity with a relative retention time of about 0.74 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 0 months, 12 months, or 18 months of storage.

In some embodiments, the total impurity comprises an impurity with a relative retention time of about 0.79. In some embodiments, the impurity with a relative retention time of about 0.79 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 0 months, 12 months, or 18 months of storage. In some embodiments, the impurity with a relative retention time of about 0.79 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 0 months, 12 months, or 18 months of storage.

In some embodiments, the composition comprises at least about 90% of the benoxinate component that has not degraded after 12 months or 18 months of storage. In some embodiments, the composition comprises at least about 97% of the fluorescein component that has not degraded after 12 months or 18 months of storage.

In some embodiments, the composition comprises about 0.25% by weight of the fluorescein component. In some embodiments, the fluorescein component comprises fluorescein or the pharmaceutically acceptable salt thereof. In some embodiments, the pharmaceutically acceptable salt of fluorescein is the sodium salt.

In some embodiments, the composition comprises about 0.40% by weight of the benoxinate component. In some embodiments, the benoxinate component comprises benoxinate or the pharmaceutically acceptable salt thereof. In some embodiments, the pharmaceutically acceptable salt of benoxinate is the hydrochloride salt.

In some embodiments, the composition further comprises one or more inactive agents selected from boric acid, povidone, purified water, and hydrochloric acid. In some embodiments, the composition further comprises a preservative. In some embodiments, the preservative is a preservative suitable for ophthalmic use. In some embodiments, the preservative is chlorobutanol. In some embodiments, the preservative is chlorobutanol or any other suitable ophthalmic preservative. In some embodiments, the composition is suitable for ophthalmic use.

Also provided herein is a method for removing foreign bodies and sutures in a subject in need thereof comprising administering a therapeutically effective amount of any one of the compositions described herein.

Also provided herein is a method for conducting an ocular examination in a subject in need thereof comprising: administering a therapeutically effective amount of any one of the compositions described herein. In some embodiments, the method further comprises measuring the intraocular pressure of the eye.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A shows an overlay HPLC chromatogram of Formulation 7, Run 1 after 12 months of storage. FIG. 1B shows an overlay HPLC chromatogram of Formulation 7, Run 2 after 12 months of storage. FIG. 1C shows an overlay HPLC chromatogram of Formulation 7, Run 1 after 18 months of storage. FIG. 1D shows an overlay HPLC chromatogram of Formulation 7, Run 2, after 18 months of storage.

FIG. 2A shows an overlay HPLC chromatogram of Formulation 8, Run 1 after 0 months of storage. FIG. 2B shows an overlay HPLC chromatogram of Formulation 8, Run 2 after 0 months of storage. FIG. 2C shows an overlay HPLC chromatogram of Formulation 8, Run 1 after 12 months of storage. FIG. 2D shows an overlay HPLC chromatogram of Formulation 8, Run 2, after 12 months of storage.

FIG. 3A shows an overlay HPLC chromatogram of Formulation 9, Run 1 after 0 months of storage. FIG. 3B shows an overlay HPLC chromatogram of Formulation 9, Run 2 after 0 months of storage. FIG. 3E shows an overlay HPLC chromatogram of Formulation 9, Run 1 after 18 months of storage. FIG. 3F shows an overlay HPLC chromatogram of Formulation 9, Run 2, after 18 months of storage.

FIG. 4E shows an overlay HPLC chromatogram of Formulation 10, Run 1 after 18 months of storage. FIG. 4F shows an overlay HPLC chromatogram of Formulation 10, Run 2, after 18 months of storage.

FIG. 5C shows an overlay HPLC chromatogram of Formulation 11, Run 1 after 12 months of storage. FIG. 5D shows an overlay HPLC chromatogram of Formulation 11, Run 2, after 12 months of storage. FIG. 5E shows an overlay HPLC chromatogram of Formulation 11, Run 1 after 18 months of storage. FIG. 5F shows an overlay HPLC chromatogram of Formulation 11, Run 2, after 18 months of storage.

DETAILED DESCRIPTION OF THE DISCLOSURE

Figure 2E:
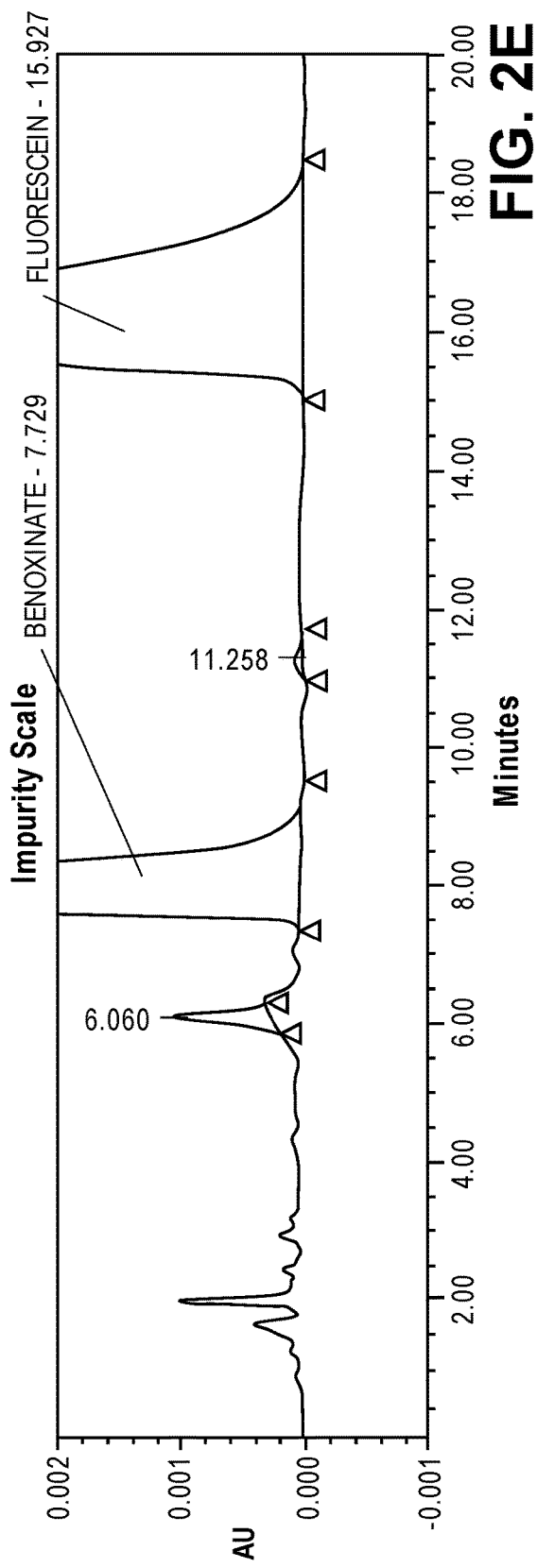
FIG. 2E shows an overlay HPLC chromatogram of Formulation 8, Run 1 after 18 months of storage.

Provided herein are compositions comprising fluorescein and benoxinate that have improved storage life and have minimal impurities after storage. In some embodiments, the benoxinate component and/or the fluorescein component of the compositions described herein minimally degrade after storage (i.e., after 12 months and/or 18 months of storage at about 2° C. to about 8° C.).

Fluorescein

Fluorescein is a disclosing agent. Fluorescein sodium is the sodium salt of fluorescein and has a molecular formula of $C_{20}H_{10}Na_2O_5$, molecular weight of 376.28, and the following chemical structure:

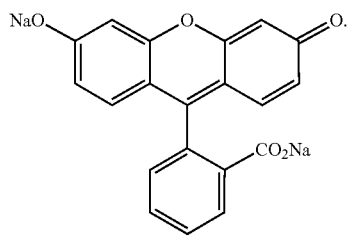

The chemical name for fluorescein sodium is spiro [isobenzofuran-1(3H), 9'-[9H]xanthene]-3-one, 3'6'-dihydroxy, disodium salt.

In some embodiments, the fluorescein component of the compositions described herein is fluorescein or the pharmaceutically acceptable salt thereof. In some embodiments, the pharmaceutically acceptable salt of fluorescein is the sodium salt.

Benoxinate

Benoxinate, also known as oxybuprocaine or BNX, is a local anesthetic. Benoxinate hydrochloride is the HCl salt of benoxinate and has a molecular formula of $C_{17}H_{28}N_2O_3 \cdot HCl$, a molecular weight of 344.88, and the following chemical structure:

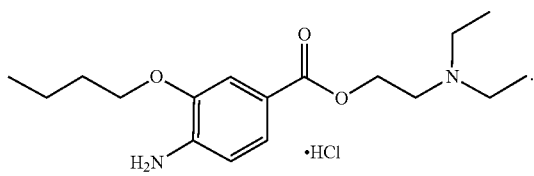 [SMILES: CCCCOc1cc(C(=O)OCCN(CC)CC)ccc1N ; Cl]

Synonyms for benoxinate hydrochloride include but are not limited to 2-(diethylamino)ethyl 4-amino-3-butoxybenzoate hydrochloride, 4-amino-3-butoxybenzoic acid diethylaminoethyl ester, and oxybuprocaine hydrochloride.

In some embodiments, the benoxinate component of the compositions described herein is benoxinate or the pharmaceutically acceptable salt thereof. In some embodiments, the pharmaceutically acceptable salt of benoxinate is the hydrochloride salt.

Compositions

In some embodiments, the compositions described herein comprise a fluorescein component and benoxinate component.

In some embodiments, the composition comprises about 0.25% by weight of the fluorescein component. In some embodiments, the composition comprises from about 0.20% to about 0.30% by weight of the fluorescein component. In some embodiments, the composition comprises from about 0.22% to about 0.28% by weight of the fluorescein component. In some embodiments, the composition comprises from about 0.23% to about 0.27% by weight of the fluorescein component. In some embodiments, the composition comprises about 0.20%, about 0.21%, about 0.22%, about 0.23%, about 0.24%, about 0.25%, about 0.26%, about 0.27%, about 0.28%, about 0.29%, or about 0.30% by weight of the fluorescein component. In some embodiments, the composition comprises about 0.20% by weight of the fluorescein component. In some embodiments, the composition comprises about 0.21% by weight of the fluorescein component. In some embodiments, the composition comprises about 0.22% by weight of the fluorescein component. In some embodiments, the composition comprises about 0.23% by weight of the fluorescein component. In some embodiments, the composition comprises about 0.24% by weight of the fluorescein component. In some embodiments, the composition comprises about 0.25% by weight of the fluorescein component. In some embodiments, the composition comprises about 0.26% by weight of the fluorescein component. In some embodiments, the composition comprises about 0.27% by weight of the fluorescein component. In some embodiments, the composition comprises about 0.28% by weight of the fluorescein component. In some embodiments, the composition comprises about 0.29% by weight of the fluorescein component. In some embodiments, the composition comprises about 0.30% by weight of the fluorescein component.

In some embodiments, the composition comprises an overage of the fluorescein component. In some embodiments, the overage of the fluorescein component is about 1%. In some embodiments, the overage of the fluorescein component is about 5%. In some embodiments, the overage of the fluorescein component is about 10%. In some embodiments, the overage of the fluorescein component is about 15%. In some embodiments, the overage of the fluorescein component is about 20%. In some embodiments, the overage of the fluorescein component is about 25%. In some embodiments, the overage of the fluorescein component is about 30%.

In some embodiments, the composition comprises about 0.40% by weight of the benoxinate component. In some embodiments, the composition comprises from about 0.32% to about 0.48% by weight of the benoxinate component. In some embodiments, the composition comprises from about 0.36% to about 0.44% by weight of the benoxinate component. In some embodiments, the composition comprises about 0.32%, about 0.33%, about 0.34%, about 0.35%, about 0.36%, about 0.37%, about 0.38%, about 0.39%, about 0.40%, about 0.41%, about 0.42%, about 0.43%, about 0.44%, about 0.45%, about 0.46%, about 0.47%, or about 0.48% by weight of the benoxinate component. In some embodiments, the composition comprises about 0.32% by weight of the benoxinate component. In some embodiments, the composition comprises about 0.33% by weight of the benoxinate component. In some embodiments, the composition comprises about 0.34% by weight of the benoxinate component. In some embodiments, the composition comprises about 0.35% by weight of the benoxinate component. In some embodiments, the composition comprises about 0.36% by weight of the benoxinate component. In some embodiments, the composition comprises about 0.37% by weight of the benoxinate component. In some embodiments, the composition comprises about 0.38% by weight of the benoxinate component. In some embodiments, the composition comprises about 0.39% by weight of the benoxinate component. In some embodiments, the composition comprises about 0.40% by weight of the benoxinate component. In some embodiments, the composition comprises about 0.41% by weight of the benoxinate component. In some embodiments, the composition comprises about 0.42% by weight of the benoxinate component. In some embodiments, the composition comprises about 0.43% by weight of the benoxinate component. In some embodiments, the composition comprises about 0.44% by weight of the benoxinate component. In some embodiments, the composition comprises about 0.45% by weight of the benoxinate component. In some embodiments, the composition comprises about 0.46% by weight of the benoxinate component. In some embodiments, the composition comprises about 0.47% by weight of the benoxinate component. In some embodiments, the composition comprises about 0.48% by weight of the benoxinate component.

In some embodiments, the composition comprises an overage of the benoxinate component. In some embodiments, the overage of the benoxinate component is about 1%. In some embodiments, the overage of the benoxinate component is about 5%. In some embodiments, the overage of the benoxinate component is about 10%. In some embodiments, the overage of the benoxinate component is about 15%. In some embodiments, the overage of the benoxinate component is about 20%. In some embodiments, the overage of the benoxinate component is about 25%. In some embodiments, the overage of the benoxinate component is about 30%.

In some embodiments, the composition has a pH of about 4.0 to about 6.0. In some embodiments, the composition has a pH of about 4.0 to about 5.5. In some embodiments, the composition has a pH of about 4.3 to about 5.3. In some embodiments, the composition has a pH of about 4.0. In some embodiments, the composition has a pH of about 4.1. In some embodiments, the composition has a pH of about 4.2. In some embodiments, the composition has a pH of about 4.3. In some embodiments, the composition has a pH of about 4.4. In some embodiments, the composition has a pH of about 4.5. In some embodiments, the composition has a pH of about 4.6. In some embodiments, the composition has a pH of about 4.7. In some embodiments, the composition has a pH of about 4.8. In some embodiments, the composition has a pH of about 4.9. In some embodiments, the composition has a pH of about 5.0. In some embodiments, the composition has a pH of about 5.1. In some embodiments, the composition has a pH of about 5.2. In some embodiments, the composition has a pH of about 5.3. In some embodiments, the composition has a pH of about 5.4. In some embodiments, the composition has a pH of about 5.5. In some embodiments, the composition has a pH of about 5.6. In some embodiments, the composition has a pH of about 5.7. In some embodiments, the composition has a pH of about 5.8. In some embodiments, the composition has a pH of about 5.9. In some embodiments, the composition has a pH of about 6.0.

In some embodiments, the composition further comprises one or more inactive agents. In some embodiments, the inactive agents are boric acid, povidone, purified water, hydrochloric acid, and/or sodium hydroxide. In some embodiments, the inactive agents are boric acid, povidone, purified water, and/or hydrochloric acid. In some embodiments, the inactive agent is boric acid. In some embodiments, the inactive agent is povidone. In some embodiments, the inactive agent is purified water. In some embodiments, the inactive agent is used to adjust the pH of the composition. In some embodiments, the inactive agent is hydrochloric acid. In some embodiments, the inactive agent is sodium hydroxide.

In some embodiments, the composition further comprises a preservative. In some embodiments, the preservative is a preservative suitable for ophthalmic use. In some embodiments, the preservative is chlorobutanol or any other suitable ophthalmic preservative. In some embodiments, the preservative is chlorobutanol.

In some embodiments, the composition further comprises a viscosity agent. In some embodiments, the viscosity agent is povidone. In some embodiments, the composition further comprises a buffering agent. In some embodiments, the buffering agent is boric acid. In some embodiments, the composition further comprises a diluent. In some embodiments, the diluent is purified water.

Impurity Profiles

HPLC Method A is used herein to evaluate and quantify the impurities of any one of the compositions described herein. The objective of the HPLC Method A is to provide an analytical HPLC procedure for the identification and quantitative determination of fluorescein (such as fluorescein sodium) and benoxinate (such as benoxinate HCl), to determine chromatographic impurities in a composition comprising fluorescein and benoxinate (including the pharmaceutically acceptable salts thereof), such as any one of the compositions described herein, and/or to determine compounding the potency factor of the drug substance.

The range of the assay method is about 80%-about 120%. The range of the assay method is not less than about 80%. The range of the assay method is not more than about 120%. The range of the related substance method is 0.1% to 2.0% of the working concentration.

Materials

The materials used for HPLC Method A are the following items:
    HPLC solvent pumping system
    UV absorbance detector
    Autosampler
    Waterbath
    HPLC C18 Column.
    Reagent grade Sodium 1-pentanesulfonate
    Glacial acetic acid
    Reagent grade triethanolamine
    HPLC grade phosphoric acid
    HPLC grade water
    Acetonitrile
    Volumetric flasks: 25, 100, and 2000 mL
    Volumetric pipettes: 1 and 10 mL TC
    Volumetric pipettes: 0.5, 2.5, and 10 mL TD
    Diacetylfluorescein reference standard
    Benoxinate HCl reference standard
    2.5N NaOH
    Reagent alcohol
    Analytical balance
    pH meter Preparation of Solutions, Standards and Samples Mobile Phase The aqueous and organic phase solutions are carefully measured. The pH should be from about 3.0 to about 4.0.

100 mg of sodium 1-pentanesulfonate is dissolved in 40 mL of glacial acetic acid in a 2000 mL volumetric flask. 600 mL of acetonitrile and 10 mL of triethanolamine are added. Water is then used to dilute to volume. pH is adjusted with phosphoric acid. The solution is then filtered and degassed by vacuum filtration through a nylon membrane filter with finer porosity.

Fluorescein Stock Standard Solution 27.5 mg of diacetylfluorescein Reference Standard is accurately weighed into a 25 mL volumetric flask. 2.5 mL of reagent alcohol and 0.5 mL of a NaOH solution with an appropriate concentration are added. The solution is then heated in a waterbath set to 65° C. with frequent swirling for 10 minutes or until dissolved. The solution is then cooled to room temperature and diluted to volume with water.

Working Standard Solution

The benoxinate HCl Reference Standard is quantitatively dissolved in the fluorescein stock standard solution with a 10 mL TC pipette into a 100 mL volumetric flask. The pipette is then rinsed several times with mobile phase into the flask. The solution is then diluted to volume with mobile phase and mixed. The resulting solution contains approximately 0.099 mg/mL fluorescein sodium and 0.16 mg/mL of benoxinate HCl. The working standard solutions are stable for 7 days at refrigerated conditions (5±3° C.).

Sample Preparation

The time between sample preparation and sample analysis is minimized. An appropriate amount of sample solution is transferred into a 25 mL volumetric flask to obtain a similar concentration as that of the working standard solution. The sample solution is diluted to volume with mobile phase and then mixed.

Drug Substance Preparation

An appropriate amount of drug substance is transferred into a 25 mL volumetric flask. The solution is then diluted to volume with water and mixed to provide the stock sample preparation. An appropriate amount of the stock sample preparation is transferred with a T. C. type pipette. The pipette is rinsed several times into a 50 mL volumetric flask and the solution is diluted with mobile phase.

Chromatographic Conditions

The following chromatographic conditions are used: Flow rate: approximately 1.5 mL/min. Detector Wavelength: 254 nm; Injection Volume: 25 µL; Column temperature: ambient. Run time is adjusted accordingly to allow for better peak separation.

System Suitability

The relative standard deviation (RSD) is not more than 2.0% for six replicate injections of the standard solution. The tailing factor is as follows: NMT 2.0 for fluorescein sodium peak and benoxinate HCl peak.

Test Procedure

The HPLC system is equilibrated with mobile phase for at least 30 minutes and 2-4 standard preparations are injected to stabilize the column. The chromatograms are discarded. The diluent is then injected. To establish system suitability, six replicate 25 µL injections of the working standard solution are made. The RSD is no greater than 2.0%. The standard and samples are injected in duplicate. Every three sample injections are bracketed with standard injections.

In some embodiments, the % of impurity, including total impurity or a specific impurity, as determined by HPLC Method A is for weight/weight and weight/volume. In other words, it is the % of all the actives and excipients.

Provided herein in one aspect is a composition comprising: a) a fluorescein component; and b) benoxinate component; the composition comprises a total impurity of about 1.5% or less by weight, and wherein the total impurity comprises one or more impurities with relative retention times from about 0.10 to about 1.90 under HPLC Method A.

In some embodiments, the composition comprises a total impurity of about 1.5% or less, about 1.4% or less, about 1.3% or less, about 1.2% or less, about 1.1% or less, about 1.0% or less, about 0.9% or less, about 0.8% or less, about 0.7% or less, about 0.6% or less, about 0.5% or less, about 0.4% or less, about 0.3% or less, about 0.2% or less, about 0.1% or less, about 0.09% or less, about 0.08% or less, about 0.07% or less, about 0.06% or less, about 0.05% or less, about 0.04% or less, about 0.03% or less, about 0.02% or less, about 0.01% or less, about 0.005% or less, or about 0.001% or less by weight.

In some embodiments, the total impurity comprises one or more impurities with relative retention times from about 0.15 to about 1.85 under HPLC Method A. In some embodiments, the total impurity comprises one or more impurities with relative retention times from about 0.2 to about 1.80 under HPLC Method A.

In some embodiments, the total impurity comprises one or more impurities with relative retention times from about 0.11 to about 1.90 under HPLC Method A. In some embodiments, the total impurity comprises one or more impurities with relative retention times from about 0.12 to about 1.90 under HPLC Method A. In some embodiments, the total impurity comprises one or more impurities with relative retention times from about 0.13 to about 1.90 under HPLC Method A. In some embodiments, the total impurity comprises one or more impurities with relative retention times from about 0.14 to about 1.90 under HPLC Method A. In some embodiments, the total impurity comprises one or more impurities with relative retention times from about 0.15 to about 1.90 under HPLC Method A. In some embodiments, the total impurity comprises one or more impurities with relative retention times from about 0.16 to about 1.90 under HPLC Method A. In some embodiments, the total impurity comprises one or more impurities with relative retention times from about 0.17 to about 1.90 under HPLC Method A. In some embodiments, the total impurity comprises one or more impurities with relative retention times from about 0.18 to about 1.90 under HPLC Method A. In some embodiments, the total impurity comprises one or more impurities with relative retention times from about 0.19 to about 1.90 under HPLC Method A. In some embodiments, the total impurity comprises one or more impurities with relative retention times from about 0.20 to about 1.90 under HPLC Method A.

In some embodiments, the total impurity comprises one or more impurities with relative retention times from about 0.10 to about 1.87 under HPLC Method A. In some embodiments, the total impurity comprises one or more impurities with relative retention times from about 0.11 to about 1.87 under HPLC Method A. In some embodiments, the total impurity comprises one or more impurities with relative retention times from about 0.12 to about 1.87 under HPLC Method A. In some embodiments, the total impurity comprises one or more impurities with relative retention times from about 0.13 to about 1.87 under HPLC Method A. In some embodiments, the total impurity comprises one or more impurities with relative retention times from about 0.14 to about 1.87 under HPLC Method A. In some embodiments, the total impurity comprises one or more impurities with relative retention times from about 0.15 to about 1.87 under HPLC Method A. In some embodiments, the total impurity comprises one or more impurities with relative retention times from about 0.16 to about 1.87 under HPLC Method A. In some embodiments, the total impurity comprises one or more impurities with relative retention times from about 0.17 to about 1.87 under HPLC Method A. In some embodiments, the total impurity comprises one or more impurities with relative retention times from about 0.18 to about 1.87 under HPLC Method A. In some embodiments, the total impurity comprises one or more impurities with relative retention times from about 0.19 to about 1.87 under HPLC Method A. In some embodiments, total impurity comprises one or more impurities with relative retention times from about 0.20 to about 1.87 under HPLC Method A.

In some embodiments, the total impurity comprises one or more impurities with relative retention times from about 0.10 to about 1.85 under HPLC Method A. In some embodiments, the total impurity comprises one or more impurities with relative retention times from about 0.11 to about 1.85 under HPLC Method A. In some embodiments, the total impurity comprises one or more impurities with relative retention times from about 0.12 to about 1.85 under HPLC Method A. In some embodiments, the total impurity comprises one or more impurities with relative retention times from about 0.13 to about 1.85 under HPLC Method A. In some embodiments, the total impurity comprises one or more impurities with relative retention times from about 0.14 to about 1.85 under HPLC Method A. In some embodiments, the total impurity comprises one or more impurities with relative retention times from about 0.15 to about 1.85 under HPLC Method A. In some embodiments, the total impurity comprises one or more impurities with relative retention times from about 0.16 to about 1.85 under HPLC Method A. In some embodiments, the total impurity comprises one or more impurities with relative retention times from about 0.17 to about 1.85 under HPLC Method A. In some embodiments, the total impurity comprises one or more impurities with relative retention times from about 0.18 to about 1.85 under HPLC Method A. In some embodiments, the total impurity comprises one or more impurities with relative retention times from about 0.19 to about 1.85 under HPLC Method A. In some embodiments, the total impurity comprises one or more impurities with relative retention times from about 0.20 to about 1.85 under HPLC Method A.

Total Impurity

In some embodiments, the total impurity is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight. In some embodiments, the total impurity is about 1.5% by weight. In some embodiments, the total impurity is about 1.4% by weight. In some embodiments, the total impurity is about 1.3% by weight. In some embodiments, the total impurity is about 1.2% by weight. In some embodiments, the total impurity is about 1.1% by weight. In some embodiments, the total impurity is about 1.0% by weight. In some embodiments, the total impurity is about 0.9% by weight. In some embodiments, the total impurity is about 0.8% by weight. In some embodiments, the total impurity is about 0.7% by weight. In some embodiments, the total impurity is about 0.6% by weight. In some embodiments, the total impurity is about 0.5% by weight. In some embodiments, the total impurity is about 0.4% by weight. In some embodiments, the total impurity is about 0.3% by weight. In some embodiments, the total impurity is about 0.2% by weight. In some embodiments, the total impurity is about 0.1% by weight. In some embodiments, the total impurity is about 0.09% by weight. In some embodiments, the total impurity is about 0.08% by weight. In some embodiments, the total impurity is about 0.07% by weight. In some embodiments, the total impurity is about 0.06% by weight. In some embodiments, the total impurity is about 0.05% by weight. In some embodiments, the total impurity is about 0.04% by weight. In some embodiments, the total impurity is about 0.03% by weight. In some embodiments, the total impurity is about 0.02% by weight. In some embodiments, the total impurity is about 0.01% by weight. In some embodiments, the total impurity is about 0.005% by weight. In some embodiments, the total impurity is about 0.001% by weight.

In some embodiments, the total impurity is from about 1.5% to about 0.001%, about 1.4% to about 0.001%, about 1.3% to about 0.001%, about 1.2% to about 0.001%, about 1.1% to about 0.001%, about 1.0% to about 0.001%, about 0.9% to about 0.001%, about 0.8% to about 0.001%, about 0.7% to about 0.001%, about 0.6% to about 0.001%, about 0.5% to about 0.001%, about 0.4% to about 0.001%, about 0.3% to about 0.001%, about 0.2% to about 0.001%, about 0.1% to about 0.001%, about 0.09% to about 0.001%, about 0.08% to about 0.001%, about 0.07% to about 0.001%, about 0.06% to about 0.001%, about 0.05% to about 0.001%, about 0.04% to about 0.001%, about 0.03% to about 0.001%, about 0.02% to about 0.001%, about 0.01% to about 0.001%, or about 0.005% to about 0.001% by weight.

In some embodiments, the total impurity is from about 1.5% to about 0.01%, about 1.4% to about 0.01%, about 1.3% to about 0.01%, about 1.2% to about 0.01%, about 1.1% to about 0.01%, about 1.0% to about 0.01%, about 0.9% to about 0.01%, about 0.8% to about 0.01%, about 0.7% to about 0.01%, about 0.6% to about 0.01%, about 0.5% to about 0.01%, about 0.4% to about 0.01%, about 0.3% to about 0.01%, about 0.2% to about 0.01%, about 0.1% to about 0.01%, about 0.09% to about 0.01%, about 0.08% to about 0.01%, about 0.07% to about 0.01%, about 0.06% to about 0.01%, about 0.05% to about 0.01%, about 0.04% to about 0.01%, about 0.03% to about 0.01%, or about 0.02% to about 0.01% by weight.

In some embodiments, the total impurity is from about 1.5% to about 0.1%, about 1.4% to about 0.1%, about 1.3% to about 0.1%, about 1.2% to about 0.1%, about 1.1% to about 0.1%, about 1.0% to about 0.1%, about 0.9% to about 0.1%, about 0.8% to about 0.1%, about 0.7% to about 0.1%, about 0.6% to about 0.1%, about 0.5% to about 0.1%, about 0.4% to about 0.1%, about 0.3% to about 0.1%, or about 0.2% to about 0.1% by weight.

In some embodiments, the total impurity is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight. In some embodiments, the total impurity is less than about 1.5% by weight. In some embodiments, the total impurity is less than about 1.4% by weight. In some embodiments, the total impurity is less than about 1.3% by weight. In some embodiments, the total impurity is less than about 1.2% by weight. In some embodiments, the total impurity is less than about 1.1% by weight. In some embodiments, the total impurity is less than about 1.0% by weight. In some embodiments, the total impurity is less than about 0.9% by weight. In some embodiments, the total impurity is less than about 0.8% by weight. In some embodiments, the total impurity is less than about 0.7% by weight. In some embodiments, the total impurity is less than about 0.6% by weight. In some embodiments, the total impurity is less than about 0.5% by weight. In some embodiments, the total impurity is less than about 0.4% by weight. In some embodiments, the total impurity is less than about 0.3% by weight. In some embodiments, the total impurity is less than about 0.2% by weight. In some embodiments, the total impurity is less than about 0.1% by weight. In some embodiments, the total impurity is less than about 0.09% by weight. In some embodiments, the total impurity is less than about 0.08% by weight. In some embodiments, the total impurity is less than about 0.07% by weight. In some embodiments, the total impurity is less than about 0.06% by weight. In some embodiments, the total impurity is less than about 0.05% by weight. In some embodiments, the total impurity is less than about 0.04% by weight. In some embodiments, the total impurity is less than about 0.03% by weight. In some embodiments, the total impurity is less than about 0.02% by weight. In some embodiments, the total impurity is less than about 0.01% by weight. In some embodiments, the total impurity is less than about 0.005% by weight. In some embodiments, the total impurity is less than about 0.001% by weight.

In some embodiments, the total impurity is from less than about 1.5% to about 0.001%, less than about 1.4% to about 0.001%, less than about 1.3% to about 0.001%, less than about 1.2% to about 0.001%, less than about 1.1% to about 0.001%, less than about 1.0% to about 0.001%, less than about 0.9% to about 0.001%, less than about 0.8% to about 0.001%, less than about 0.7% to about 0.001%, less than about 0.6% to about 0.001%, less than about 0.5% to about 0.001%, less than about 0.4% to about 0.001%, less than about 0.3% to about 0.001%, less than about 0.2% to about 0.001%, less than about 0.1% to about 0.001%, less than about 0.09% to about 0.001%, less than about 0.08% to about 0.001%, less than about 0.07% to about 0.001%, less than about 0.06% to about 0.001%, less than about 0.05% to about 0.001%, less than about 0.04% to about 0.001%, less than about 0.03% to about 0.001%, less than about 0.02% to about 0.001%, less than about 0.01% to about 0.001%, or less than about 0.005% to about 0.001% by weight.

In some embodiments, the total impurity is from less than about 1.5% to about 0.01%, less than about 1.4% to about 0.01%, less than about 1.3% to about 0.01%, less than about 1.2% to about 0.01%, less than about 1.1% to about 0.01%, less than about 1.0% to about 0.01%, less than about 0.9% to about 0.01%, less than about 0.8% to about 0.01%, less than about 0.7% to about 0.01%, less than about 0.6% to about 0.01%, less than about 0.5% to about 0.01%, less than about 0.4% to about 0.01%, less than about 0.3% to about 0.01%, less than about 0.2% to about 0.01%, less than about 0.1% to about 0.01%, less than about 0.09% to about 0.01%, less than about 0.08% to about 0.01%, less than about 0.07% to about 0.01%, less than about 0.06% to about 0.01%, less than about 0.05% to about 0.01%, less than about 0.04% to about 0.01%, less than about 0.03% to about 0.01%, or less than about 0.02% to about 0.01% by weight.

In some embodiments, the total impurity is from less than about 1.5% to about 0.1%, less than about 1.4% to about 0.1%, less than about 1.3% to about 0.1%, less than about 1.2% to about 0.1%, less than about 1.1% to about 0.1%, less than about 1.0% to about 0.1%, less than about 0.9% to about 0.1%, less than about 0.8% to about 0.1%, less than about 0.7% to about 0.1%, less than about 0.6% to about 0.1%, less than about 0.5% to about 0.1%, less than about 0.4% to about 0.1%, less than about 0.3% to about 0.1%, or less than about 0.2% to about 0.1% by weight.

In some embodiments, the total impurity is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 0 months of storage. In some embodiments, the total impurity is about 1.5% by weight after 0 months of storage. In some embodiments, the total impurity is about 1.4% by weight after 0 months of storage. In some embodiments, the total impurity is about 1.3% by weight after 0 months of storage. In some embodiments, the total impurity is about 1.2% by weight after 0 months of storage. In some embodiments, the total impurity is about 1.1% by weight after 0 months of storage. In some embodiments, the total impurity is about 1.0% by weight after 0 months of storage. In some embodiments, the total impurity is about 0.9% by weight after 0 months of storage. In some embodiments, the total impurity is about 0.8% by weight after 0 months of storage. In some embodiments, the total impurity is about 0.7% by weight after 0 months of storage. In some embodiments, the total impurity is about 0.6% by weight after 0 months of storage. In some embodiments, the total impurity is about 0.5% by weight after 0 months of storage. In some embodiments, the total impurity is about 0.4% by weight after 0 months of storage. In some embodiments, the total impurity is about 0.3% by weight after 0 months of storage. In some embodiments, the total impurity is about 0.2% by weight after 0 months of storage. In some embodiments, the total impurity is about 0.1% by weight after 0 months of storage. In some embodiments, the total impurity is about 0.09% by weight after 0 months of storage. In some embodiments, the total impurity is about 0.08% by weight after 0 months of storage. In some embodiments, the total impurity is about 0.07% by weight after 0 months of storage. In some embodiments, the total impurity is about 0.06% by weight after 0 months of storage. In some embodiments, the total impurity is about 0.05% by weight after 0 months of storage. In some embodiments, the total impurity is about 0.04% by weight after 0 months of storage. In some embodiments, the total impurity is about 0.03% by weight after 0 months of storage. In some embodiments, the total impurity is about 0.02% by weight after 0 months of storage. In some embodiments, the total impurity is about 0.01% by weight after 0 months of storage. In some embodiments, the total impurity is about 0.005% by weight after 0 months of storage. In some embodiments, the total impurity is about 0.001% by weight after 0 months of storage.

In some embodiments, the total impurity is from about 1.5% to about 0.001%, about 1.4% to about 0.001%, about 1.3% to about 0.001%, about 1.2% to about 0.001%, about 1.1% to about 0.001%, about 1.0% to about 0.001%, about 0.9% to about 0.001%, about 0.8% to about 0.001%, about 0.7% to about 0.001%, about 0.6% to about 0.001%, about 0.5% to about 0.001%, about 0.4% to about 0.001%, about 0.3% to about 0.001%, about 0.2% to about 0.001%, about 0.1% to about 0.001%, about 0.09% to about 0.001%, about 0.08% to about 0.001%, about 0.07% to about 0.001%, about 0.06% to about 0.001%, about 0.05% to about 0.001%, about 0.04% to about 0.001%, about 0.03% to about 0.001%, about 0.02% to about 0.001%, about 0.01% to about 0.001%, or about 0.005% to about 0.001% by weight after 0 months of storage.

In some embodiments, the total impurity is from about 1.5% to about 0.01%, about 1.4% to about 0.01%, about 1.3% to about 0.01%, about 1.2% to about 0.01%, about 1.1% to about 0.01%, about 1.0% to about 0.01%, about 0.9% to about 0.01%, about 0.8% to about 0.01%, about 0.7% to about 0.01%, about 0.6% to about 0.01%, about 0.5% to about 0.01%, about 0.4% to about 0.01%, about 0.3% to about 0.01%, about 0.2% to about 0.01%, about 0.1% to about 0.01%, about 0.09% to about 0.01%, about 0.08% to about 0.01%, about 0.07% to about 0.01%, about 0.06% to about 0.01%, about 0.05% to about 0.01%, about 0.04% to about 0.01%, about 0.03% to about 0.01%, or about 0.02% to about 0.01% by weight after 0 months of storage.

In some embodiments, the total impurity is from about 1.5% to about 0.1%, about 1.4% to about 0.1%, about 1.3% to about 0.1%, about 1.2% to about 0.1%, about 1.1% to about 0.1%, about 1.0% to about 0.1%, about 0.9% to about 0.1%, about 0.8% to about 0.1%, about 0.7% to about 0.1%, about 0.6% to about 0.1%, about 0.5% to about 0.1%, about 0.4% to about 0.1%, about 0.3% to about 0.1%, or about 0.2% to about 0.1% by weight after 0 months of storage.

In some embodiments, the total impurity is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 0 months of storage. In some embodiments, the total impurity is less than about 1.5% by weight after 0 months of storage. In some embodiments, the total impurity is less than about 1.4% by weight after 0 months of storage. In some embodiments, the total impurity is less than about 1.3% by weight after 0 months of storage. In some embodiments, the total impurity is less than about 1.2% by weight after 0 months of storage. In some embodiments, the total impurity is less than about 1.1% by weight after 0 months of storage. In some embodiments, the total impurity is less than about 1.0% by weight after 0 months of storage. In some embodiments, the total impurity is less than about 0.9% by weight after 0 months of storage. In some embodiments, the total impurity is less than about 0.8% by weight after 0 months of storage. In some embodiments, the total impurity is less than about 0.7% by weight after 0 months of storage. In some embodiments, the total impurity is less than about 0.6% by weight after 0 months of storage. In some embodiments, the total impurity is less than about 0.5% by weight after 0 months of storage. In some embodiments, the total impurity is less than about 0.4% by weight after 0 months of storage. In some embodiments, the total impurity is less than about 0.3% by weight after 0 months of storage. In some embodiments, the total impurity is less than about 0.2% by weight after 0 months of storage. In some embodiments, the total impurity is less than about 0.1% by weight after 0 months of storage. In some embodiments, the total impurity is less than about 0.09% by weight after 0 months of storage. In some embodiments, the total impurity is less than about 0.08% by weight after 0 months of storage. In some embodiments, the total impurity is less than about 0.07% by weight after 0 months of storage. In some embodiments, the total impurity is less than about 0.06% by weight after 0 months of storage. In some embodiments, the total impurity is less than about 0.05% by weight after 0 months of storage. In some embodiments, the total impurity is less than about 0.04% by weight after 0 months of storage. In some embodiments, the total impurity is less than about 0.03% by weight after 0 months of storage. In some embodiments, the total impurity is less than about 0.02% by weight after 0 months of storage. In some embodiments, the total impurity is less than about 0.01% by weight after 0 months of storage. In some embodiments, the total impurity is less than about 0.005% by weight after 0 months of storage. In some embodiments, the total impurity is less than about 0.001% by weight after 0 months of storage.

In some embodiments, the total impurity is from less than about 1.5% to about 0.001%, less than about 1.4% to about 0.001%, less than about 1.3% to about 0.001%, less than about 1.2% to about 0.001%, less than about 1.1% to about 0.001%, less than about 1.0% to about 0.001%, less than about 0.9% to about 0.001%, less than about 0.8% to about 0.001%, less than about 0.7% to about 0.001%, less than about 0.6% to about 0.001%, less than about 0.5% to about 0.001%, less than about 0.4% to about 0.001%, less than about 0.3% to about 0.001%, less than about 0.2% to about 0.001%, less than about 0.1% to about 0.001%, less than about 0.09% to about 0.001%, less than about 0.08% to about 0.001%, less than about 0.07% to about 0.001%, less than about 0.06% to about 0.001%, less than about 0.05% to about 0.001%, less than about 0.04% to about 0.001%, less than about 0.03% to about 0.001%, less than about 0.02% to about 0.001%, less than about 0.01% to about 0.001%, or less than about 0.005% to about 0.001% by weight after 0 months of storage.

In some embodiments, the total impurity is from less than about 1.5% to about 0.01%, less than about 1.4% to about 0.01%, less than about 1.3% to about 0.01%, less than about 1.2% to about 0.01%, less than about 1.1% to about 0.01%, less than about 1.0% to about 0.01%, less than about 0.9% to about 0.01%, less than about 0.8% to about 0.01%, less than about 0.7% to about 0.01%, less than about 0.6% to about 0.01%, less than about 0.5% to about 0.01%, less than about 0.4% to about 0.01%, less than about 0.3% to about 0.01%, less than about 0.2% to about 0.01%, less than about 0.1% to about 0.01%, less than about 0.09% to about 0.01%, less than about 0.08% to about 0.01%, less than about 0.07% to about 0.01%, less than about 0.06% to about 0.01%, less than about 0.05% to about 0.01%, less than about 0.04% to about 0.01%, less than about 0.03% to about 0.01%, or less than about 0.02% to about 0.01% by weight after 0 months of storage.

In some embodiments, the total impurity is from less than about 1.5% to about 0.1%, less than about 1.4% to about 0.1%, less than about 1.3% to about 0.1%, less than about 1.2% to about 0.1%, less than about 1.1% to about 0.1%, less than about 1.0% to about 0.1%, less than about 0.9% to about 0.1%, less than about 0.8% to about 0.1%, less than about 0.7% to about 0.1%, less than about 0.6% to about 0.1%, less than about 0.5% to about 0.1%, less than about 0.4% to about 0.1%, less than about 0.3% to about 0.1%, or less than about 0.2% to about 0.1% by weight after 0 months of storage.

In some embodiments, the total impurity is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 12 months of storage. In some embodiments, the total impurity is about 1.5% by weight after 12 months of storage. In some embodiments, the total impurity is about 1.4% by weight after 12 months of storage. In some embodiments, the total impurity is about 1.3% by weight after 12 months of storage. In some embodiments, the total impurity is about 1.2% by weight after 12 months of storage. In some embodiments, the total impurity is about 1.1% by weight after 12 months of storage. In some embodiments, the total impurity is about 1.0% by weight after 12 months of storage.

In some embodiments, the total impurity is about 0.9% by weight after 12 months of storage. In some embodiments, the total impurity is about 0.8% by weight after 12 months of storage. In some embodiments, the total impurity is about 0.7% by weight after 12 months of storage. In some embodiments, the total impurity is about 0.6% by weight after 12 months of storage. In some embodiments, the total impurity is about 0.5% by weight after 12 months of storage. In some embodiments, the total impurity is about 0.4% by weight after 12 months of storage. In some embodiments, the total impurity is about 0.3% by weight after 12 months of storage. In some embodiments, the total impurity is about 0.2% by weight after 12 months of storage. In some embodiments, the total impurity is about 0.1% by weight after 12 months of storage. In some embodiments, the total impurity is about 0.09% by weight after 12 months of storage. In some embodiments, the total impurity is about 0.08% by weight after 12 months of storage. In some embodiments, the total impurity is about 0.07% by weight after 12 months of storage. In some embodiments, the total impurity is about 0.06% by weight after 12 months of storage. In some embodiments, the total impurity is about 0.05% by weight after 12 months of storage. In some embodiments, the total impurity is about 0.04% by weight after 12 months of storage. In some embodiments, the total impurity is about 0.03% by weight after 12 months of storage. In some embodiments, the total impurity is about 0.02% by weight after 12 months of storage. In some embodiments, the total impurity is about 0.01% by weight after 12 months of storage. In some embodiments, the total impurity is about 0.005% by weight after 12 months of storage. In some embodiments, the total impurity is about 0.001% by weight after 12 months of storage.

In some embodiments, the total impurity is from about 1.5% to about 0.001%, about 1.4% to about 0.001%, about 1.3% to about 0.001%, about 1.2% to about 0.001%, about 1.1% to about 0.001%, about 1.0% to about 0.001%, about 0.9% to about 0.001%, about 0.8% to about 0.001%, about 0.7% to about 0.001%, about 0.6% to about 0.001%, about 0.5% to about 0.001%, about 0.4% to about 0.001%, about 0.3% to about 0.001%, about 0.2% to about 0.001%, about 0.1% to about 0.001%, about 0.09% to about 0.001%, about 0.08% to about 0.001%, about 0.07% to about 0.001%, about 0.06% to about 0.001%, about 0.05% to about 0.001%, about 0.04% to about 0.001%, about 0.03% to about 0.001%, about 0.02% to about 0.001%, about 0.01% to about 0.001%, or about 0.005% to about 0.001% by weight after 12 months of storage.

In some embodiments, the total impurity is from about 1.5% to about 0.01%, about 1.4% to about 0.01%, about 1.3% to about 0.01%, about 1.2% to about 0.01%, about 1.1% to about 0.01%, about 1.0% to about 0.01%, about 0.9% to about 0.01%, about 0.8% to about 0.01%, about 0.7% to about 0.01%, about 0.6% to about 0.01%, about 0.5% to about 0.01%, about 0.4% to about 0.01%, about 0.3% to about 0.01%, about 0.2% to about 0.01%, about 0.1% to about 0.01%, about 0.09% to about 0.01%, about 0.08% to about 0.01%, about 0.07% to about 0.01%, about 0.06% to about 0.01%, about 0.05% to about 0.01%, about 0.04% to about 0.01%, about 0.03% to about 0.01%, or about 0.02% to about 0.01% by weight after 12 months of storage.

In some embodiments, the total impurity is from about 1.5% to about 0.1%, about 1.4% to about 0.1%, about 1.3% to about 0.1%, about 1.2% to about 0.1%, about 1.1% to about 0.1%, about 1.0% to about 0.1%, about 0.9% to about 0.1%, about 0.8% to about 0.1%, about 0.7% to about 0.1%, about 0.6% to about 0.1%, about 0.5% to about 0.1%, about 0.4% to about 0.1%, about 0.3% to about 0.1%, or about 0.2% to about 0.1% by weight after 12 months of storage.

In some embodiments, the total impurity is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 12 months of storage. In some embodiments, the total impurity is less than about 1.5% by weight after 12 months of storage. In some embodiments, the total impurity is less than about 1.4% by weight after 12 months of storage. In some embodiments, the total impurity is less than about 1.3% by weight after 12 months of storage. In some embodiments, the total impurity is less than about 1.2% by weight after 12 months of storage. In some embodiments, the total impurity is less than about 1.1% by weight after 12 months of storage. In some embodiments, the total impurity is less than about 1.0% by weight after 12 months of storage. In some embodiments, the total impurity is less than about 0.9% by weight after 12 months of storage. In some embodiments, the total impurity is less than about 0.8% by weight after 12 months of storage. In some embodiments, the total impurity is less than about 0.7% by weight after 12 months of storage. In some embodiments, the total impurity is less than about 0.6% by weight after 12 months of storage. In some embodiments, the total impurity is less than about 0.5% by weight after 12 months of storage. In some embodiments, the total impurity is less than about 0.4% by weight after 12 months of storage. In some embodiments, the total impurity is less than about 0.3% by weight after 12 months of storage. In some embodiments, the total impurity is less than about 0.2% by weight after 12 months of storage. In some embodiments, the total impurity is less than about 0.1% by weight after 12 months of storage. In some embodiments, the total impurity is less than about 0.09% by weight after 12 months of storage. In some embodiments, the total impurity is less than about 0.08% by weight after 12 months of storage. In some embodiments, the total impurity is less than about 0.07% by weight after 12 months of storage. In some embodiments, the total impurity is less than about 0.06% by weight after 12 months of storage. In some embodiments, the total impurity is less than about 0.05% by weight after 12 months of storage. In some embodiments, the total impurity is less than about 0.04% by weight after 12 months of storage. In some embodiments, the total impurity is less than about 0.03% by weight after 12 months of storage. In some embodiments, the total impurity is less than about 0.02% by weight after 12 months of storage. In some embodiments, the total impurity is less than about 0.01% by weight after 12 months of storage. In some embodiments, the total impurity is less than about 0.005% by weight after 12 months of storage. In some embodiments, the total impurity is less than about 0.001% by weight after 12 months of storage.

In some embodiments, the total impurity is from less than about 1.5% to about 0.001%, less than about 1.4% to about 0.001%, less than about 1.3% to about 0.001%, less than about 1.2% to about 0.001%, less than about 1.1% to about 0.001%, less than about 1.0% to about 0.001%, less than about 0.9% to about 0.001%, less than about 0.8% to about 0.001%, less than about 0.7% to about 0.001%, less than about 0.6% to about 0.001%, less than about 0.5% to about 0.001%, less than about 0.4% to about 0.001%, less than about 0.3% to about 0.001%, less than about 0.2% to about 0.001%, less than about 0.1% to about 0.001%, less than about 0.09% to about 0.001%, less than about 0.08% to about 0.001%, less than about 0.07% to about 0.001%, less than about 0.06% to about 0.001%, less than about 0.05% to about 0.001%, less than about 0.04% to about 0.001%, less than about 0.03% to about 0.001%, less than about 0.02% to about 0.001%, less than about 0.01% to about 0.001%, or less than about 0.005% to about 0.001% by weight after 12 months of storage.

In some embodiments, the total impurity is from less than about 1.5% to about 0.01%, less than about 1.4% to about 0.01%, less than about 1.3% to about 0.01%, less than about 1.2% to about 0.01%, less than about 1.1% to about 0.01%, less than about 1.0% to about 0.01%, less than about 0.9% to about 0.01%, less than about 0.8% to about 0.01%, less than about 0.7% to about 0.01%, less than about 0.6% to about 0.01%, less than about 0.5% to about 0.01%, less than about 0.4% to about 0.01%, less than about 0.3% to about 0.01%, less than about 0.2% to about 0.01%, less than about 0.1% to about 0.01%, less than about 0.09% to about 0.01%, less than about 0.08% to about 0.01%, less than about 0.07% to about 0.01%, less than about 0.06% to about 0.01%, less than about 0.05% to about 0.01%, less than about 0.04% to about 0.01%, less than about 0.03% to about 0.01%, or less than about 0.02% to about 0.01% by weight after 12 months of storage.

In some embodiments, the total impurity is from less than about 1.5% to about 0.1%, less than about 1.4% to about 0.1%, less than about 1.3% to about 0.1%, less than about 1.2% to about 0.1%, less than about 1.1% to about 0.1%, less than about 1.0% to about 0.1%, less than about 0.9% to about 0.1%, less than about 0.8% to about 0.1%, less than about 0.7% to about 0.1%, less than about 0.6% to about 0.1%, less than about 0.5% to about 0.1%, less than about 0.4% to about 0.1%, less than about 0.3% to about 0.1%, or less than about 0.2% to about 0.1% by weight after 12 months of storage.

In some embodiments, the total impurity is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 18 months of storage. In some embodiments, the total impurity is about 1.5% by weight after 18 months of storage. In some embodiments, the total impurity is about 1.4% by weight after 18 months of storage. In some embodiments, the total impurity is about 1.3% by weight after 18 months of storage. In some embodiments, the total impurity is about 1.2% by weight after 18 months of storage. In some embodiments, the total impurity is about 1.1% by weight after 18 months of storage. In some embodiments, the total impurity is about 1.0% by weight after 18 months of storage. In some embodiments, the total impurity is about 0.9% by weight after 18 months of storage. In some embodiments, the total impurity is about 0.8% by weight after 18 months of storage. In some embodiments, the total impurity is about 0.7% by weight after 18 months of storage. In some embodiments, the total impurity is about 0.6% by weight after 18 months of storage. In some embodiments, the total impurity is about 0.5% by weight after 18 months of storage. In some embodiments, the total impurity is about 0.4% by weight after 18 months of storage. In some embodiments, the total impurity is about 0.3% by weight after 18 months of storage. In some embodiments, the total impurity is about 0.2% by weight after 18 months of storage. In some embodiments, the total impurity is about 0.1% by weight after 18 months of storage. In some embodiments, the total impurity is about 0.09% by weight after 18 months of storage. In some embodiments, the total impurity is about 0.08% by weight after 18 months of storage. In some embodiments, the total impurity is about 0.07% by weight after 18 months of storage. In some embodiments, the total impurity is about 0.06% by weight after 18 months of storage. In some embodiments, the total impurity is about 0.05% by weight after 18 months of storage. In some embodiments, the total impurity is about 0.04% by weight after 18 months of storage. In some embodiments, the total impurity is about 0.03% by weight after 18 months of storage. In some embodiments, the total impurity is about 0.02% by weight after 18 months of storage. In some embodiments, the total impurity is about 0.01% by weight after 18 months of storage. In some embodiments, the total impurity is about 0.005% by weight after 18 months of storage. In some embodiments, the total impurity is about 0.001% by weight after 18 months of storage.

In some embodiments, the total impurity is from about 1.5% to about 0.001%, about 1.4% to about 0.001%, about 1.3% to about 0.001%, about 1.2% to about 0.001%, about 1.1% to about 0.001%, about 1.0% to about 0.001%, about 0.9% to about 0.001%, about 0.8% to about 0.001%, about 0.7% to about 0.001%, about 0.6% to about 0.001%, about 0.5% to about 0.001%, about 0.4% to about 0.001%, about 0.3% to about 0.001%, about 0.2% to about 0.001%, about 0.1% to about 0.001%, about 0.09% to about 0.001%, about 0.08% to about 0.001%, about 0.07% to about 0.001%, about 0.06% to about 0.001%, about 0.05% to about 0.001%, about 0.04% to about 0.001%, about 0.03% to about 0.001%, about 0.02% to about 0.001%, about 0.01% to about 0.001%, or about 0.005% to about 0.001% by weight after 18 months of storage.

In some embodiments, the total impurity is from about 1.5% to about 0.01%, about 1.4% to about 0.01%, about 1.3% to about 0.01%, about 1.2% to about 0.01%, about 1.1% to about 0.01%, about 1.0% to about 0.01%, about 0.9% to about 0.01%, about 0.8% to about 0.01%, about 0.7% to about 0.01%, about 0.6% to about 0.01%, about 0.5% to about 0.01%, about 0.4% to about 0.01%, about 0.3% to about 0.01%, about 0.2% to about 0.01%, about 0.1% to about 0.01%, about 0.09% to about 0.01%, about 0.08% to about 0.01%, about 0.07% to about 0.01%, about 0.06% to about 0.01%, about 0.05% to about 0.01%, about 0.04% to about 0.01%, about 0.03% to about 0.01%, or about 0.02% to about 0.01% by weight after 18 months of storage.

In some embodiments, the total impurity is from about 1.5% to about 0.1%, about 1.4% to about 0.1%, about 1.3% to about 0.1%, about 1.2% to about 0.1%, about 1.1% to about 0.1%, about 1.0% to about 0.1%, about 0.9% to about 0.1%, about 0.8% to about 0.1%, about 0.7% to about 0.1%, about 0.6% to about 0.1%, about 0.5% to about 0.1%, about 0.4% to about 0.1%, about 0.3% to about 0.1%, or about 0.2% to about 0.1% by weight after 18 months of storage.

In some embodiments, the total impurity is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 18 months of storage. In some embodiments, the total impurity is less than about 1.5% by weight after 18 months of storage. In some embodiments, the total impurity is less than about 1.4% by weight after 18 months of storage. In some embodiments, the total impurity is less than about 1.3% by weight after 18 months of storage. In some embodiments, the total impurity is less than about 1.2% by weight after 18 months of storage. In some embodiments, the total impurity is less than about 1.1% by weight after 18 months of storage. In some embodiments, the total impurity is less than about 1.0% by weight after 18 months of storage. In some embodiments, the total impurity is less than about 0.9% by weight after 18 months of storage. In some embodiments, the total impurity is less than about 0.8% by weight after 18 months of storage. In some embodiments, the total impurity is less than about 0.7% by weight after 18 months of storage. In some embodiments, the total impurity is less than about 0.6% by weight after 18 months of storage. In some embodiments, the total impurity is less than about 0.5% by weight after 18 months of storage. In some embodiments, the total impurity is less than about 0.4% by weight after 18 months of storage. In some embodiments, the total impurity is less than about 0.3% by weight after 18 months of storage. In some embodiments, the total impurity is less than about 0.2% by weight after 18 months of storage. In some embodiments, the total impurity is less than about 0.1% by weight after 18 months of storage. In some embodiments, the total impurity is less than about 0.09% by weight after 18 months of storage. In some embodiments, the total impurity is less than about 0.08% by weight after 18 months of storage. In some embodiments, the total impurity is less than about 0.07% by weight after 18 months of storage. In some embodiments, the total impurity is less than about 0.06% by weight after 18 months of storage. In some embodiments, the total impurity is less than about 0.05% by weight after 18 months of storage. In some embodiments, the total impurity is less than about 0.04% by weight after 18 months of storage. In some embodiments, the total impurity is less than about 0.03% by weight after 18 months of storage. In some embodiments, the total impurity is less than about 0.02% by weight after 18 months of storage. In some embodiments, the total impurity is less than about 0.01% by weight after 18 months of storage. In some embodiments, the total impurity is less than about 0.005% by weight after 18 months of storage. In some embodiments, the total impurity is less than about 0.001% by weight after 18 months of storage.

In some embodiments, the total impurity is from less than about 1.5% to about 0.001%, less than about 1.4% to about 0.001%, less than about 1.3% to about 0.001%, less than about 1.2% to about 0.001%, less than about 1.1% to about 0.001%, less than about 1.0% to about 0.001%, less than about 0.9% to about 0.001%, less than about 0.8% to about 0.001%, less than about 0.7% to about 0.001%, less than about 0.6% to about 0.001%, less than about 0.5% to about 0.001%, less than about 0.4% to about 0.001%, less than about 0.3% to about 0.001%, less than about 0.2% to about 0.001%, less than about 0.1% to about 0.001%, less than about 0.09% to about 0.001%, less than about 0.08% to about 0.001%, less than about 0.07% to about 0.001%, less than about 0.06% to about 0.001%, less than about 0.05% to about 0.001%, less than about 0.04% to about 0.001%, less than about 0.03% to about 0.001%, less than about 0.02% to about 0.001%, less than about 0.01% to about 0.001%, or less than about 0.005% to about 0.001% by weight after 18 months of storage.

In some embodiments, the total impurity is from less than about 1.5% to about 0.01%, less than about 1.4% to about 0.01%, less than about 1.3% to about 0.01%, less than about 1.2% to about 0.01%, less than about 1.1% to about 0.01%, less than about 1.0% to about 0.01%, less than about 0.9% to about 0.01%, less than about 0.8% to about 0.01%, less than about 0.7% to about 0.01%, less than about 0.6% to about 0.01%, less than about 0.5% to about 0.01%, less than about 0.4% to about 0.01%, less than about 0.3% to about 0.01%, less than about 0.2% to about 0.01%, less than about 0.1% to about 0.01%, less than about 0.09% to about 0.01%, less than about 0.08% to about 0.01%, less than about 0.07% to about 0.01%, less than about 0.06% to about 0.01%, less than about 0.05% to about 0.01%, less than about 0.04% to about 0.01%, less than about 0.03% to about 0.01%, or less than about 0.02% to about 0.01% by weight after 18 months of storage.

In some embodiments, the total impurity is from less than about 1.5% to about 0.1%, less than about 1.4% to about 0.1%, less than about 1.3% to about 0.1%, less than about 1.2% to about 0.1%, less than about 1.1% to about 0.1%, less than about 1.0% to about 0.1%, less than about 0.9% to about 0.1%, less than about 0.8% to about 0.1%, less than about 0.7% to about 0.1%, less than about 0.6% to about 0.1%, less than about 0.5% to about 0.1%, less than about 0.4% to about 0.1%, less than about 0.3% to about 0.1%, or less than about 0.2% to about 0.1% by weight after 18 months of storage.

Specific Impurities

In some embodiments, the total impurity comprises an impurity with a relative retention time of about 0.43. In some embodiments, the total impurity comprises an impurity with a relative retention time of about 0.43±0.01, about 0.43±0.02, about 0.43±0.03, about 0.43±0.04, about 0.43±0.05, about 0.43±0.06, about 0.43±0.07, about 0.43±0.08, about 0.43±0.09, or about 0.43±0.10.

In some embodiments, the impurity with a relative retention time of about 0.43 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight. In some embodiments, the impurity with a relative retention time of about 0.43 is about 1.5% by weight. In some embodiments, the impurity with a relative retention time of about 0.43 is about 1.4% by weight. In some embodiments, the impurity with a relative retention time of about 0.43 is about 1.3% by weight. In some embodiments, the impurity with a relative retention time of about 0.43 is about 1.2% by weight. In some embodiments, the impurity with a relative retention time of about 0.43 is about 1.1% by weight. In some embodiments, the impurity with a relative retention time of about 0.43 is about 1.0% by weight. In some embodiments, the impurity with a relative retention time of about 0.43 is about 0.9% by weight. In some embodiments, the impurity with a relative retention time of about 0.43 is about 0.8% by weight. In some embodiments, the impurity with a relative retention time of about 0.43 is about 0.7% by weight. In some embodiments, the impurity with a relative retention time of about 0.43 is about 0.6% by weight. In some embodiments, the impurity with a relative retention time of about 0.43 is about 0.5% by weight. In some embodiments, the impurity with a relative retention time of about 0.43 is about 0.4% by weight. In some embodiments, the impurity with a relative retention time of about 0.43 is about 0.3% by weight. In some embodiments, the impurity with a relative retention time of about 0.43 is about 0.2% by weight. In some embodiments, the impurity with a relative retention time of about 0.43 is about 0.1% by weight. In some embodiments, the impurity with a relative retention time of about 0.43 is about 0.09% by weight. In some embodiments, the impurity with a relative retention time of about 0.43 is about 0.08% by weight. In some embodiments, the impurity with a relative retention time of about 0.43 is about 0.07% by weight. In some embodiments, the impurity with a relative retention time of about 0.43 is about 0.06% by weight. In some embodiments, the impurity with a relative retention time of about 0.43 is about 0.05% by weight. In some embodiments, the impurity with a relative retention time of about 0.43 is about 0.04% by weight. In some embodiments, the impurity with a relative retention time of about 0.43 is about 0.03% by weight. In some embodiments, the impurity with a relative retention time of about 0.43 is about 0.02% by weight. In some embodiments, the impurity with a relative retention time of about 0.43 is about 0.01% by weight. In some embodiments, the impurity with a relative retention time of about 0.43 is about 0.005% by weight. In some embodiments, the impurity with a relative retention time of about 0.43 is about 0.001% by weight.

In some embodiments, the impurity with a relative retention time of about 0.43 is from about 1.5% to about 0.001%, about 1.4% to about 0.001%, about 1.3% to about 0.001%, about 1.2% to about 0.001%, about 1.1% to about 0.001%, about 1.0% to about 0.001%, about 0.9% to about 0.001%, about 0.8% to about 0.001%, about 0.7% to about 0.001%, about 0.6% to about 0.001%, about 0.5% to about 0.001%, about 0.4% to about 0.001%, about 0.3% to about 0.001%, about 0.2% to about 0.001%, about 0.1% to about 0.001%, about 0.09% to about 0.001%, about 0.08% to about 0.001%, about 0.07% to about 0.001%, about 0.06% to about 0.001%, about 0.05% to about 0.001%, about 0.04% to about 0.001%, about 0.03% to about 0.001%, about 0.02% to about 0.001%, about 0.01% to about 0.001%, or about 0.005% to about 0.001% by weight.

In some embodiments, the impurity with a relative retention time of about 0.43 is from about 1.5% to about 0.01%, about 1.4% to about 0.01%, about 1.3% to about 0.01%, about 1.2% to about 0.01%, about 1.1% to about 0.01%, about 1.0% to about 0.01%, about 0.9% to about 0.01%, about 0.8% to about 0.01%, about 0.7% to about 0.01%, about 0.6% to about 0.01%, about 0.5% to about 0.01%, about 0.4% to about 0.01%, about 0.3% to about 0.01%, about 0.2% to about 0.01%, about 0.1% to about 0.01%, about 0.09% to about 0.01%, about 0.08% to about 0.01%, about 0.07% to about 0.01%, about 0.06% to about 0.01%, about 0.05% to about 0.01%, about 0.04% to about 0.01%, about 0.03% to about 0.01%, or about 0.02% to about 0.01% by weight.

In some embodiments, the impurity with a relative retention time of about 0.43 is from about 1.5% to about 0.1%, about 1.4% to about 0.1%, about 1.3% to about 0.1%, about 1.2% to about 0.1%, about 1.1% to about 0.1%, about 1.0% to about 0.1%, about 0.9% to about 0.1%, about 0.8% to about 0.1%, about 0.7% to about 0.1%, about 0.6% to about 0.1%, about 0.5% to about 0.1%, about 0.4% to about 0.1%, about 0.3% to about 0.1%, or about 0.2% to about 0.1% by weight.

In some embodiments, the impurity with a relative retention time of about 0.43 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight. In some embodiments, the impurity with a relative retention time of about 0.43 is less than about 1.5% by weight. In some embodiments, the impurity with a relative retention time of about 0.43 is less than about 1.4% by weight. In some embodiments, the impurity with a relative retention time of about 0.43 is less than about 1.3% by weight. In some embodiments, the impurity with a relative retention time of about 0.43 is less than about 1.2% by weight. In some embodiments, the impurity with a relative retention time of about 0.43 is less than about 1.1% by weight. In some embodiments, the impurity with a relative retention time of about 0.43 is less than about 1.0% by weight. In some embodiments, the impurity with a relative retention time of about 0.43 is less than about 0.9% by weight. In some embodiments, the impurity with a relative retention time of about 0.43 is less than about 0.8% by weight. In some embodiments, the impurity with a relative retention time of about 0.43 is less than about 0.7% by weight. In some embodiments, the impurity with a relative retention time of about 0.43 is less than about 0.6% by weight. In some embodiments, the impurity with a relative retention time of about 0.43 is less than about 0.5% by weight. In some embodiments, the impurity with a relative retention time of about 0.43 is less than about 0.4% by weight. In some embodiments, the impurity with a relative retention time of about 0.43 is less than about 0.3% by weight. In some embodiments, the impurity with a relative retention time of about 0.43 is less than about 0.2% by weight. In some embodiments, the impurity with a relative retention time of about 0.43 is less than about 0.1% by weight. In some embodiments, the impurity with a relative retention time of about 0.43 is less than about 0.09% by weight. In some embodiments, the impurity with a relative retention time of about 0.43 is less than about 0.08% by weight. In some embodiments, the impurity with a relative retention time of about 0.43 is less than about 0.07% by weight. In some embodiments, the impurity with a relative retention time of about 0.43 is less than about 0.06% by weight. In some embodiments, the impurity with a relative retention time of about 0.43 is less than about 0.05% by weight. In some embodiments, the impurity with a relative retention time of about 0.43 is less than about 0.04% by weight. In some embodiments, the impurity with a relative retention time of about 0.43 is less than about 0.03% by weight. In some embodiments, the impurity with a relative retention time of about 0.43 is less than about 0.02% by weight. In some embodiments, the impurity with a relative retention time of about 0.43 is less than about 0.01% by weight. In some embodiments, the impurity with a relative retention time of about 0.43 is less than about 0.005% by weight. In some embodiments, the impurity with a relative retention time of about 0.43 is less than about 0.001% by weight.

In some embodiments, the impurity with a relative retention time of about 0.43 is from less than about 1.5% to about 0.001%, less than about 1.4% to about 0.001%, less than about 1.3% to about 0.001%, less than about 1.2% to about 0.001%, less than about 1.1% to about 0.001%, less than about 1.0% to about 0.001%, less than about 0.9% to about 0.001%, less than about 0.8% to about 0.001%, less than about 0.7% to about 0.001%, less than about 0.6% to about 0.001%, less than about 0.5% to about 0.001%, less than about 0.4% to about 0.001%, less than about 0.3% to about 0.001%, less than about 0.2% to about 0.001%, less than about 0.1% to about 0.001%, less than about 0.09% to about 0.001%, less than about 0.08% to about 0.001%, less than about 0.07% to about 0.001%, less than about 0.06% to about 0.001%, less than about 0.05% to about 0.001%, less than about 0.04% to about 0.001%, less than about 0.03% to about 0.001%, less than about 0.02% to about 0.001%, less than about 0.01% to about 0.001%, or less than about 0.005% to about 0.001% by weight.

In some embodiments, the impurity with a relative retention time of about 0.43 is from less than about 1.5% to about 0.01%, less than about 1.4% to about 0.01%, less than about 1.3% to about 0.01%, less than about 1.2% to about 0.01%, less than about 1.1% to about 0.01%, less than about 1.0% to about 0.01%, less than about 0.9% to about 0.01%, less than about 0.8% to about 0.01%, less than about 0.7% to about 0.01%, less than about 0.6% to about 0.01%, less than about 0.5% to about 0.01%, less than about 0.4% to about 0.01%, less than about 0.3% to about 0.01%, less than about 0.2% to about 0.01%, less than about 0.1% to about 0.01%, less than about 0.09% to about 0.01%, less than about 0.08% to about 0.01%, less than about 0.07% to about 0.01%, less than about 0.06% to about 0.01%, less than about 0.05% to about 0.01%, less than about 0.04% to about 0.01%, less than about 0.03% to about 0.01%, or less than about 0.02% to about 0.01% by weight.

In some embodiments, the impurity with a relative retention time of about 0.43 is from less than about 1.5% to about 0.1%, less than about 1.4% to about 0.1%, less than about 1.3% to about 0.1%, less than about 1.2% to about 0.1%, less than about 1.1% to about 0.1%, less than about 1.0% to about 0.1%, less than about 0.9% to about 0.1%, less than about 0.8% to about 0.1%, less than about 0.7% to about 0.1%, less than about 0.6% to about 0.1%, less than about 0.5% to about 0.1%, less than about 0.4% to about 0.1%, less than about 0.3% to about 0.1%, or less than about 0.2% to about 0.1% by weight.

In some embodiments, the impurity with a relative retention time of about 0.43 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 0 months of storage. In some embodiments, the impurity with a relative retention time of about 0.43 is about 1.5% by weight after 0 months of storage. In some embodiments, the impurity with a relative retention time of about 0.43 is about 1.4% by weight after 0 months of storage. In some embodiments, the impurity with a relative retention time of about 0.43 is about 1.3% by weight after 0 months of storage. In some embodiments, the impurity with a relative retention time of about 0.43 is about 1.2% by weight after 0 months of storage. In some embodiments, the impurity with a relative retention time of about 0.43 is about 1.1% by weight after 0 months of storage. In some embodiments, the impurity with a relative retention time of about 0.43 is about 1.0% by weight after 0 months of storage. In some embodiments, the impurity with a relative retention time of about 0.43 is about 0.9% by weight after 0 months of storage. In some embodiments, the impurity with a relative retention time of about 0.43 is about 0.8% by weight after 0 months of storage. In some embodiments, the impurity with a relative retention time of about 0.43 is about 0.7% by weight after 0 months of storage. In some embodiments, the impurity with a relative retention time of about 0.43 is about 0.6% by weight after 0 months of storage. In some embodiments, the impurity with a relative retention time of about 0.43 is about 0.5% by weight after 0 months of storage. In some embodiments, the impurity with a relative retention time of about 0.43 is about 0.4% by weight after 0 months of storage. In some embodiments, the impurity with a relative retention time of about 0.43 is about 0.3% by weight after 0 months of storage. In some embodiments, the impurity with a relative retention time of about 0.43 is about 0.2% by weight after 0 months of storage. In some embodiments, the impurity with a relative retention time of about 0.43 is about 0.1% by weight after 0 months of storage. In some embodiments, the impurity with a relative retention time of about 0.43 is about 0.09% by weight after 0 months of storage. In some embodiments, the impurity with a relative retention time of about 0.43 is about 0.08% by weight after 0 months of storage. In some embodiments, the impurity with a relative retention time of about 0.43 is about 0.07% by weight after 0 months of storage. In some embodiments, the impurity with a relative retention time of about 0.43 is about 0.06% by weight after 0 months of storage. In some embodiments, the impurity with a relative retention time of about 0.43 is about 0.05% by weight after 0 months of storage. In some embodiments, the impurity with a relative retention time of about 0.43 is about 0.04% by weight after 0 months of storage. In some embodiments, the impurity with a relative retention time of about 0.43 is about 0.03% by weight after 0 months of storage. In some embodiments, the impurity with a relative retention time of about 0.43 is about 0.02% by weight after 0 months of storage. In some embodiments, the impurity with a relative retention time of about 0.43 is about 0.01% by weight after 0 months of storage. In some embodiments, the impurity with a relative retention time of about 0.43 is about 0.005% by weight after 0 months of storage. In some embodiments, the impurity with a relative retention time of about 0.43 is about 0.001% by weight after 0 months of storage.

In some embodiments, the impurity with a relative retention time of about 0.43 is from about 1.5% to about 0.001%, about 1.4% to about 0.001%, about 1.3% to about 0.001%, about 1.2% to about 0.001%, about 1.1% to about 0.001%, about 1.0% to about 0.001%, about 0.9% to about 0.001%, about 0.8% to about 0.001%, about 0.7% to about 0.001%, about 0.6% to about 0.001%, about 0.5% to about 0.001%, about 0.4% to about 0.001%, about 0.3% to about 0.001%, about 0.2% to about 0.001%, about 0.1% to about 0.001%, about 0.09% to about 0.001%, about 0.08% to about 0.001%, about 0.07% to about 0.001%, about 0.06% to about 0.001%, about 0.05% to about 0.001%, about 0.04% to about 0.001%, about 0.03% to about 0.001%, about 0.02% to about 0.001%, about 0.01% to about 0.001%, or about 0.005% to about 0.001% by weight after 0 months of storage.

In some embodiments, the impurity with a relative retention time of about 0.43 is from about 1.5% to about 0.01%, about 1.4% to about 0.01%, about 1.3% to about 0.01%, about 1.2% to about 0.01%, about 1.1% to about 0.01%, about 1.0% to about 0.01%, about 0.9% to about 0.01%, about 0.8% to about 0.01%, about 0.7% to about 0.01%, about 0.6% to about 0.01%, about 0.5% to about 0.01%, about 0.4% to about 0.01%, about 0.3% to about 0.01%, about 0.2% to about 0.01%, about 0.1% to about 0.01%, about 0.09% to about 0.01%, about 0.08% to about 0.01%, about 0.07% to about 0.01%, about 0.06% to about 0.01%, about 0.05% to about 0.01%, about 0.04% to about 0.01%, about 0.03% to about 0.01%, or about 0.02% to about 0.01% by weight after 0 months of storage.

In some embodiments, the impurity with a relative retention time of about 0.43 is from about 1.5% to about 0.1%, about 1.4% to about 0.1%, about 1.3% to about 0.1%, about 1.2% to about 0.1%, about 1.1% to about 0.1%, about 1.0% to about 0.1%, about 0.9% to about 0.1%, about 0.8% to about 0.1%, about 0.7% to about 0.1%, about 0.6% to about 0.1%, about 0.5% to about 0.1%, about 0.4% to about 0.1%, about 0.3% to about 0.1%, or about 0.2% to about 0.1% by weight after 0 months of storage.

In some embodiments, the impurity with a relative retention time of about 0.43 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 0 months of storage. In some embodiments, the impurity with a relative retention time of about 0.43 is less than about 1.5% by weight after 0 months of storage. In some embodiments, the impurity with a relative retention time of about 0.43 is less than about 1.4% by weight after 0 months of storage. In some embodiments, the impurity with a relative retention time of about 0.43 is less than about 1.3% by weight after 0 months of storage. In some embodiments, the impurity with a relative retention time of about 0.43 is less than about 1.2% by weight after 0 months of storage. In some embodiments, the impurity with a relative retention time of about 0.43 is less than about 1.1% by weight after 0 months of storage. In some embodiments, the impurity with a relative retention time of about 0.43 is less than about 1.0% by weight after 0 months of storage. In some embodiments, the impurity with a relative retention time of about 0.43 is less than about 0.9% by weight after 0 months of storage. In some embodiments, the impurity with a relative retention time of about 0.43 is less than about 0.8% by weight after 0 months of storage. In some embodiments, the impurity with a relative retention time of about 0.43 is less than about 0.7% by weight after 0 months of storage. In some embodiments, the impurity with a relative retention time of about 0.43 is less than about 0.6% by weight after 0 months of storage. In some embodiments, the impurity with a relative retention time of about 0.43 is less than about 0.5% by weight after 0 months of storage. In some embodiments, the impurity with a relative retention time of about 0.43 is less than about 0.4% by weight after 0 months of storage. In some embodiments, the impurity with a relative retention time of about 0.43 is less than about 0.3% by weight after 0 months of storage. In some embodiments, the impurity with a relative retention time of about 0.43 is less than about 0.2% by weight after 0 months of storage. In some embodiments, the impurity with a relative retention time of about 0.43 is less than about 0.1% by weight after 0 months of storage. In some embodiments, the impurity with a relative retention time of about 0.43 is less than about 0.09% by weight after 0 months of storage. In some embodiments, the impurity with a relative retention time of about 0.43 is less than about 0.08% by weight after 0 months of storage. In some embodiments, the impurity with a relative retention time of about 0.43 is less than about 0.07% by weight after 0 months of storage. In some embodiments, the impurity with a relative retention time of about 0.43 is less than about 0.06% by weight after 0 months of storage. In some embodiments, the impurity with a relative retention time of about 0.43 is less than about 0.05% by weight after 0 months of storage. In some embodiments, the impurity with a relative retention time of about 0.43 is less than about 0.04% by weight after 0 months of storage. In some embodiments, the impurity with a relative retention time of about 0.43 is less than about 0.03% by weight after 0 months of storage. In some embodiments, the impurity with a relative retention time of about 0.43 is less than about 0.02% by weight after 0 months of storage. In some embodiments, the impurity with a relative retention time of about 0.43 is less than about 0.01% by weight after 0 months of storage. In some embodiments, the impurity with a relative retention time of about 0.43 is less than about 0.005% by weight after 0 months of storage. In some embodiments, the impurity with a relative retention time of about 0.43 is less than about 0.001% by weight after 0 months of storage.

In some embodiments, the impurity with a relative retention time of about 0.43 is from less than about 1.5% to about 0.001%, less than about 1.4% to about 0.001%, less than about 1.3% to about 0.001%, less than about 1.2% to about 0.001%, less than about 1.1% to about 0.001%, less than about 1.0% to about 0.001%, less than about 0.9% to about 0.001%, less than about 0.8% to about 0.001%, less than about 0.7% to about 0.001%, less than about 0.6% to about 0.001%, less than about 0.5% to about 0.001%, less than about 0.4% to about 0.001%, less than about 0.3% to about 0.001%, less than about 0.2% to about 0.001%, less than about 0.1% to about 0.001%, less than about 0.09% to about 0.001%, less than about 0.08% to about 0.001%, less than about 0.07% to about 0.001%, less than about 0.06% to about 0.001%, less than about 0.05% to about 0.001%, less than about 0.04% to about 0.001%, less than about 0.03% to about 0.001%, less than about 0.02% to about 0.001%, less than about 0.01% to about 0.001%, or less than about 0.005% to about 0.001% by weight after 0 months of storage.

In some embodiments, the impurity with a relative retention time of about 0.43 is from less than about 1.5% to about 0.01%, less than about 1.4% to about 0.01%, less than about 1.3% to about 0.01%, less than about 1.2% to about 0.01%, less than about 1.1% to about 0.01%, less than about 1.0% to about 0.01%, less than about 0.9% to about 0.01%, less than about 0.8% to about 0.01%, less than about 0.7% to about 0.01%, less than about 0.6% to about 0.01%, less than about 0.5% to about 0.01%, less than about 0.4% to about 0.01%, less than about 0.3% to about 0.01%, less than about 0.2% to about 0.01%, less than about 0.1% to about 0.01%, less than about 0.09% to about 0.01%, less than about 0.08% to about 0.01%, less than about 0.07% to about 0.01%, less than about 0.06% to about 0.01%, less than about 0.05% to about 0.01%, less than about 0.04% to about 0.01%, less than about 0.03% to about 0.01%, or less than about 0.02% to about 0.01% by weight after 0 months of storage.

In some embodiments, the impurity with a relative retention time of about 0.43 is from less than about 1.5% to about 0.1%, less than about 1.4% to about 0.1%, less than about 1.3% to about 0.1%, less than about 1.2% to about 0.1%, less than about 1.1% to about 0.1%, less than about 1.0% to about 0.1%, less than about 0.9% to about 0.1%, less than about 0.8% to about 0.1%, less than about 0.7% to about 0.1%, less than about 0.6% to about 0.1%, less than about 0.5% to about 0.1%, less than about 0.4% to about 0.1%, less than about 0.3% to about 0.1%, or less than about 0.2% to about 0.1% by weight after 0 months of storage.

In some embodiments, the impurity with a relative retention time of about 0.43 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 12 months of storage. In some embodiments, the impurity with a relative retention time of about 0.43 is about 1.5% by weight after 12 months of storage. In some embodiments, the impurity with a relative retention time of about 0.43 is about 1.4% by weight after 12 months of storage. In some embodiments, the impurity with a relative retention time of about 0.43 is about 1.3% by weight after 12 months of storage. In some embodiments, the impurity with a relative retention time of about 0.43 is about 1.2% by weight after 12 months of storage. In some embodiments, the impurity with a relative retention time of about 0.43 is about 1.1% by weight after 12 months of storage. In some embodiments, the impurity with a relative retention time of about 0.43 is about 1.0% by weight after 12 months of storage. In some embodiments, the impurity with a relative retention time of about 0.43 is about 0.9% by weight after 12 months of storage. In some embodiments, the impurity with a relative retention time of about 0.43 is about 0.8% by weight after 12 months of storage. In some embodiments, the impurity with a relative retention time of about 0.43 is about 0.7% by weight after 12 months of storage. In some embodiments, the impurity with a relative retention time of about 0.43 is about 0.6% by weight after 12 months of storage. In some embodiments, the impurity with a relative retention time of about 0.43 is about 0.5% by weight after 12 months of storage. In some embodiments, the impurity with a relative retention time of about 0.43 is about 0.4% by weight after 12 months of storage. In some embodiments, the impurity with a relative retention time of about 0.43 is about 0.3% by weight after 12 months of storage. In some embodiments, the impurity with a relative retention time of about 0.43 is about 0.2% by weight after 12 months of storage. In some embodiments, the impurity with a relative retention time of about 0.43 is about 0.1% by weight after 12 months of storage. In some embodiments, the impurity with a relative retention time of about 0.43 is about 0.09% by weight after 12 months of storage. In some embodiments, the impurity with a relative retention time of about 0.43 is about 0.08% by weight after 12 months of storage. In some embodiments, the impurity with a relative retention time of about 0.43 is about 0.07% by weight after 12 months of storage. In some embodiments, the impurity with a relative retention time of about 0.43 is about 0.06% by weight after 12 months of storage. In some embodiments, the impurity with a relative retention time of about 0.43 is about 0.05% by weight after 12 months of storage. In some embodiments, the impurity with a relative retention time of about 0.43 is about 0.04% by weight after 12 months of storage. In some embodiments, the impurity with a relative retention time of about 0.43 is about 0.03% by weight after 12 months of storage. In some embodiments, the impurity with a relative retention time of about 0.43 is about 0.02% by weight after 12 months of storage. In some embodiments, the impurity with a relative retention time of about 0.43 is about 0.01% by weight after 12 months of storage. In some embodiments, the impurity with a relative retention time of about 0.43 is about 0.005% by weight after 12 months of storage. In some embodiments, the impurity with a relative retention time of about 0.43 is about 0.001% by weight after 12 months of storage.

In some embodiments, the impurity with a relative retention time of about 0.43 is from about 1.5% to about 0.001%, about 1.4% to about 0.001%, about 1.3% to about 0.001%, about 1.2% to about 0.001%, about 1.1% to about 0.001%, about 1.0% to about 0.001%, about 0.9% to about 0.001%, about 0.8% to about 0.001%, about 0.7% to about 0.001%, about 0.6% to about 0.001%, about 0.5% to about 0.001%, about 0.4% to about 0.001%, about 0.3% to about 0.001%, about 0.2% to about 0.001%, about 0.1% to about 0.001%, about 0.09% to about 0.001%, about 0.08% to about 0.001%, about 0.07% to about 0.001%, about 0.06% to about 0.001%, about 0.05% to about 0.001%, about 0.04% to about 0.001%, about 0.03% to about 0.001%, about 0.02% to about 0.001%, about 0.01% to about 0.001%, or about 0.005% to about 0.001% by weight after 12 months of storage.

In some embodiments, the impurity with a relative retention time of about 0.43 is from about 1.5% to about 0.01%, about 1.4% to about 0.01%, about 1.3% to about 0.01%, about 1.2% to about 0.01%, about 1.1% to about 0.01%, about 1.0% to about 0.01%, about 0.9% to about 0.01%, about 0.8% to about 0.01%, about 0.7% to about 0.01%, about 0.6% to about 0.01%, about 0.5% to about 0.01%, about 0.4% to about 0.01%, about 0.3% to about 0.01%, about 0.2% to about 0.01%, about 0.1% to about 0.01%, about 0.09% to about 0.01%, about 0.08% to about 0.01%, about 0.07% to about 0.01%, about 0.06% to about 0.01%, about 0.05% to about 0.01%, about 0.04% to about 0.01%, about 0.03% to about 0.01%, or about 0.02% to about 0.01% by weight after 12 months of storage.

In some embodiments, the impurity with a relative retention time of about 0.43 is from about 1.5% to about 0.1%, about 1.4% to about 0.1%, about 1.3% to about 0.1%, about 1.2% to about 0.1%, about 1.1% to about 0.1%, about 1.0% to about 0.1%, about 0.9% to about 0.1%, about 0.8% to about 0.1%, about 0.7% to about 0.1%, about 0.6% to about 0.1%, about 0.5% to about 0.1%, about 0.4% to about 0.1%, about 0.3% to about 0.1%, or about 0.2% to about 0.1% by weight after 12 months of storage.

In some embodiments, the impurity with a relative retention time of about 0.43 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 12 months of storage. In some embodiments, the impurity with a relative retention time of about 0.43 is less than about 1.5% by weight after 12 months of storage. In some embodiments, the impurity with a relative retention time of about 0.43 is less than about 1.4% by weight after 12 months of storage. In some embodiments, the impurity with a relative retention time of about 0.43 is less than about 1.3% by weight after 12 months of storage. In some embodiments, the impurity with a relative retention time of about 0.43 is less than about 1.2% by weight after 12 months of storage. In some embodiments, the impurity with a relative retention time of about 0.43 is less than about 1.1% by weight after 12 months of storage. In some embodiments, the impurity with a relative retention time of about 0.43 is less than about 1.0% by weight after 12 months of storage. In some embodiments, the impurity with a relative retention time of about 0.43 is less than about 0.9% by weight after 12 months of storage. In some embodiments, the impurity with a relative retention time of about 0.43 is less than about 0.8% by weight after 12 months of storage. In some embodiments, the impurity with a relative retention time of about 0.43 is less than about 0.7% by weight after 12 months of storage. In some embodiments, the impurity with a relative retention time of about 0.43 is less than about 0.6% by weight after 12 months of storage. In some embodiments, the impurity with a relative retention time of about 0.43 is less than about 0.5% by weight after 12 months of storage. In some embodiments, the impurity with a relative retention time of about 0.43 is less than about 0.4% by weight after 12 months of storage. In some embodiments, the impurity with a relative retention time of about 0.43 is less than about 0.3% by weight after 12 months of storage. In some embodiments, the impurity with a relative retention time of about 0.43 is less than about 0.2% by weight after 12 months of storage. In some embodiments, the impurity with a relative retention time of about 0.43 is less than about 0.1% by weight after 12 months of storage. In some embodiments, the impurity with a relative retention time of about 0.43 is less than about 0.09% by weight after 12 months of storage. In some embodiments, the impurity with a relative retention time of about 0.43 is less than about 0.08% by weight after 12 months of storage. In some embodiments, the impurity with a relative retention time of about 0.43 is less than about 0.07% by weight after 12 months of storage. In some embodiments, the impurity with a relative retention time of about 0.43 is less than about 0.06% by weight after 12 months of storage. In some embodiments, the impurity with a relative retention time of about 0.43 is less than about 0.05% by weight after 12 months of storage. In some embodiments, the impurity with a relative retention time of about 0.43 is less than about 0.04% by weight after 12 months of storage. In some embodiments, the impurity with a relative retention time of about 0.43 is less than about 0.03% by weight after 12 months of storage. In some embodiments, the impurity with a relative retention time of about 0.43 is less than about 0.02% by weight after 12 months of storage. In some embodiments, the impurity with a relative retention time of about 0.43 is less than about 0.01% by weight after 12 months of storage. In some embodiments, the impurity with a relative retention time of about 0.43 is less than about 0.005% by weight after 12 months of storage. In some embodiments, the impurity with a relative retention time of about 0.43 is less than about 0.001% by weight after 12 months of storage.

In some embodiments, the impurity with a relative retention time of about 0.43 is from less than about 1.5% to about 0.001%, less than about 1.4% to about 0.001%, less than about 1.3% to about 0.001%, less than about 1.2% to about 0.001%, less than about 1.1% to about 0.001%, less than about 1.0% to about 0.001%, less than about 0.9% to about 0.001%, less than about 0.8% to about 0.001%, less than about 0.7% to about 0.001%, less than about 0.6% to about 0.001%, less than about 0.5% to about 0.001%, less than about 0.4% to about 0.001%, less than about 0.3% to about 0.001%, less than about 0.2% to about 0.001%, less than about 0.1% to about 0.001%, less than about 0.09% to about 0.001%, less than about 0.08% to about 0.001%, less than about 0.07% to about 0.001%, less than about 0.06% to about 0.001%, less than about 0.05% to about 0.001%, less than about 0.04% to about 0.001%, less than about 0.03% to about 0.001%, less than about 0.02% to about 0.001%, less than about 0.01% to about 0.001%, or less than about 0.005% to about 0.001% by weight after 12 months of storage.

In some embodiments, the impurity with a relative retention time of about 0.43 is from less than about 1.5% to about 0.01%, less than about 1.4% to about 0.01%, less than about 1.3% to about 0.01%, less than about 1.2% to about 0.01%, less than about 1.1% to about 0.01%, less than about 1.0% to about 0.01%, less than about 0.9% to about 0.01%, less than about 0.8% to about 0.01%, less than about 0.7% to about 0.01%, less than about 0.6% to about 0.01%, less than about 0.5% to about 0.01%, less than about 0.4% to about 0.01%, less than about 0.3% to about 0.01%, less than about 0.2% to about 0.01%, less than about 0.1% to about 0.01%, less than about 0.09% to about 0.01%, less than about 0.08% to about 0.01%, less than about 0.07% to about 0.01%, less than about 0.06% to about 0.01%, less than about 0.05% to about 0.01%, less than about 0.04% to about 0.01%, less than about 0.03% to about 0.01%, or less than about 0.02% to about 0.01% by weight after 12 months of storage.

In some embodiments, the impurity with a relative retention time of about 0.43 is from less than about 1.5% to about 0.1%, less than about 1.4% to about 0.1%, less than about 1.3% to about 0.1%, less than about 1.2% to about 0.1%, less than about 1.1% to about 0.1%, less than about 1.0% to about 0.1%, less than about 0.9% to about 0.1%, less than about 0.8% to about 0.1%, less than about 0.7% to about 0.1%, less than about 0.6% to about 0.1%, less than about 0.5% to about 0.1%, less than about 0.4% to about 0.1%, less than about 0.3% to about 0.1%, or less than about 0.2% to about 0.1% by weight after 12 months of storage.

In some embodiments, the impurity with a relative retention time of about 0.43 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 18 months of storage. In some embodiments, the impurity with a relative retention time of about 0.43 is about 1.5% by weight after 18 months of storage. In some embodiments, the impurity with a relative retention time of about 0.43 is about 1.4% by weight after 18 months of storage. In some embodiments, the impurity with a relative retention time of about 0.43 is about 1.3% by weight after 18 months of storage. In some embodiments, the impurity with a relative retention time of about 0.43 is about 1.2% by weight after 18 months of storage. In some embodiments, the impurity with a relative retention time of about 0.43 is about 1.1% by weight after 18 months of storage. In some embodiments, the impurity with a relative retention time of about 0.43 is about 1.0% by weight after 18 months of storage. In some embodiments, the impurity with a relative retention time of about 0.43 is about 0.9% by weight after 18 months of storage. In some embodiments, the impurity with a relative retention time of about 0.43 is about 0.8% by weight after 18 months of storage. In some embodiments, the impurity with a relative retention time of about 0.43 is about 0.7% by weight after 18 months of storage. In some embodiments, the impurity with a relative retention time of about 0.43 is about 0.6% by weight after 18 months of storage. In some embodiments, the impurity with a relative retention time of about 0.43 is about 0.5% by weight after 18 months of storage. In some embodiments, the impurity with a relative retention time of about 0.43 is about 0.4% by weight after 18 months of storage. In some embodiments, the impurity with a relative retention time of about 0.43 is about 0.3% by weight after 18 months of storage. In some embodiments, the impurity with a relative retention time of about 0.43 is about 0.2% by weight after 18 months of storage. In some embodiments, the impurity with a relative retention time of about 0.43 is about 0.1% by weight after 18 months of storage. In some embodiments, the impurity with a relative retention time of about 0.43 is about 0.09% by weight after 18 months of storage. In some embodiments, the impurity with a relative retention time of about 0.43 is about 0.08% by weight after 18 months of storage. In some embodiments, the impurity with a relative retention time of about 0.43 is about 0.07% by weight after 18 months of storage. In some embodiments, the impurity with a relative retention time of about 0.43 is about 0.06% by weight after 18 months of storage. In some embodiments, the impurity with a relative retention time of about 0.43 is about 0.05% by weight after 18 months of storage. In some embodiments, the impurity with a relative retention time of about 0.43 is about 0.04% by weight after 18 months of storage. In some embodiments, the impurity with a relative retention time of about 0.43 is about 0.03% by weight after 18 months of storage. In some embodiments, the impurity with a relative retention time of about 0.43 is about 0.02% by weight after 18 months of storage. In some embodiments, the impurity with a relative retention time of about 0.43 is about 0.01% by weight after 18 months of storage. In some embodiments, the impurity with a relative retention time of about 0.43 is about 0.005% by weight after 18 months of storage. In some embodiments, the impurity with a relative retention time of about 0.43 is about 0.001% by weight after 18 months of storage.

In some embodiments, the impurity with a relative retention time of about 0.43 is from about 1.5% to about 0.001%, about 1.4% to about 0.001%, about 1.3% to about 0.001%, about 1.2% to about 0.001%, about 1.1% to about 0.001%, about 1.0% to about 0.001%, about 0.9% to about 0.001%, about 0.8% to about 0.001%, about 0.7% to about 0.001%, about 0.6% to about 0.001%, about 0.5% to about 0.001%, about 0.4% to about 0.001%, about 0.3% to about 0.001%, about 0.2% to about 0.001%, about 0.1% to about 0.001%, about 0.09% to about 0.001%, about 0.08% to about 0.001%, about 0.07% to about 0.001%, about 0.06% to about 0.001%, about 0.05% to about 0.001%, about 0.04% to about 0.001%, about 0.03% to about 0.001%, about 0.02% to about 0.001%, about 0.01% to about 0.001%, or about 0.005% to about 0.001% by weight after 18 months of storage.

In some embodiments, the impurity with a relative retention time of about 0.43 is from about 1.5% to about 0.01%, about 1.4% to about 0.01%, about 1.3% to about 0.01%, about 1.2% to about 0.01%, about 1.1% to about 0.01%, about 1.0% to about 0.01%, about 0.9% to about 0.01%, about 0.8% to about 0.01%, about 0.7% to about 0.01%, about 0.6% to about 0.01%, about 0.5% to about 0.01%, about 0.4% to about 0.01%, about 0.3% to about 0.01%, about 0.2% to about 0.01%, about 0.1% to about 0.01%, about 0.09% to about 0.01%, about 0.08% to about 0.01%, about 0.07% to about 0.01%, about 0.06% to about 0.01%, about 0.05% to about 0.01%, about 0.04% to about 0.01%, about 0.03% to about 0.01%, or about 0.02% to about 0.01% by weight after 18 months of storage.

In some embodiments, the impurity with a relative retention time of about 0.43 is from about 1.5% to about 0.1%, about 1.4% to about 0.1%, about 1.3% to about 0.1%, about 1.2% to about 0.1%, about 1.1% to about 0.1%, about 1.0% to about 0.1%, about 0.9% to about 0.1%, about 0.8% to about 0.1%, about 0.7% to about 0.1%, about 0.6% to about 0.1%, about 0.5% to about 0.1%, about 0.4% to about 0.1%, about 0.3% to about 0.1%, or about 0.2% to about 0.1% by weight after 18 months of storage.

In some embodiments, the impurity with a relative retention time of about 0.43 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 18 months of storage. In some embodiments, the impurity with a relative retention time of about 0.43 is less than about 1.5% by weight after 18 months of storage. In some embodiments, the impurity with a relative retention time of about 0.43 is less than about 1.4% by weight after 18 months of storage. In some embodiments, the impurity with a relative retention time of about 0.43 is less than about 1.3% by weight after 18 months of storage. In some embodiments, the impurity with a relative retention time of about 0.43 is less than about 1.2% by weight after 18 months of storage. In some embodiments, the impurity with a relative retention time of about 0.43 is less than about 1.1% by weight after 18 months of storage. In some embodiments, the impurity with a relative retention time of about 0.43 is less than about 1.0% by weight after 18 months of storage. In some embodiments, the impurity with a relative retention time of about 0.43 is less than about 0.9% by weight after 18 months of storage. In some embodiments, the impurity with a relative retention time of about 0.43 is less than about 0.8% by weight after 18 months of storage. In some embodiments, the impurity with a relative retention time of about 0.43 is less than about 0.7% by weight after 18 months of storage. In some embodiments, the impurity with a relative retention time of about 0.43 is less than about 0.6% by weight after 18 months of storage. In some embodiments, the impurity with a relative retention time of about 0.43 is less than about 0.5% by weight after 18 months of storage. In some embodiments, the impurity with a relative retention time of about 0.43 is less than about 0.4% by weight after 18 months of storage. In some embodiments, the impurity with a relative retention time of about 0.43 is less than about 0.3% by weight after 18 months of storage. In some embodiments, the impurity with a relative retention time of about 0.43 is less than about 0.2% by weight after 18 months of storage. In some embodiments, the impurity with a relative retention time of about 0.43 is less than about 0.1% by weight after 18 months of storage. In some embodiments, the impurity with a relative retention time of about 0.43 is less than about 0.09% by weight after 18 months of storage. In some embodiments, the impurity with a relative retention time of about 0.43 is less than about 0.08% by weight after 18 months of storage. In some embodiments, the impurity with a relative retention time of about 0.43 is less than about 0.07% by weight after 18 months of storage. In some embodiments, the impurity with a relative retention time of about 0.43 is less than about 0.06% by weight after 18 months of storage. In some embodiments, the impurity with a relative retention time of about 0.43 is less than about 0.05% by weight after 18 months of storage. In some embodiments, the impurity with a relative retention time of about 0.43 is less than about 0.04% by weight after 18 months of storage. In some embodiments, the impurity with a relative retention time of about 0.43 is less than about 0.03% by weight after 18 months of storage. In some embodiments, the impurity with a relative retention time of about 0.43 is less than about 0.02% by weight after 18 months of storage. In some embodiments, the impurity with a relative retention time of about 0.43 is less than about 0.01% by weight after 18 months of storage. In some embodiments, the impurity with a relative retention time of about 0.43 is less than about 0.005% by weight after 18 months of storage. In some embodiments, the impurity with a relative retention time of about 0.43 is less than about 0.001% by weight after 18 months of storage.

In some embodiments, the impurity with a relative retention time of about 0.43 is from less than about 1.5% to about 0.001%, less than about 1.4% to about 0.001%, less than about 1.3% to about 0.001%, less than about 1.2% to about 0.001%, less than about 1.1% to about 0.001%, less than about 1.0% to about 0.001%, less than about 0.9% to about 0.001%, less than about 0.8% to about 0.001%, less than about 0.7% to about 0.001%, less than about 0.6% to about 0.001%, less than about 0.5% to about 0.001%, less than about 0.4% to about 0.001%, less than about 0.3% to about 0.001%, less than about 0.2% to about 0.001%, less than about 0.1% to about 0.001%, less than about 0.09% to about 0.001%, less than about 0.08% to about 0.001%, less than about 0.07% to about 0.001%, less than about 0.06% to about 0.001%, less than about 0.05% to about 0.001%, less than about 0.04% to about 0.001%, less than about 0.03% to about 0.001%, less than about 0.02% to about 0.001%, less than about 0.01% to about 0.001%, or less than about 0.005% to about 0.001% by weight after 18 months of storage.

In some embodiments, the impurity with a relative retention time of about 0.43 is from less than about 1.5% to about 0.01%, less than about 1.4% to about 0.01%, less than about 1.3% to about 0.01%, less than about 1.2% to about 0.01%, less than about 1.1% to about 0.01%, less than about 1.0% to about 0.01%, less than about 0.9% to about 0.01%, less than about 0.8% to about 0.01%, less than about 0.7% to about 0.01%, less than about 0.6% to about 0.01%, less than about 0.5% to about 0.01%, less than about 0.4% to about 0.01%, less than about 0.3% to about 0.01%, less than about 0.2% to about 0.01%, less than about 0.1% to about 0.01%, less than about 0.09% to about 0.01%, less than about 0.08% to about 0.01%, less than about 0.07% to about 0.01%, less than about 0.06% to about 0.01%, less than about 0.05% to about 0.01%, less than about 0.04% to about 0.01%, less than about 0.03% to about 0.01%, or less than about 0.02% to about 0.01% by weight after 18 months of storage.

In some embodiments, the impurity with a relative retention time of about 0.43 is from less than about 1.5% to about 0.1%, less than about 1.4% to about 0.1%, less than about 1.3% to about 0.1%, less than about 1.2% to about 0.1%, less than about 1.1% to about 0.1%, less than about 1.0% to about 0.1%, less than about 0.9% to about 0.1%, less than about 0.8% to about 0.1%, less than about 0.7% to about 0.1%, less than about 0.6% to about 0.1%, less than about 0.5% to about 0.1%, less than about 0.4% to about 0.1%, less than about 0.3% to about 0.1%, or less than about 0.2% to about 0.1% by weight after 18 months of storage.

In some embodiments, the total impurity comprises an impurity with a relative retention time of about 0.68. In some embodiments, the total impurity comprises an impurity with a relative retention time of about 0.68±0.01, about 0.68±0.02, about 0.68±0.03, about 0.68±0.04, about 0.68±0.05, about 0.68±0.06, about 0.68±0.07, about 0.68±0.08, about 0.68±0.09, or about 0.68±0.10.

In some embodiments, the impurity with a relative retention time of about 0.68 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight. In some embodiments, the impurity with a relative retention time of about 0.68 is about 1.5% by weight. In some embodiments, the impurity with a relative retention time of about 0.68 is about 1.4% by weight. In some embodiments, the impurity with a relative retention time of about 0.68 is about 1.3% by weight. In some embodiments, the impurity with a relative retention time of about 0.68 is about 1.2% by weight. In some embodiments, the impurity with a relative retention time of about 0.68 is about 1.1% by weight. In some embodiments, the impurity with a relative retention time of about 0.68 is about 1.0% by weight. In some embodiments, the impurity with a relative retention time of about 0.68 is about 0.9% by weight. In some embodiments, the impurity with a relative retention time of about 0.68 is about 0.8% by weight. In some embodiments, the impurity with a relative retention time of about 0.68 is about 0.7% by weight. In some embodiments, the impurity with a relative retention time of about 0.68 is about 0.6% by weight. In some embodiments, the impurity with a relative retention time of about 0.68 is about 0.5% by weight. In some embodiments, the impurity with a relative retention time of about 0.68 is about 0.4% by weight. In some embodiments, the impurity with a relative retention time of about 0.68 is about 0.3% by weight. In some embodiments, the impurity with a relative retention time of about 0.68 is about 0.2% by weight. In some embodiments, the impurity with a relative retention time of about 0.68 is about 0.1% by weight. In some embodiments, the impurity with a relative retention time of about 0.68 is about 0.09% by weight. In some embodiments, the impurity with a relative retention time of about 0.68 is about 0.08% by weight. In some embodiments, the impurity with a relative retention time of about 0.68 is about 0.07% by weight. In some embodiments, the impurity with a relative retention time of about 0.68 is about 0.06% by weight. In some embodiments, the impurity with a relative retention time of about 0.68 is about 0.05% by weight. In some embodiments, the impurity with a relative retention time of about 0.68 is about 0.04% by weight. In some embodiments, the impurity with a relative retention time of about 0.68 is about 0.03% by weight. In some embodiments, the impurity with a relative retention time of about 0.68 is about 0.02% by weight. In some embodiments, the impurity with a relative retention time of about 0.68 is about 0.01% by weight. In some embodiments, the impurity with a relative retention time of about 0.68 is about 0.005% by weight. In some embodiments, the impurity with a relative retention time of about 0.68 is about 0.001% by weight.

In some embodiments, the impurity with a relative retention time of about 0.68 is from about 1.5% to about 0.001%, about 1.4% to about 0.001%, about 1.3% to about 0.001%, about 1.2% to about 0.001%, about 1.1% to about 0.001%, about 1.0% to about 0.001%, about 0.9% to about 0.001%, about 0.8% to about 0.001%, about 0.7% to about 0.001%, about 0.6% to about 0.001%, about 0.5% to about 0.001%, about 0.4% to about 0.001%, about 0.3% to about 0.001%, about 0.2% to about 0.001%, about 0.1% to about 0.001%, about 0.09% to about 0.001%, about 0.08% to about 0.001%, about 0.07% to about 0.001%, about 0.06% to about 0.001%, about 0.05% to about 0.001%, about 0.04% to about 0.001%, about 0.03% to about 0.001%, about 0.02% to about 0.001%, about 0.01% to about 0.001%, or about 0.005% to about 0.001% by weight.

In some embodiments, the impurity with a relative retention time of about 0.68 is from about 1.5% to about 0.01%, about 1.4% to about 0.01%, about 1.3% to about 0.01%, about 1.2% to about 0.01%, about 1.1% to about 0.01%, about 1.0% to about 0.01%, about 0.9% to about 0.01%, about 0.8% to about 0.01%, about 0.7% to about 0.01%, about 0.6% to about 0.01%, about 0.5% to about 0.01%, about 0.4% to about 0.01%, about 0.3% to about 0.01%, about 0.2% to about 0.01%, about 0.1% to about 0.01%, about 0.09% to about 0.01%, about 0.08% to about 0.01%, about 0.07% to about 0.01%, about 0.06% to about 0.01%, about 0.05% to about 0.01%, about 0.04% to about 0.01%, about 0.03% to about 0.01%, or about 0.02% to about 0.01% by weight.

In some embodiments, the impurity with a relative retention time of about 0.68 is from about 1.5% to about 0.1%, about 1.4% to about 0.1%, about 1.3% to about 0.1%, about 1.2% to about 0.1%, about 1.1% to about 0.1%, about 1.0% to about 0.1%, about 0.9% to about 0.1%, about 0.8% to about 0.1%, about 0.7% to about 0.1%, about 0.6% to about 0.1%, about 0.5% to about 0.1%, about 0.4% to about 0.1%, about 0.3% to about 0.1%, or about 0.2% to about 0.1% by weight.

In some embodiments, the impurity with a relative retention time of about 0.68 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight. In some embodiments, the impurity with a relative retention time of about 0.68 is less than about 1.5% by weight. In some embodiments, the impurity with a relative retention time of about 0.68 is less than about 1.4% by weight. In some embodiments, the impurity with a relative retention time of about 0.68 is less than about 1.3% by weight. In some embodiments, the impurity with a relative retention time of about 0.68 is less than about 1.2% by weight. In some embodiments, the impurity with a relative retention time of about 0.68 is less than about 1.1% by weight. In some embodiments, the impurity with a relative retention time of about 0.68 is less than about 1.0% by weight. In some embodiments, the impurity with a relative retention time of about 0.68 is less than about 0.9% by weight. In some embodiments, the impurity with a relative retention time of about 0.68 is less than about 0.8% by weight. In some embodiments, the impurity with a relative retention time of about 0.68 is less than about 0.7% by weight. In some embodiments, the impurity with a relative retention time of about 0.68 is less than about 0.6% by weight. In some embodiments, the impurity with a relative retention time of about 0.68 is less than about 0.5% by weight. In some embodiments, the impurity with a relative retention time of about 0.68 is less than about 0.4% by weight. In some embodiments, the impurity with a relative retention time of about 0.68 is less than about 0.3% by weight. In some embodiments, the impurity with a relative retention time of about 0.68 is less than about 0.2% by weight. In some embodiments, the impurity with a relative retention time of about 0.68 is less than about 0.1% by weight. In some embodiments, the impurity with a relative retention time of about 0.68 is less than about 0.09% by weight. In some embodiments, the impurity with a relative retention time of about 0.68 is less than about 0.08% by weight. In some embodiments, the impurity with a relative retention time of about 0.68 is less than about 0.07% by weight. In some embodiments, the impurity with a relative retention time of about 0.68 is less than about 0.06% by weight. In some embodiments, the impurity with a relative retention time of about 0.68 is less than about 0.05% by weight. In some embodiments, the impurity with a relative retention time of about 0.68 is less than about 0.04% by weight. In some embodiments, the impurity with a relative retention time of about 0.68 is less than about 0.03% by weight. In some embodiments, the impurity with a relative retention time of about 0.68 is less than about 0.02% by weight. In some embodiments, the impurity with a relative retention time of about 0.68 is less than about 0.01% by weight. In some embodiments, the impurity with a relative retention time of about 0.68 is less than about 0.005% by weight. In some embodiments, the impurity with a relative retention time of about 0.68 is less than about 0.001% by weight.

In some embodiments, the impurity with a relative retention time of about 0.68 is from less than about 1.5% to about 0.001%, less than about 1.4% to about 0.001%, less than about 1.3% to about 0.001%, less than about 1.2% to about 0.001%, less than about 1.1% to about 0.001%, less than about 1.0% to about 0.001%, less than about 0.9% to about 0.001%, less than about 0.8% to about 0.001%, less than about 0.7% to about 0.001%, less than about 0.6% to about 0.001%, less than about 0.5% to about 0.001%, less than about 0.4% to about 0.001%, less than about 0.3% to about 0.001%, less than about 0.2% to about 0.001%, less than about 0.1% to about 0.001%, less than about 0.09% to about 0.001%, less than about 0.08% to about 0.001%, less than about 0.07% to about 0.001%, less than about 0.06% to about 0.001%, less than about 0.05% to about 0.001%, less than about 0.04% to about 0.001%, less than about 0.03% to about 0.001%, less than about 0.02% to about 0.001%, less than about 0.01% to about 0.001%, or less than about 0.005% to about 0.001% by weight.

In some embodiments, the impurity with a relative retention time of about 0.68 is from less than about 1.5% to about 0.01%, less than about 1.4% to about 0.01%, less than about 1.3% to about 0.01%, less than about 1.2% to about 0.01%, less than about 1.1% to about 0.01%, less than about 1.0% to about 0.01%, less than about 0.9% to about 0.01%, less than about 0.8% to about 0.01%, less than about 0.7% to about 0.01%, less than about 0.6% to about 0.01%, less than about 0.5% to about 0.01%, less than about 0.4% to about 0.01%, less than about 0.3% to about 0.01%, less than about 0.2% to about 0.01%, less than about 0.1% to about 0.01%, less than about 0.09% to about 0.01%, less than about 0.08% to about 0.01%, less than about 0.07% to about 0.01%, less than about 0.06% to about 0.01%, less than about 0.05% to about 0.01%, less than about 0.04% to about 0.01%, less than about 0.03% to about 0.01%, or less than about 0.02% to about 0.01% by weight.

In some embodiments, the impurity with a relative retention time of about 0.68 is from less than about 1.5% to about 0.1%, less than about 1.4% to about 0.1%, less than about 1.3% to about 0.1%, less than about 1.2% to about 0.1%, less than about 1.1% to about 0.1%, less than about 1.0% to about 0.1%, less than about 0.9% to about 0.1%, less than about 0.8% to about 0.1%, less than about 0.7% to about 0.1%, less than about 0.6% to about 0.1%, less than about 0.5% to about 0.1%, less than about 0.4% to about 0.1%, less than about 0.3% to about 0.1%, or less than about 0.2% to about 0.1% by weight.

In some embodiments, the impurity with a relative retention time of about 0.68 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 0 months of storage. In some embodiments, the impurity with a relative retention time of about 0.68 is about 1.5% by weight after 0 months of storage. In some embodiments, the impurity with a relative retention time of about 0.68 is about 1.4% by weight after 0 months of storage. In some embodiments, the impurity with a relative retention time of about 0.68 is about 1.3% by weight after 0 months of storage. In some embodiments, the impurity with a relative retention time of about 0.68 is about 1.2% by weight after 0 months of storage. In some embodiments, the impurity with a relative retention time of about 0.68 is about 1.1% by weight after 0 months of storage. In some embodiments, the impurity with a relative retention time of about 0.68 is about 1.0% by weight after 0 months of storage. In some embodiments, the impurity with a relative retention time of about 0.68 is about 0.9% by weight after 0 months of storage. In some embodiments, the impurity with a relative retention time of about 0.68 is about 0.8% by weight after 0 months of storage. In some embodiments, the impurity with a relative retention time of about 0.68 is about 0.7% by weight after 0 months of storage. In some embodiments, the impurity with a relative retention time of about 0.68 is about 0.6% by weight after 0 months of storage. In some embodiments, the impurity with a relative retention time of about 0.68 is about 0.5% by weight after 0 months of storage. In some embodiments, the impurity with a relative retention time of about 0.68 is about 0.4% by weight after 0 months of storage. In some embodiments, the impurity with a relative retention time of about 0.68 is about 0.3% by weight after 0 months of storage. In some embodiments, the impurity with a relative retention time of about 0.68 is about 0.2% by weight after 0 months of storage. In some embodiments, the impurity with a relative retention time of about 0.68 is about 0.1% by weight after 0 months of storage. In some embodiments, the impurity with a relative retention time of about 0.68 is about 0.09% by weight after 0 months of storage. In some embodiments, the impurity with a relative retention time of about 0.68 is about 0.08% by weight after 0 months of storage. In some embodiments, the impurity with a relative retention time of about 0.68 is about 0.07% by weight after 0 months of storage. In some embodiments, the impurity with a relative retention time of about 0.68 is about 0.06% by weight after 0 months of storage. In some embodiments, the impurity with a relative retention time of about 0.68 is about 0.05% by weight after 0 months of storage. In some embodiments, the impurity with a relative retention time of about 0.68 is about 0.04% by weight after 0 months of storage. In some embodiments, the impurity with a relative retention time of about 0.68 is about 0.03% by weight after 0 months of storage. In some embodiments, the impurity with a relative retention time of about 0.68 is about 0.02% by weight after 0 months of storage. In some embodiments, the impurity with a relative retention time of about 0.68 is about 0.01% by weight after 0 months of storage. In some embodiments, the impurity with a relative retention time of about 0.68 is about 0.005% by weight after 0 months of storage. In some embodiments, the impurity with a relative retention time of about 0.68 is about 0.001% by weight after 0 months of storage.

In some embodiments, the impurity with a relative retention time of about 0.68 is from about 1.5% to about 0.001%, about 1.4% to about 0.001%, about 1.3% to about 0.001%, about 1.2% to about 0.001%, about 1.1% to about 0.001%, about 1.0% to about 0.001%, about 0.9% to about 0.001%, about 0.8% to about 0.001%, about 0.7% to about 0.001%, about 0.6% to about 0.001%, about 0.5% to about 0.001%, about 0.4% to about 0.001%, about 0.3% to about 0.001%, about 0.2% to about 0.001%, about 0.1% to about 0.001%, about 0.09% to about 0.001%, about 0.08% to about 0.001%, about 0.07% to about 0.001%, about 0.06% to about 0.001%, about 0.05% to about 0.001%, about 0.04% to about 0.001%, about 0.03% to about 0.001%, about 0.02% to about 0.001%, about 0.01% to about 0.001%, or about 0.005% to about 0.001% by weight after 0 months of storage.

In some embodiments, the impurity with a relative retention time of about 0.68 is from about 1.5% to about 0.01%, about 1.4% to about 0.01%, about 1.3% to about 0.01%, about 1.2% to about 0.01%, about 1.1% to about 0.01%, about 1.0% to about 0.01%, about 0.9% to about 0.01%, about 0.8% to about 0.01%, about 0.7% to about 0.01%, about 0.6% to about 0.01%, about 0.5% to about 0.01%, about 0.4% to about 0.01%, about 0.3% to about 0.01%, about 0.2% to about 0.01%, about 0.1% to about 0.01%, about 0.09% to about 0.01%, about 0.08% to about 0.01%, about 0.07% to about 0.01%, about 0.06% to about 0.01%, about 0.05% to about 0.01%, about 0.04% to about 0.01%, about 0.03% to about 0.01%, or about 0.02% to about 0.01% by weight after 0 months of storage.

In some embodiments, the impurity with a relative retention time of about 0.68 is from about 1.5% to about 0.1%, about 1.4% to about 0.1%, about 1.3% to about 0.1%, about 1.2% to about 0.1%, about 1.1% to about 0.1%, about 1.0% to about 0.1%, about 0.9% to about 0.1%, about 0.8% to about 0.1%, about 0.7% to about 0.1%, about 0.6% to about 0.1%, about 0.5% to about 0.1%, about 0.4% to about 0.1%, about 0.3% to about 0.1%, or about 0.2% to about 0.1% by weight after 0 months of storage.

In some embodiments, the impurity with a relative retention time of about 0.68 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 0 months of storage. In some embodiments, the impurity with a relative retention time of about 0.68 is less than about 1.5% by weight after 0 months of storage. In some embodiments, the impurity with a relative retention time of about 0.68 is less than about 1.4% by weight after 0 months of storage. In some embodiments, the impurity with a relative retention time of about 0.68 is less than about 1.3% by weight after 0 months of storage. In some embodiments, the impurity with a relative retention time of about 0.68 is less than about 1.2% by weight after 0 months of storage. In some embodiments, the impurity with a relative retention time of about 0.68 is less than about 1.1% by weight after 0 months of storage. In some embodiments, the impurity with a relative retention time of about 0.68 is less than about 1.0% by weight after 0 months of storage. In some embodiments, the impurity with a relative retention time of about 0.68 is less than about 0.9% by weight after 0 months of storage. In some embodiments, the impurity with a relative retention time of about 0.68 is less than about 0.8% by weight after 0 months of storage. In some embodiments, the impurity with a relative retention time of about 0.68 is less than about 0.7% by weight after 0 months of storage. In some embodiments, the impurity with a relative retention time of about 0.68 is less than about 0.6% by weight after 0 months of storage. In some embodiments, the impurity with a relative retention time of about 0.68 is less than about 0.5% by weight after 0 months of storage. In some embodiments, the impurity with a relative retention time of about 0.68 is less than about 0.4% by weight after 0 months of storage. In some embodiments, the impurity with a relative retention time of about 0.68 is less than about 0.3% by weight after 0 months of storage. In some embodiments, the impurity with a relative retention time of about 0.68 is less than about 0.2% by weight after 0 months of storage. In some embodiments, the impurity with a relative retention time of about 0.68 is less than about 0.1% by weight after 0 months of storage. In some embodiments, the impurity with a relative retention time of about 0.68 is less than about 0.09% by weight after 0 months of storage. In some embodiments, the impurity with a relative retention time of about 0.68 is less than about 0.08% by weight after 0 months of storage. In some embodiments, the impurity with a relative retention time of about 0.68 is less than about 0.07% by weight after 0 months of storage. In some embodiments, the impurity with a relative retention time of about 0.68 is less than about 0.06% by weight after 0 months of storage. In some embodiments, the impurity with a relative retention time of about 0.68 is less than about 0.05% by weight after 0 months of storage. In some embodiments, the impurity with a relative retention time of about 0.68 is less than about 0.04% by weight after 0 months of storage. In some embodiments, the impurity with a relative retention time of about 0.68 is less than about 0.03% by weight after 0 months of storage. In some embodiments, the impurity with a relative retention time of about 0.68 is less than about 0.02% by weight after 0 months of storage. In some embodiments, the impurity with a relative retention time of about 0.68 is less than about 0.01% by weight after 0 months of storage. In some embodiments, the impurity with a relative retention time of about 0.68 is less than about 0.005% by weight after 0 months of storage. In some embodiments, the impurity with a relative retention time of about 0.68 is less than about 0.001% by weight after 0 months of storage.

In some embodiments, the impurity with a relative retention time of about 0.68 is from less than about 1.5% to about 0.001%, less than about 1.4% to about 0.001%, less than about 1.3% to about 0.001%, less than about 1.2% to about 0.001%, less than about 1.1% to about 0.001%, less than about 1.0% to about 0.001%, less than about 0.9% to about 0.001%, less than about 0.8% to about 0.001%, less than about 0.7% to about 0.001%, less than about 0.6% to about 0.001%, less than about 0.5% to about 0.001%, less than about 0.4% to about 0.001%, less than about 0.3% to about 0.001%, less than about 0.2% to about 0.001%, less than about 0.1% to about 0.001%, less than about 0.09% to about 0.001%, less than about 0.08% to about 0.001%, less than about 0.07% to about 0.001%, less than about 0.06% to about 0.001%, less than about 0.05% to about 0.001%, less than about 0.04% to about 0.001%, less than about 0.03% to about 0.001%, less than about 0.02% to about 0.001%, less than about 0.01% to about 0.001%, or less than about 0.005% to about 0.001% by weight after 0 months of storage.

In some embodiments, the impurity with a relative retention time of about 0.68 is from less than about 1.5% to about 0.01%, less than about 1.4% to about 0.01%, less than about 1.3% to about 0.01%, less than about 1.2% to about 0.01%, less than about 1.1% to about 0.01%, less than about 1.0% to about 0.01%, less than about 0.9% to about 0.01%, less than about 0.8% to about 0.01%, less than about 0.7% to about 0.01%, less than about 0.6% to about 0.01%, less than about 0.5% to about 0.01%, less than about 0.4% to about 0.01%, less than about 0.3% to about 0.01%, less than about 0.2% to about 0.01%, less than about 0.1% to about 0.01%, less than about 0.09% to about 0.01%, less than about 0.08% to about 0.01%, less than about 0.07% to about 0.01%, less than about 0.06% to about 0.01%, less than about 0.05% to about 0.01%, less than about 0.04% to about 0.01%, less than about 0.03% to about 0.01%, or less than about 0.02% to about 0.01% by weight after 0 months of storage.

In some embodiments, the impurity with a relative retention time of about 0.68 is from less than about 1.5% to about 0.1%, less than about 1.4% to about 0.1%, less than about 1.3% to about 0.1%, less than about 1.2% to about 0.1%, less than about 1.1% to about 0.1%, less than about 1.0% to about 0.1%, less than about 0.9% to about 0.1%, less than about 0.8% to about 0.1%, less than about 0.7% to about 0.1%, less than about 0.6% to about 0.1%, less than about 0.5% to about 0.1%, less than about 0.4% to about 0.1%, less than about 0.3% to about 0.1%, or less than about 0.2% to about 0.1% by weight after 0 months of storage.

In some embodiments, the impurity with a relative retention time of about 0.68 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 12 months of storage. In some embodiments, the impurity with a relative retention time of about 0.68 is about 1.5% by weight after 12 months of storage. In some embodiments, the impurity with a relative retention time of about 0.68 is about 1.4% by weight after 12 months of storage. In some embodiments, the impurity with a relative retention time of about 0.68 is about 1.3% by weight after 12 months of storage. In some embodiments, the impurity with a relative retention time of about 0.68 is about 1.2% by weight after 12 months of storage. In some embodiments, the impurity with a relative retention time of about 0.68 is about 1.1% by weight after 12 months of storage. In some embodiments, the impurity with a relative retention time of about 0.68 is about 1.0% by weight after 12 months of storage. In some embodiments, the impurity with a relative retention time of about 0.68 is about 0.9% by weight after 12 months of storage. In some embodiments, the impurity with a relative retention time of about 0.68 is about 0.8% by weight after 12 months of storage. In some embodiments, the impurity with a relative retention time of about 0.68 is about 0.7% by weight after 12 months of storage. In some embodiments, the impurity with a relative retention time of about 0.68 is about 0.6% by weight after 12 months of storage. In some embodiments, the impurity with a relative retention time of about 0.68 is about 0.5% by weight after 12 months of storage. In some embodiments, the impurity with a relative retention time of about 0.68 is about 0.4% by weight after 12 months of storage. In some embodiments, the impurity with a relative retention time of about 0.68 is about 0.3% by weight after 12 months of storage. In some embodiments, the impurity with a relative retention time of about 0.68 is about 0.2% by weight after 12 months of storage. In some embodiments, the impurity with a relative retention time of about 0.68 is about 0.1% by weight after 12 months of storage. In some embodiments, the impurity with a relative retention time of about 0.68 is about 0.09% by weight after 12 months of storage. In some embodiments, the impurity with a relative retention time of about 0.68 is about 0.08% by weight after 12 months of storage. In some embodiments, the impurity with a relative retention time of about 0.68 is about 0.07% by weight after 12 months of storage. In some embodiments, the impurity with a relative retention time of about 0.68 is about 0.06% by weight after 12 months of storage. In some embodiments, the impurity with a relative retention time of about 0.68 is about 0.05% by weight after 12 months of storage. In some embodiments, the impurity with a relative retention time of about 0.68 is about 0.04% by weight after 12 months of storage. In some embodiments, the impurity with a relative retention time of about 0.68 is about 0.03% by weight after 12 months of storage. In some embodiments, the impurity with a relative retention time of about 0.68 is about 0.02% by weight after 12 months of storage. In some embodiments, the impurity with a relative retention time of about 0.68 is about 0.01% by weight after 12 months of storage. In some embodiments, the impurity with a relative retention time of about 0.68 is about 0.005% by weight after 12 months of storage. In some embodiments, the impurity with a relative retention time of about 0.68 is about 0.001% by weight after 12 months of storage.

In some embodiments, the impurity with a relative retention time of about 0.68 is from about 1.5% to about 0.001%, about 1.4% to about 0.001%, about 1.3% to about 0.001%, about 1.2% to about 0.001%, about 1.1% to about 0.001%, about 1.0% to about 0.001%, about 0.9% to about 0.001%, about 0.8% to about 0.001%, about 0.7% to about 0.001%, about 0.6% to about 0.001%, about 0.5% to about 0.001%, about 0.4% to about 0.001%, about 0.3% to about 0.001%, about 0.2% to about 0.001%, about 0.1% to about 0.001%, about 0.09% to about 0.001%, about 0.08% to about 0.001%, about 0.07% to about 0.001%, about 0.06% to about 0.001%, about 0.05% to about 0.001%, about 0.04% to about 0.001%, about 0.03% to about 0.001%, about 0.02% to about 0.001%, about 0.01% to about 0.001%, or about 0.005% to about 0.001% by weight after 12 months of storage.

In some embodiments, the impurity with a relative retention time of about 0.68 is from about 1.5% to about 0.01%, about 1.4% to about 0.01%, about 1.3% to about 0.01%, about 1.2% to about 0.01%, about 1.1% to about 0.01%, about 1.0% to about 0.01%, about 0.9% to about 0.01%, about 0.8% to about 0.01%, about 0.7% to about 0.01%, about 0.6% to about 0.01%, about 0.5% to about 0.01%, about 0.4% to about 0.01%, about 0.3% to about 0.01%, about 0.2% to about 0.01%, about 0.1% to about 0.01%, about 0.09% to about 0.01%, about 0.08% to about 0.01%, about 0.07% to about 0.01%, about 0.06% to about 0.01%, about 0.05% to about 0.01%, about 0.04% to about 0.01%, about 0.03% to about 0.01%, or about 0.02% to about 0.01% by weight after 12 months of storage.

In some embodiments, the impurity with a relative retention time of about 0.68 is from about 1.5% to about 0.1%, about 1.4% to about 0.1%, about 1.3% to about 0.1%, about 1.2% to about 0.1%, about 1.1% to about 0.1%, about 1.0% to about 0.1%, about 0.9% to about 0.1%, about 0.8% to about 0.1%, about 0.7% to about 0.1%, about 0.6% to about 0.1%, about 0.5% to about 0.1%, about 0.4% to about 0.1%, about 0.3% to about 0.1%, or about 0.2% to about 0.1% by weight after 12 months of storage.

In some embodiments, the impurity with a relative retention time of about 0.68 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 12 months of storage. In some embodiments, the impurity with a relative retention time of about 0.68 is less than about 1.5% by weight after 12 months of storage. In some embodiments, the impurity with a relative retention time of about 0.68 is less than about 1.4% by weight after 12 months of storage. In some embodiments, the impurity with a relative retention time of about 0.68 is less than about 1.3% by weight after 12 months of storage. In some embodiments, the impurity with a relative retention time of about 0.68 is less than about 1.2% by weight after 12 months of storage. In some embodiments, the impurity with a relative retention time of about 0.68 is less than about 1.1% by weight after 12 months of storage. In some embodiments, the impurity with a relative retention time of about 0.68 is less than about 1.0% by weight after 12 months of storage. In some embodiments, the impurity with a relative retention time of about 0.68 is less than about 0.9% by weight after 12 months of storage. In some embodiments, the impurity with a relative retention time of about 0.68 is less than about 0.8% by weight after 12 months of storage. In some embodiments, the impurity with a relative retention time of about 0.68 is less than about 0.7% by weight after 12 months of storage. In some embodiments, the impurity with a relative retention time of about 0.68 is less than about 0.6% by weight after 12 months of storage. In some embodiments, the impurity with a relative retention time of about 0.68 is less than about 0.5% by weight after 12 months of storage. In some embodiments, the impurity with a relative retention time of about 0.68 is less than about 0.4% by weight after 12 months of storage. In some embodiments, the impurity with a relative retention time of about 0.68 is less than about 0.3% by weight after 12 months of storage. In some embodiments, the impurity with a relative retention time of about 0.68 is less than about 0.2% by weight after 12 months of storage. In some embodiments, the impurity with a relative retention time of about 0.68 is less than about 0.1% by weight after 12 months of storage. In some embodiments, the impurity with a relative retention time of about 0.68 is less than about 0.09% by weight after 12 months of storage. In some embodiments, the impurity with a relative retention time of about 0.68 is less than about 0.08% by weight after 12 months of storage. In some embodiments, the impurity with a relative retention time of about 0.68 is less than about 0.07% by weight after 12 months of storage. In some embodiments, the impurity with a relative retention time of about 0.68 is less than about 0.06% by weight after 12 months of storage. In some embodiments, the impurity with a relative retention time of about 0.68 is less than about 0.05% by weight after 12 months of storage. In some embodiments, the impurity with a relative retention time of about 0.68 is less than about 0.04% by weight after 12 months of storage. In some embodiments, the impurity with a relative retention time of about 0.68 is less than about 0.03% by weight after 12 months of storage. In some embodiments, the impurity with a relative retention time of about 0.68 is less than about 0.02% by weight after 12 months of storage. In some embodiments, the impurity with a relative retention time of about 0.68 is less than about 0.01% by weight after 12 months of storage. In some embodiments, the impurity with a relative retention time of about 0.68 is less than about 0.005% by weight after 12 months of storage. In some embodiments, the impurity with a relative retention time of about 0.68 is less than about 0.001% by weight after 12 months of storage.

In some embodiments, the impurity with a relative retention time of about 0.68 is from less than about 1.5% to about 0.001%, less than about 1.4% to about 0.001%, less than about 1.3% to about 0.001%, less than about 1.2% to about 0.001%, less than about 1.1% to about 0.001%, less than about 1.0% to about 0.001%, less than about 0.9% to about 0.001%, less than about 0.8% to about 0.001%, less than about 0.7% to about 0.001%, less than about 0.6% to about 0.001%, less than about 0.5% to about 0.001%, less than about 0.4% to about 0.001%, less than about 0.3% to about 0.001%, less than about 0.2% to about 0.001%, less than about 0.1% to about 0.001%, less than about 0.09% to about 0.001%, less than about 0.08% to about 0.001%, less than about 0.07% to about 0.001%, less than about 0.06% to about 0.001%, less than about 0.05% to about 0.001%, less than about 0.04% to about 0.001%, less than about 0.03% to about 0.001%, less than about 0.02% to about 0.001%, less than about 0.01% to about 0.001%, or less than about 0.005% to about 0.001% by weight after 12 months of storage.

In some embodiments, the impurity with a relative retention time of about 0.68 is from less than about 1.5% to about 0.01%, less than about 1.4% to about 0.01%, less than about 1.3% to about 0.01%, less than about 1.2% to about 0.01%, less than about 1.1% to about 0.01%, less than about 1.0% to about 0.01%, less than about 0.9% to about 0.01%, less than about 0.8% to about 0.01%, less than about 0.7% to about 0.01%, less than about 0.6% to about 0.01%, less than about 0.5% to about 0.01%, less than about 0.4% to about 0.01%, less than about 0.3% to about 0.01%, less than about 0.2% to about 0.01%, less than about 0.1% to about 0.01%, less than about 0.09% to about 0.01%, less than about 0.08% to about 0.01%, less than about 0.07% to about 0.01%, less than about 0.06% to about 0.01%, less than about 0.05% to about 0.01%, less than about 0.04% to about 0.01%, less than about 0.03% to about 0.01%, or less than about 0.02% to about 0.01% by weight after 12 months of storage.

In some embodiments, the impurity with a relative retention time of about 0.68 is from less than about 1.5% to about 0.1%, less than about 1.4% to about 0.1%, less than about 1.3% to about 0.1%, less than about 1.2% to about 0.1%, less than about 1.1% to about 0.1%, less than about 1.0% to about 0.1%, less than about 0.9% to about 0.1%, less than about 0.8% to about 0.1%, less than about 0.7% to about 0.1%, less than about 0.6% to about 0.1%, less than about 0.5% to about 0.1%, less than about 0.4% to about 0.1%, less than about 0.3% to about 0.1%, or less than about 0.2% to about 0.1% by weight after 12 months of storage.

In some embodiments, the impurity with a relative retention time of about 0.68 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 18 months of storage. In some embodiments, the impurity with a relative retention time of about 0.68 is about 1.5% by weight after 18 months of storage. In some embodiments, the impurity with a relative retention time of about 0.68 is about 1.4% by weight after 18 months of storage. In some embodiments, the impurity with a relative retention time of about 0.68 is about 1.3% by weight after 18 months of storage. In some embodiments, the impurity with a relative retention time of about 0.68 is about 1.2% by weight after 18 months of storage. In some embodiments, the impurity with a relative retention time of about 0.68 is about 1.1% by weight after 18 months of storage. In some embodiments, the impurity with a relative retention time of about 0.68 is about 1.0% by weight after 18 months of storage. In some embodiments, the impurity with a relative retention time of about 0.68 is about 0.9% by weight after 18 months of storage. In some embodiments, the impurity with a relative retention time of about 0.68 is about 0.8% by weight after 18 months of storage. In some embodiments, the impurity with a relative retention time of about 0.68 is about 0.7% by weight after 18 months of storage. In some embodiments, the impurity with a relative retention time of about 0.68 is about 0.6% by weight after 18 months of storage. In some embodiments, the impurity with a relative retention time of about 0.68 is about 0.5% by weight after 18 months of storage. In some embodiments, the impurity with a relative retention time of about 0.68 is about 0.4% by weight after 18 months of storage. In some embodiments, the impurity with a relative retention time of about 0.68 is about 0.3% by weight after 18 months of storage. In some embodiments, the impurity with a relative retention time of about 0.68 is about 0.2% by weight after 18 months of storage. In some embodiments, the impurity with a relative retention time of about 0.68 is about 0.1% by weight after 18 months of storage. In some embodiments, the impurity with a relative retention time of about 0.68 is about 0.09% by weight after 18 months of storage. In some embodiments, the impurity with a relative retention time of about 0.68 is about 0.08% by weight after 18 months of storage. In some embodiments, the impurity with a relative retention time of about 0.68 is about 0.07% by weight after 18 months of storage. In some embodiments, the impurity with a relative retention time of about 0.68 is about 0.06% by weight after 18 months of storage. In some embodiments, the impurity with a relative retention time of about 0.68 is about 0.05% by weight after 18 months of storage. In some embodiments, the impurity with a relative retention time of about 0.68 is about 0.04% by weight after 18 months of storage. In some embodiments, the impurity with a relative retention time of about 0.68 is about 0.03% by weight after 18 months of storage. In some embodiments, the impurity with a relative retention time of about 0.68 is about 0.02% by weight after 18 months of storage. In some embodiments, the impurity with a relative retention time of about 0.68 is about 0.01% by weight after 18 months of storage. In some embodiments, the impurity with a relative retention time of about 0.68 is about 0.005% by weight after 18 months of storage. In some embodiments, the impurity with a relative retention time of about 0.68 is about 0.001% by weight after 18 months of storage.

In some embodiments, the impurity with a relative retention time of about 0.68 is from about 1.5% to about 0.001%, about 1.4% to about 0.001%, about 1.3% to about 0.001%, about 1.2% to about 0.001%, about 1.1% to about 0.001%, about 1.0% to about 0.001%, about 0.9% to about 0.001%, about 0.8% to about 0.001%, about 0.7% to about 0.001%, about 0.6% to about 0.001%, about 0.5% to about 0.001%, about 0.4% to about 0.001%, about 0.3% to about 0.001%, about 0.2% to about 0.001%, about 0.1% to about 0.001%, about 0.09% to about 0.001%, about 0.08% to about 0.001%, about 0.07% to about 0.001%, about 0.06% to about 0.001%, about 0.05% to about 0.001%, about 0.04% to about 0.001%, about 0.03% to about 0.001%, about 0.02% to about 0.001%, about 0.01% to about 0.001%, or about 0.005% to about 0.001% by weight after 18 months of storage.

In some embodiments, the impurity with a relative retention time of about 0.68 is from about 1.5% to about 0.01%, about 1.4% to about 0.01%, about 1.3% to about 0.01%, about 1.2% to about 0.01%, about 1.1% to about 0.01%, about 1.0% to about 0.01%, about 0.9% to about 0.01%, about 0.8% to about 0.01%, about 0.7% to about 0.01%, about 0.6% to about 0.01%, about 0.5% to about 0.01%, about 0.4% to about 0.01%, about 0.3% to about 0.01%, about 0.2% to about 0.01%, about 0.1% to about 0.01%, about 0.09% to about 0.01%, about 0.08% to about 0.01%, about 0.07% to about 0.01%, about 0.06% to about 0.01%, about 0.05% to about 0.01%, about 0.04% to about 0.01%, about 0.03% to about 0.01%, or about 0.02% to about 0.01% by weight after 18 months of storage.

In some embodiments, the impurity with a relative retention time of about 0.68 is from about 1.5% to about 0.1%, about 1.4% to about 0.1%, about 1.3% to about 0.1%, about 1.2% to about 0.1%, about 1.1% to about 0.1%, about 1.0% to about 0.1%, about 0.9% to about 0.1%, about 0.8% to about 0.1%, about 0.7% to about 0.1%, about 0.6% to about 0.1%, about 0.5% to about 0.1%, about 0.4% to about 0.1%, about 0.3% to about 0.1%, or about 0.2% to about 0.1% by weight after 18 months of storage.

In some embodiments, the impurity with a relative retention time of about 0.68 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 18 months of storage. In some embodiments, the impurity with a relative retention time of about 0.68 is less than about 1.5% by weight after 18 months of storage. In some embodiments, the impurity with a relative retention time of about 0.68 is less than about 1.4% by weight after 18 months of storage. In some embodiments, the impurity with a relative retention time of about 0.68 is less than about 1.3% by weight after 18 months of storage. In some embodiments, the impurity with a relative retention time of about 0.68 is less than about 1.2% by weight after 18 months of storage. In some embodiments, the impurity with a relative retention time of about 0.68 is less than about 1.1% by weight after 18 months of storage. In some embodiments, the impurity with a relative retention time of about 0.68 is less than about 1.0% by weight after 18 months of storage. In some embodiments, the impurity with a relative retention time of about 0.68 is less than about 0.9% by weight after 18 months of storage. In some embodiments, the impurity with a relative retention time of about 0.68 is less than about 0.8% by weight after 18 months of storage. In some embodiments, the impurity with a relative retention time of about 0.68 is less than about 0.7% by weight after 18 months of storage. In some embodiments, the impurity with a relative retention time of about 0.68 is less than about 0.6% by weight after 18 months of storage. In some embodiments, the impurity with a relative retention time of about 0.68 is less than about 0.5% by weight after 18 months of storage. In some embodiments, the impurity with a relative retention time of about 0.68 is less than about 0.4% by weight after 18 months of storage. In some embodiments, the impurity with a relative retention time of about 0.68 is less than about 0.3% by weight after 18 months of storage. In some embodiments, the impurity with a relative retention time of about 0.68 is less than about 0.2% by weight after 18 months of storage. In some embodiments, the impurity with a relative retention time of about 0.68 is less than about 0.1% by weight after 18 months of storage. In some embodiments, the impurity with a relative retention time of about 0.68 is less than about 0.09% by weight after 18 months of storage. In some embodiments, the impurity with a relative retention time of about 0.68 is less than about 0.08% by weight after 18 months of storage. In some embodiments, the impurity with a relative retention time of about 0.68 is less than about 0.07% by weight after 18 months of storage. In some embodiments, the impurity with a relative retention time of about 0.68 is less than about 0.06% by weight after 18 months of storage. In some embodiments, the impurity with a relative retention time of about 0.68 is less than about 0.05% by weight after 18 months of storage. In some embodiments, the impurity with a relative retention time of about 0.68 is less than about 0.04% by weight after 18 months of storage. In some embodiments, the impurity with a relative retention time of about 0.68 is less than about 0.03% by weight after 18 months of storage. In some embodiments, the impurity with a relative retention time of about 0.68 is less than about 0.02% by weight after 18 months of storage. In some embodiments, the impurity with a relative retention time of about 0.68 is less than about 0.01% by weight after 18 months of storage. In some embodiments, the impurity with a relative retention time of about 0.68 is less than about 0.005% by weight after 18 months of storage. In some embodiments, the impurity with a relative retention time of about 0.68 is less than about 0.001% by weight after 18 months of storage.

In some embodiments, the impurity with a relative retention time of about 0.68 is from less than about 1.5% to about 0.001%, less than about 1.4% to about 0.001%, less than about 1.3% to about 0.001%, less than about 1.2% to about 0.001%, less than about 1.1% to about 0.001%, less than about 1.0% to about 0.001%, less than about 0.9% to about 0.001%, less than about 0.8% to about 0.001%, less than about 0.7% to about 0.001%, less than about 0.6% to about 0.001%, less than about 0.5% to about 0.001%, less than about 0.4% to about 0.001%, less than about 0.3% to about 0.001%, less than about 0.2% to about 0.001%, less than about 0.1% to about 0.001%, less than about 0.09% to about 0.001%, less than about 0.08% to about 0.001%, less than about 0.07% to about 0.001%, less than about 0.06% to about 0.001%, less than about 0.05% to about 0.001%, less than about 0.04% to about 0.001%, less than about 0.03% to about 0.001%, less than about 0.02% to about 0.001%, less than about 0.01% to about 0.001%, or less than about 0.005% to about 0.001% by weight after 18 months of storage.

In some embodiments, the impurity with a relative retention time of about 0.68 is from less than about 1.5% to about 0.01%, less than about 1.4% to about 0.01%, less than about 1.3% to about 0.01%, less than about 1.2% to about 0.01%, less than about 1.1% to about 0.01%, less than about 1.0% to about 0.01%, less than about 0.9% to about 0.01%, less than about 0.8% to about 0.01%, less than about 0.7% to about 0.01%, less than about 0.6% to about 0.01%, less than about 0.5% to about 0.01%, less than about 0.4% to about 0.01%, less than about 0.3% to about 0.01%, less than about 0.2% to about 0.01%, less than about 0.1% to about 0.01%, less than about 0.09% to about 0.01%, less than about 0.08% to about 0.01%, less than about 0.07% to about 0.01%, less than about 0.06% to about 0.01%, less than about 0.05% to about 0.01%, less than about 0.04% to about 0.01%, less than about 0.03% to about 0.01%, or less than about 0.02% to about 0.01% by weight after 18 months of storage.

In some embodiments, the impurity with a relative retention time of about 0.68 is from less than about 1.5% to about 0.1%, less than about 1.4% to about 0.1%, less than about 1.3% to about 0.1%, less than about 1.2% to about 0.1%, less than about 1.1% to about 0.1%, less than about 1.0% to about 0.1%, less than about 0.9% to about 0.1%, less than about 0.8% to about 0.1%, less than about 0.7% to about 0.1%, less than about 0.6% to about 0.1%, less than about 0.5% to about 0.1%, less than about 0.4% to about 0.1%, less than about 0.3% to about 0.1%, or less than about 0.2% to about 0.1% by weight after 18 months of storage.

In some embodiments, the total impurity comprises an impurity with a relative retention time of about 0.74. In some embodiments, the total impurity comprises an impurity with a relative retention time of about 0.74±0.01, about 0.74±0.02, about 0.74±0.03, about 0.74±0.04, about 0.74±0.05, about 0.74±0.06, about 0.74±0.07, about 0.74±0.08, about 0.74±0.09, or about 0.74±0.10.

In some embodiments, the impurity with a relative retention time of about 0.74 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight. In some embodiments, the impurity with a relative retention time of about 0.74 is about 1.5% by weight. In some embodiments, the impurity with a relative retention time of about 0.74 is about 1.4% by weight. In some embodiments, the impurity with a relative retention time of about 0.74 is about 1.3% by weight. In some embodiments, the impurity with a relative retention time of about 0.74 is about 1.2% by weight. In some embodiments, the impurity with a relative retention time of about 0.74 is about 1.1% by weight. In some embodiments, the impurity with a relative retention time of about 0.74 is about 1.0% by weight. In some embodiments, the impurity with a relative retention time of about 0.74 is about 0.9% by weight. In some embodiments, the impurity with a relative retention time of about 0.74 is about 0.8% by weight. In some embodiments, the impurity with a relative retention time of about 0.74 is about 0.7% by weight. In some embodiments, the impurity with a relative retention time of about 0.74 is about 0.6% by weight. In some embodiments, the impurity with a relative retention time of about 0.74 is about 0.5% by weight. In some embodiments, the impurity with a relative retention time of about 0.74 is about 0.4% by weight. In some embodiments, the impurity with a relative retention time of about 0.74 is about 0.3% by weight. In some embodiments, the impurity with a relative retention time of about 0.74 is about 0.2% by weight. In some embodiments, the impurity with a relative retention time of about 0.74 is about 0.1% by weight. In some embodiments, the impurity with a relative retention time of about 0.74 is about 0.09% by weight. In some embodiments, the impurity with a relative retention time of about 0.74 is about 0.08% by weight. In some embodiments, the impurity with a relative retention time of about 0.74 is about 0.07% by weight. In some embodiments, the impurity with a relative retention time of about 0.74 is about 0.06% by weight. In some embodiments, the impurity with a relative retention time of about 0.74 is about 0.05% by weight. In some embodiments, the impurity with a relative retention time of about 0.74 is about 0.04% by weight. In some embodiments, the impurity with a relative retention time of about 0.74 is about 0.03% by weight. In some embodiments, the impurity with a relative retention time of about 0.74 is about 0.02% by weight. In some embodiments, the impurity with a relative retention time of about 0.74 is about 0.01% by weight. In some embodiments, the impurity with a relative retention time of about 0.74 is about 0.005% by weight. In some embodiments, the impurity with a relative retention time of about 0.74 is about 0.001% by weight.

In some embodiments, the impurity with a relative retention time of about 0.74 is from about 1.5% to about 0.001%, about 1.4% to about 0.001%, about 1.3% to about 0.001%, about 1.2% to about 0.001%, about 1.1% to about 0.001%, about 1.0% to about 0.001%, about 0.9% to about 0.001%, about 0.8% to about 0.001%, about 0.7% to about 0.001%, about 0.6% to about 0.001%, about 0.5% to about 0.001%, about 0.4% to about 0.001%, about 0.3% to about 0.001%, about 0.2% to about 0.001%, about 0.1% to about 0.001%, about 0.09% to about 0.001%, about 0.08% to about 0.001%, about 0.07% to about 0.001%, about 0.06% to about 0.001%, about 0.05% to about 0.001%, about 0.04% to about 0.001%, about 0.03% to about 0.001%, about 0.02% to about 0.001%, about 0.01% to about 0.001%, or about 0.005% to about 0.001% by weight.

In some embodiments, the impurity with a relative retention time of about 0.74 is from about 1.5% to about 0.01%, about 1.4% to about 0.01%, about 1.3% to about 0.01%, about 1.2% to about 0.01%, about 1.1% to about 0.01%, about 1.0% to about 0.01%, about 0.9% to about 0.01%, about 0.8% to about 0.01%, about 0.7% to about 0.01%, about 0.6% to about 0.01%, about 0.5% to about 0.01%, about 0.4% to about 0.01%, about 0.3% to about 0.01%, about 0.2% to about 0.01%, about 0.1% to about 0.01%, about 0.09% to about 0.01%, about 0.08% to about 0.01%, about 0.07% to about 0.01%, about 0.06% to about 0.01%, about 0.05% to about 0.01%, about 0.04% to about 0.01%, about 0.03% to about 0.01%, or about 0.02% to about 0.01% by weight.

In some embodiments, the impurity with a relative retention time of about 0.74 is from about 1.5% to about 0.1%, about 1.4% to about 0.1%, about 1.3% to about 0.1%, about 1.2% to about 0.1%, about 1.1% to about 0.1%, about 1.0% to about 0.1%, about 0.9% to about 0.1%, about 0.8% to about 0.1%, about 0.7% to about 0.1%, about 0.6% to about 0.1%, about 0.5% to about 0.1%, about 0.4% to about 0.1%, about 0.3% to about 0.1%, or about 0.2% to about 0.1% by weight.

In some embodiments, the impurity with a relative retention time of about 0.74 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight. In some embodiments, the impurity with a relative retention time of about 0.74 is less than about 1.5% by weight. In some embodiments, the impurity with a relative retention time of about 0.74 is less than about 1.4% by weight. In some embodiments, the impurity with a relative retention time of about 0.74 is less than about 1.3% by weight. In some embodiments, the impurity with a relative retention time of about 0.74 is less than about 1.2% by weight. In some embodiments, the impurity with a relative retention time of about 0.74 is less than about 1.1% by weight. In some embodiments, the impurity with a relative retention time of about 0.74 is less than about 1.0% by weight. In some embodiments, the impurity with a relative retention time of about 0.74 is less than about 0.9% by weight. In some embodiments, the impurity with a relative retention time of about 0.74 is less than about 0.8% by weight. In some embodiments, the impurity with a relative retention time of about 0.74 is less than about 0.7% by weight. In some embodiments, the impurity with a relative retention time of about 0.74 is less than about 0.6% by weight. In some embodiments, the impurity with a relative retention time of about 0.74 is less than about 0.5% by weight. In some embodiments, the impurity with a relative retention time of about 0.74 is less than about 0.4% by weight. In some embodiments, the impurity with a relative retention time of about 0.74 is less than about 0.3% by weight. In some embodiments, the impurity with a relative retention time of about 0.74 is less than about 0.2% by weight. In some embodiments, the impurity with a relative retention time of about 0.74 is less than about 0.1% by weight. In some embodiments, the impurity with a relative retention time of about 0.74 is less than about 0.09% by weight. In some embodiments, the impurity with a relative retention time of about 0.74 is less than about 0.08% by weight. In some embodiments, the impurity with a relative retention time of about 0.74 is less than about 0.07% by weight. In some embodiments, the impurity with a relative retention time of about 0.74 is less than about 0.06% by weight. In some embodiments, the impurity with a relative retention time of about 0.74 is less than about 0.05% by weight. In some embodiments, the impurity with a relative retention time of about 0.74 is less than about 0.04% by weight. In some embodiments, the impurity with a relative retention time of about 0.74 is less than about 0.03% by weight. In some embodiments, the impurity with a relative retention time of about 0.74 is less than about 0.02% by weight. In some embodiments, the impurity with a relative retention time of about 0.74 is less than about 0.01% by weight. In some embodiments, the impurity with a relative retention time of about 0.74 is less than about 0.005% by weight. In some embodiments, the impurity with a relative retention time of about 0.74 is less than about 0.001% by weight.

In some embodiments, the impurity with a relative retention time of about 0.74 is from less than about 1.5% to about 0.001%, less than about 1.4% to about 0.001%, less than about 1.3% to about 0.001%, less than about 1.2% to about 0.001%, less than about 1.1% to about 0.001%, less than about 1.0% to about 0.001%, less than about 0.9% to about 0.001%, less than about 0.8% to about 0.001%, less than about 0.7% to about 0.001%, less than about 0.6% to about 0.001%, less than about 0.5% to about 0.001%, less than about 0.4% to about 0.001%, less than about 0.3% to about 0.001%, less than about 0.2% to about 0.001%, less than about 0.1% to about 0.001%, less than about 0.09% to about 0.001%, less than about 0.08% to about 0.001%, less than about 0.07% to about 0.001%, less than about 0.06% to about 0.001%, less than about 0.05% to about 0.001%, less than about 0.04% to about 0.001%, less than about 0.03% to about 0.001%, less than about 0.02% to about 0.001%, less than about 0.01% to about 0.001%, or less than about 0.005% to about 0.001% by weight.

In some embodiments, the impurity with a relative retention time of about 0.74 is from less than about 1.5% to about 0.01%, less than about 1.4% to about 0.01%, less than about 1.3% to about 0.01%, less than about 1.2% to about 0.01%, less than about 1.1% to about 0.01%, less than about 1.0% to about 0.01%, less than about 0.9% to about 0.01%, less than about 0.8% to about 0.01%, less than about 0.7% to about 0.01%, less than about 0.6% to about 0.01%, less than about 0.5% to about 0.01%, less than about 0.4% to about 0.01%, less than about 0.3% to about 0.01%, less than about 0.2% to about 0.01%, less than about 0.1% to about 0.01%, less than about 0.09% to about 0.01%, less than about 0.08% to about 0.01%, less than about 0.07% to about 0.01%, less than about 0.06% to about 0.01%, less than about 0.05% to about 0.01%, less than about 0.04% to about 0.01%, less than about 0.03% to about 0.01%, or less than about 0.02% to about 0.01% by weight.

In some embodiments, the impurity with a relative retention time of about 0.74 is from less than about 1.5% to about 0.1%, less than about 1.4% to about 0.1%, less than about 1.3% to about 0.1%, less than about 1.2% to about 0.1%, less than about 1.1% to about 0.1%, less than about 1.0% to about 0.1%, less than about 0.9% to about 0.1%, less than about 0.8% to about 0.1%, less than about 0.7% to about 0.1%, less than about 0.6% to about 0.1%, less than about 0.5% to about 0.1%, less than about 0.4% to about 0.1%, less than about 0.3% to about 0.1%, or less than about 0.2% to about 0.1% by weight.

In some embodiments, the impurity with a relative retention time of about 0.74 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 0 months of storage. In some embodiments, the impurity with a relative retention time of about 0.74 is about 1.5% by weight after 0 months of storage. In some embodiments, the impurity with a relative retention time of about 0.74 is about 1.4% by weight after 0 months of storage. In some embodiments, the impurity with a relative retention time of about 0.74 is about 1.3% by weight after 0 months of storage. In some embodiments, the impurity with a relative retention time of about 0.74 is about 1.2% by weight after 0 months of storage. In some embodiments, the impurity with a relative retention time of about 0.74 is about 1.1% by weight after 0 months of storage. In some embodiments, the impurity with a relative retention time of about 0.74 is about 1.0% by weight after 0 months of storage. In some embodiments, the impurity with a relative retention time of about 0.74 is about 0.9% by weight after 0 months of storage. In some embodiments, the impurity with a relative retention time of about 0.74 is about 0.8% by weight after 0 months of storage. In some embodiments, the impurity with a relative retention time of about 0.74 is about 0.7% by weight after 0 months of storage. In some embodiments, the impurity with a relative retention time of about 0.74 is about 0.6% by weight after 0 months of storage. In some embodiments, the impurity with a relative retention time of about 0.74 is about 0.5% by weight after 0 months of storage. In some embodiments, the impurity with a relative retention time of about 0.74 is about 0.4% by weight after 0 months of storage. In some embodiments, the impurity with a relative retention time of about 0.74 is about 0.3% by weight after 0 months of storage. In some embodiments, the impurity with a relative retention time of about 0.74 is about 0.2% by weight after 0 months of storage. In some embodiments, the impurity with a relative retention time of about 0.74 is about 0.1% by weight after 0 months of storage. In some embodiments, the impurity with a relative retention time of about 0.74 is about 0.09% by weight after 0 months of storage. In some embodiments, the impurity with a relative retention time of about 0.74 is about 0.08% by weight after 0 months of storage. In some embodiments, the impurity with a relative retention time of about 0.74 is about 0.07% by weight after 0 months of storage. In some embodiments, the impurity with a relative retention time of about 0.74 is about 0.06% by weight after 0 months of storage. In some embodiments, the impurity with a relative retention time of about 0.74 is about 0.05% by weight after 0 months of storage. In some embodiments, the impurity with a relative retention time of about 0.74 is about 0.04% by weight after 0 months of storage. In some embodiments, the impurity with a relative retention time of about 0.74 is about 0.03% by weight after 0 months of storage. In some embodiments, the impurity with a relative retention time of about 0.74 is about 0.02% by weight after 0 months of storage. In some embodiments, the impurity with a relative retention time of about 0.74 is about 0.01% by weight after 0 months of storage. In some embodiments, the impurity with a relative retention time of about 0.74 is about 0.005% by weight after 0 months of storage. In some embodiments, the impurity with a relative retention time of about 0.74 is about 0.001% by weight after 0 months of storage.

In some embodiments, the impurity with a relative retention time of about 0.74 is from about 1.5% to about 0.001%, about 1.4% to about 0.001%, about 1.3% to about 0.001%, about 1.2% to about 0.001%, about 1.1% to about 0.001%, about 1.0% to about 0.001%, about 0.9% to about 0.001%, about 0.8% to about 0.001%, about 0.7% to about 0.001%, about 0.6% to about 0.001%, about 0.5% to about 0.001%, about 0.4% to about 0.001%, about 0.3% to about 0.001%, about 0.2% to about 0.001%, about 0.1% to about 0.001%, about 0.09% to about 0.001%, about 0.08% to about 0.001%, about 0.07% to about 0.001%, about 0.06% to about 0.001%, about 0.05% to about 0.001%, about 0.04% to about 0.001%, about 0.03% to about 0.001%, about 0.02% to about 0.001%, about 0.01% to about 0.001%, or about 0.005% to about 0.001% by weight after 0 months of storage.

In some embodiments, the impurity with a relative retention time of about 0.74 is from about 1.5% to about 0.01%, about 1.4% to about 0.01%, about 1.3% to about 0.01%, about 1.2% to about 0.01%, about 1.1% to about 0.01%, about 1.0% to about 0.01%, about 0.9% to about 0.01%, about 0.8% to about 0.01%, about 0.7% to about 0.01%, about 0.6% to about 0.01%, about 0.5% to about 0.01%, about 0.4% to about 0.01%, about 0.3% to about 0.01%, about 0.2% to about 0.01%, about 0.1% to about 0.01%, about 0.09% to about 0.01%, about 0.08% to about 0.01%, about 0.07% to about 0.01%, about 0.06% to about 0.01%, about 0.05% to about 0.01%, about 0.04% to about 0.01%, about 0.03% to about 0.01%, or about 0.02% to about 0.01% by weight after 0 months of storage.

In some embodiments, the impurity with a relative retention time of about 0.74 is from about 1.5% to about 0.1%, about 1.4% to about 0.1%, about 1.3% to about 0.1%, about 1.2% to about 0.1%, about 1.1% to about 0.1%, about 1.0% to about 0.1%, about 0.9% to about 0.1%, about 0.8% to about 0.1%, about 0.7% to about 0.1%, about 0.6% to about 0.1%, about 0.5% to about 0.1%, about 0.4% to about 0.1%, about 0.3% to about 0.1%, or about 0.2% to about 0.1% by weight after 0 months of storage.

In some embodiments, the impurity with a relative retention time of about 0.74 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 0 months of storage. In some embodiments, the impurity with a relative retention time of about 0.74 is less than about 1.5% by weight after 0 months of storage. In some embodiments, the impurity with a relative retention time of about 0.74 is less than about 1.4% by weight after 0 months of storage. In some embodiments, the impurity with a relative retention time of about 0.74 is less than about 1.3% by weight after 0 months of storage. In some embodiments, the impurity with a relative retention time of about 0.74 is less than about 1.2% by weight after 0 months of storage. In some embodiments, the impurity with a relative retention time of about 0.74 is less than about 1.1% by weight after 0 months of storage. In some embodiments, the impurity with a relative retention time of about 0.74 is less than about 1.0% by weight after 0 months of storage. In some embodiments, the impurity with a relative retention time of about 0.74 is less than about 0.9% by weight after 0 months of storage. In some embodiments, the impurity with a relative retention time of about 0.74 is less than about 0.8% by weight after 0 months of storage. In some embodiments, the impurity with a relative retention time of about 0.74 is less than about 0.7% by weight after 0 months of storage. In some embodiments, the impurity with a relative retention time of about 0.74 is less than about 0.6% by weight after 0 months of storage. In some embodiments, the impurity with a relative retention time of about 0.74 is less than about 0.5% by weight after 0 months of storage. In some embodiments, the impurity with a relative retention time of about 0.74 is less than about 0.4% by weight after 0 months of storage. In some embodiments, the impurity with a relative retention time of about 0.74 is less than about 0.3% by weight after 0 months of storage. In some embodiments, the impurity with a relative retention time of about 0.74 is less than about 0.2% by weight after 0 months of storage. In some embodiments, the impurity with a relative retention time of about 0.74 is less than about 0.1% by weight after 0 months of storage. In some embodiments, the impurity with a relative retention time of about 0.74 is less than about 0.09% by weight after 0 months of storage. In some embodiments, the impurity with a relative retention time of about 0.74 is less than about 0.08% by weight after 0 months of storage. In some embodiments, the impurity with a relative retention time of about 0.74 is less than about 0.07% by weight after 0 months of storage. In some embodiments, the impurity with a relative retention time of about 0.74 is less than about 0.06% by weight after 0 months of storage. In some embodiments, the impurity with a relative retention time of about 0.74 is less than about 0.05% by weight after 0 months of storage. In some embodiments, the impurity with a relative retention time of about 0.74 is less than about 0.04% by weight after 0 months of storage. In some embodiments, the impurity with a relative retention time of about 0.74 is less than about 0.03% by weight after 0 months of storage. In some embodiments, the impurity with a relative retention time of about 0.74 is less than about 0.02% by weight after 0 months of storage. In some embodiments, the impurity with a relative retention time of about 0.74 is less than about 0.01% by weight after 0 months of storage. In some embodiments, the impurity with a relative retention time of about 0.74 is less than about 0.005% by weight after 0 months of storage. In some embodiments, the impurity with a relative retention time of about 0.74 is less than about 0.001% by weight after 0 months of storage.

In some embodiments, the impurity with a relative retention time of about 0.74 is from less than about 1.5% to about 0.001%, less than about 1.4% to about 0.001%, less than about 1.3% to about 0.001%, less than about 1.2% to about 0.001%, less than about 1.1% to about 0.001%, less than about 1.0% to about 0.001%, less than about 0.9% to about 0.001%, less than about 0.8% to about 0.001%, less than about 0.7% to about 0.001%, less than about 0.6% to about 0.001%, less than about 0.5% to about 0.001%, less than about 0.4% to about 0.001%, less than about 0.3% to about 0.001%, less than about 0.2% to about 0.001%, less than about 0.1% to about 0.001%, less than about 0.09% to about 0.001%, less than about 0.08% to about 0.001%, less than about 0.07% to about 0.001%, less than about 0.06% to about 0.001%, less than about 0.05% to about 0.001%, less than about 0.04% to about 0.001%, less than about 0.03% to about 0.001%, less than about 0.02% to about 0.001%, less than about 0.01% to about 0.001%, or less than about 0.005% to about 0.001% by weight after 0 months of storage.

In some embodiments, the impurity with a relative retention time of about 0.74 is from less than about 1.5% to about 0.01%, less than about 1.4% to about 0.01%, less than about 1.3% to about 0.01%, less than about 1.2% to about 0.01%, less than about 1.1% to about 0.01%, less than about 1.0% to about 0.01%, less than about 0.9% to about 0.01%, less than about 0.8% to about 0.01%, less than about 0.7% to about 0.01%, less than about 0.6% to about 0.01%, less than about 0.5% to about 0.01%, less than about 0.4% to about 0.01%, less than about 0.3% to about 0.01%, less than about 0.2% to about 0.01%, less than about 0.1% to about 0.01%, less than about 0.09% to about 0.01%, less than about 0.08% to about 0.01%, less than about 0.07% to about 0.01%, less than about 0.06% to about 0.01%, less than about 0.05% to about 0.01%, less than about 0.04% to about 0.01%, less than about 0.03% to about 0.01%, or less than about 0.02% to about 0.01% by weight after 0 months of storage.

In some embodiments, the impurity with a relative retention time of about 0.74 is from less than about 1.5% to about 0.1%, less than about 1.4% to about 0.1%, less than about 1.3% to about 0.1%, less than about 1.2% to about 0.1%, less than about 1.1% to about 0.1%, less than about 1.0% to about 0.1%, less than about 0.9% to about 0.1%, less than about 0.8% to about 0.1%, less than about 0.7% to about 0.1%, less than about 0.6% to about 0.1%, less than about 0.5% to about 0.1%, less than about 0.4% to about 0.1%, less than about 0.3% to about 0.1%, or less than about 0.2% to about 0.1% by weight after 0 months of storage.

In some embodiments, the impurity with a relative retention time of about 0.74 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 12 months of storage. In some embodiments, the impurity with a relative retention time of about 0.74 is about 1.5% by weight after 12 months of storage. In some embodiments, the impurity with a relative retention time of about 0.74 is about 1.4% by weight after 12 months of storage. In some embodiments, the impurity with a relative retention time of about 0.74 is about 1.3% by weight after 12 months of storage. In some embodiments, the impurity with a relative retention time of about 0.74 is about 1.2% by weight after 12 months of storage. In some embodiments, the impurity with a relative retention time of about 0.74 is about 1.1% by weight after 12 months of storage. In some embodiments, the impurity with a relative retention time of about 0.74 is about 1.0% by weight after 12 months of storage. In some embodiments, the impurity with a relative retention time of about 0.74 is about 0.9% by weight after 12 months of storage. In some embodiments, the impurity with a relative retention time of about 0.74 is about 0.8% by weight after 12 months of storage. In some embodiments, the impurity with a relative retention time of about 0.74 is about 0.7% by weight after 12 months of storage. In some embodiments, the impurity with a relative retention time of about 0.74 is about 0.6% by weight after 12 months of storage. In some embodiments, the impurity with a relative retention time of about 0.74 is about 0.5% by weight after 12 months of storage. In some embodiments, the impurity with a relative retention time of about 0.74 is about 0.4% by weight after 12 months of storage. In some embodiments, the impurity with a relative retention time of about 0.74 is about 0.3% by weight after 12 months of storage. In some embodiments, the impurity with a relative retention time of about 0.74 is about 0.2% by weight after 12 months of storage. In some embodiments, the impurity with a relative retention time of about 0.74 is about 0.1% by weight after 12 months of storage. In some embodiments, the impurity with a relative retention time of about 0.74 is about 0.09% by weight after 12 months of storage. In some embodiments, the impurity with a relative retention time of about 0.74 is about 0.08% by weight after 12 months of storage. In some embodiments, the impurity with a relative retention time of about 0.74 is about 0.07% by weight after 12 months of storage. In some embodiments, the impurity with a relative retention time of about 0.74 is about 0.06% by weight after 12 months of storage. In some embodiments, the impurity with a relative retention time of about 0.74 is about 0.05% by weight after 12 months of storage. In some embodiments, the impurity with a relative retention time of about 0.74 is about 0.04% by weight after 12 months of storage. In some embodiments, the impurity with a relative retention time of about 0.74 is about 0.03% by weight after 12 months of storage. In some embodiments, the impurity with a relative retention time of about 0.74 is about 0.02% by weight after 12 months of storage. In some embodiments, the impurity with a relative retention time of about 0.74 is about 0.01% by weight after 12 months of storage. In some embodiments, the impurity with a relative retention time of about 0.74 is about 0.005% by weight after 12 months of storage. In some embodiments, the impurity with a relative retention time of about 0.74 is about 0.001% by weight after 12 months of storage.

In some embodiments, the impurity with a relative retention time of about 0.74 is from about 1.5% to about 0.001%, about 1.4% to about 0.001%, about 1.3% to about 0.001%, about 1.2% to about 0.001%, about 1.1% to about 0.001%, about 1.0% to about 0.001%, about 0.9% to about 0.001%, about 0.8% to about 0.001%, about 0.7% to about 0.001%, about 0.6% to about 0.001%, about 0.5% to about 0.001%, about 0.4% to about 0.001%, about 0.3% to about 0.001%, about 0.2% to about 0.001%, about 0.1% to about 0.001%, about 0.09% to about 0.001%, about 0.08% to about 0.001%, about 0.07% to about 0.001%, about 0.06% to about 0.001%, about 0.05% to about 0.001%, about 0.04% to about 0.001%, about 0.03% to about 0.001%, about 0.02% to about 0.001%, about 0.01% to about 0.001%, or about 0.005 to about 0.001% by weight after 12 months of storage.

In some embodiments, the impurity with a relative retention time of about 0.74 is from about 1.5% to about 0.01%, about 1.4% to about 0.01%, about 1.3% to about 0.01%, about 1.2% to about 0.01%, about 1.1% to about 0.01%, about 1.0% to about 0.01%, about 0.9% to about 0.01%, about 0.8% to about 0.01%, about 0.7% to about 0.01%, about 0.6% to about 0.01%, about 0.5% to about 0.01%, about 0.4% to about 0.01%, about 0.3% to about 0.01%, about 0.2% to about 0.01%, about 0.1% to about 0.01%, about 0.09% to about 0.01%, about 0.08% to about 0.01%, about 0.07% to about 0.01%, about 0.06% to about 0.01%, about 0.05% to about 0.01%, about 0.04% to about 0.01%, about 0.03% to about 0.01%, or about 0.02% to about 0.01% by weight after 12 months of storage.

In some embodiments, the impurity with a relative retention time of about 0.74 is from about 1.5% to about 0.1%, about 1.4% to about 0.1%, about 1.3% to about 0.1%, about 1.2% to about 0.1%, about 1.1% to about 0.1%, about 1.0% to about 0.1%, about 0.9% to about 0.1%, about 0.8% to about 0.1%, about 0.7% to about 0.1%, about 0.6% to about 0.1%, about 0.5% to about 0.1%, about 0.4% to about 0.1%, about 0.3% to about 0.1%, or about 0.2% to about 0.1% by weight after 12 months of storage.

In some embodiments, the impurity with a relative retention time of about 0.74 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 12 months of storage. In some embodiments, the impurity with a relative retention time of about 0.74 is less than about 1.5% by weight after 12 months of storage. In some embodiments, the impurity with a relative retention time of about 0.74 is less than about 1.4% by weight after 12 months of storage. In some embodiments, the impurity with a relative retention time of about 0.74 is less than about 1.3% by weight after 12 months of storage. In some embodiments, the impurity with a relative retention time of about 0.74 is less than about 1.2% by weight after 12 months of storage. In some embodiments, the impurity with a relative retention time of about 0.74 is less than about 1.1% by weight after 12 months of storage. In some embodiments, the impurity with a relative retention time of about 0.74 is less than about 1.0% by weight after 12 months of storage. In some embodiments, the impurity with a relative retention time of about 0.74 is less than about 0.9% by weight after 12 months of storage. In some embodiments, the impurity with a relative retention time of about 0.74 is less than about 0.8% by weight after 12 months of storage. In some embodiments, the impurity with a relative retention time of about 0.74 is less than about 0.7% by weight after 12 months of storage. In some embodiments, the impurity with a relative retention time of about 0.74 is less than about 0.6% by weight after 12 months of storage. In some embodiments, the impurity with a relative retention time of about 0.74 is less than about 0.5% by weight after 12 months of storage. In some embodiments, the impurity with a relative retention time of about 0.74 is less than about 0.4% by weight after 12 months of storage. In some embodiments, the impurity with a relative retention time of about 0.74 is less than about 0.3% by weight after 12 months of storage. In some embodiments, the impurity with a relative retention time of about 0.74 is less than about 0.2% by weight after 12 months of storage. In some embodiments, the impurity with a relative retention time of about 0.74 is less than about 0.1% by weight after 12 months of storage. In some embodiments, the impurity with a relative retention time of about 0.74 is less than about 0.09% by weight after 12 months of storage. In some embodiments, the impurity with a relative retention time of about 0.74 is less than about 0.08% by weight after 12 months of storage. In some embodiments, the impurity with a relative retention time of about 0.74 is less than about 0.07% by weight after 12 months of storage. In some embodiments, the impurity with a relative retention time of about 0.74 is less than about 0.06% by weight after 12 months of storage. In some embodiments, the impurity with a relative retention time of about 0.74 is less than about 0.05% by weight after 12 months of storage. In some embodiments, the impurity with a relative retention time of about 0.74 is less than about 0.04% by weight after 12 months of storage. In some embodiments, the impurity with a relative retention time of about 0.74 is less than about 0.03% by weight after 12 months of storage. In some embodiments, the impurity with a relative retention time of about 0.74 is less than about 0.02% by weight after 12 months of storage. In some embodiments, the impurity with a relative retention time of about 0.74 is less than about 0.01% by weight after 12 months of storage. In some embodiments, the impurity with a relative retention time of about 0.74 is less than about 0.005% by weight after 12 months of storage. In some embodiments, the impurity with a relative retention time of about 0.74 is less than about 0.001% by weight after 12 months of storage.

In some embodiments, the impurity with a relative retention time of about 0.74 is from less than about 1.5% to about 0.001%, less than about 1.4% to about 0.001%, less than about 1.3% to about 0.001%, less than about 1.2% to about 0.001%, less than about 1.1% to about 0.001%, less than about 1.0% to about 0.001%, less than about 0.9% to about 0.001%, less than about 0.8% to about 0.001%, less than about 0.7% to about 0.001%, less than about 0.6% to about 0.001%, less than about 0.5% to about 0.001%, less than about 0.4% to about 0.001%, less than about 0.3% to about 0.001%, less than about 0.2% to about 0.001%, less than about 0.1% to about 0.001%, less than about 0.09% to about 0.001%, less than about 0.08% to about 0.001%, less than about 0.07% to about 0.001%, less than about 0.06% to about 0.001%, less than about 0.05% to about 0.001%, less than about 0.04% to about 0.001%, less than about 0.03% to about 0.001%, less than about 0.02% to about 0.001%, less than about 0.01% to about 0.001%, or less than about 0.005% to about 0.001% by weight after 12 months of storage.

In some embodiments, the impurity with a relative retention time of about 0.74 is from less than about 1.5% to about 0.01%, less than about 1.4% to about 0.01%, less than about 1.3% to about 0.01%, less than about 1.2% to about 0.01%, less than about 1.1% to about 0.01%, less than about 1.0% to about 0.01%, less than about 0.9% to about 0.01%, less than about 0.8% to about 0.01%, less than about 0.7% to about 0.01%, less than about 0.6% to about 0.01%, less than about 0.5% to about 0.01%, less than about 0.4% to about 0.01%, less than about 0.3% to about 0.01%, less than about 0.2% to about 0.01%, less than about 0.1% to about 0.01%, less than about 0.09% to about 0.01%, less than about 0.08% to about 0.01%, less than about 0.07% to about 0.01%, less than about 0.06% to about 0.01%, less than about 0.05% to about 0.01%, less than about 0.04% to about 0.01%, less than about 0.03% to about 0.01%, or less than about 0.02% to about 0.01% by weight after 12 months of storage.

In some embodiments, the impurity with a relative retention time of about 0.74 is from less than about 1.5% to about 0.1%, less than about 1.4% to about 0.1%, less than about 1.3% to about 0.1%, less than about 1.2% to about 0.1%, less than about 1.1% to about 0.1%, less than about 1.0% to about 0.1%, less than about 0.9% to about 0.1%, less than about 0.8% to about 0.1%, less than about 0.7% to about 0.1%, less than about 0.6% to about 0.1%, less than about 0.5% to about 0.1%, less than about 0.4% to about 0.1%, less than about 0.3% to about 0.1%, or less than about 0.2% to about 0.1% by weight after 12 months of storage.

In some embodiments, the impurity with a relative retention time of about 0.74 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 18 months of storage. In some embodiments, the impurity with a relative retention time of about 0.74 is about 1.5% by weight after 18 months of storage. In some embodiments, the impurity with a relative retention time of about 0.74 is about 1.4% by weight after 18 months of storage. In some embodiments, the impurity with a relative retention time of about 0.74 is about 1.3% by weight after 18 months of storage. In some embodiments, the impurity with a relative retention time of about 0.74 is about 1.2% by weight after 18 months of storage. In some embodiments, the impurity with a relative retention time of about 0.74 is about 1.1% by weight after 18 months of storage. In some embodiments, the impurity with a relative retention time of about 0.74 is about 1.0% by weight after 18 months of storage. In some embodiments, the impurity with a relative retention time of about 0.74 is about 0.9% by weight after 18 months of storage. In some embodiments, the impurity with a relative retention time of about 0.74 is about 0.8% by weight after 18 months of storage. In some embodiments, the impurity with a relative retention time of about 0.74 is about 0.7% by weight after 18 months of storage. In some embodiments, the impurity with a relative retention time of about 0.74 is about 0.6% by weight after 18 months of storage. In some embodiments, the impurity with a relative retention time of about 0.74 is about 0.5% by weight after 18 months of storage. In some embodiments, the impurity with a relative retention time of about 0.74 is about 0.4% by weight after 18 months of storage. In some embodiments, the impurity with a relative retention time of about 0.74 is about 0.3% by weight after 18 months of storage. In some embodiments, the impurity with a relative retention time of about 0.74 is about 0.2% by weight after 18 months of storage. In some embodiments, the impurity with a relative retention time of about 0.74 is about 0.1% by weight after 18 months of storage. In some embodiments, the impurity with a relative retention time of about 0.74 is about 0.09% by weight after 18 months of storage. In some embodiments, the impurity with a relative retention time of about 0.74 is about 0.08% by weight after 18 months of storage. In some embodiments, the impurity with a relative retention time of about 0.74 is about 0.07% by weight after 18 months of storage. In some embodiments, the impurity with a relative retention time of about 0.74 is about 0.06% by weight after 18 months of storage. In some embodiments, the impurity with a relative retention time of about 0.74 is about 0.05% by weight after 18 months of storage. In some embodiments, the impurity with a relative retention time of about 0.74 is about 0.04% by weight after 18 months of storage. In some embodiments, the impurity with a relative retention time of about 0.74 is about 0.03% by weight after 18 months of storage. In some embodiments, the impurity with a relative retention time of about 0.74 is about 0.02% by weight after 18 months of storage. In some embodiments, the impurity with a relative retention time of about 0.74 is about 0.01% by weight after 18 months of storage. In some embodiments, the impurity with a relative retention time of about 0.74 is about 0.005% by weight after 18 months of storage. In some embodiments, the impurity with a relative retention time of about 0.74 is about 0.001% by weight after 18 months of storage.

In some embodiments, the impurity with a relative retention time of about 0.74 is from about 1.5% to about 0.001%, about 1.4% to about 0.001%, about 1.3% to about 0.001%, about 1.2% to about 0.001%, about 1.1% to about 0.001%, about 1.0% to about 0.001%, about 0.9% to about 0.001%, about 0.8% to about 0.001%, about 0.7% to about 0.001%, about 0.6% to about 0.001%, about 0.5% to about 0.001%, about 0.4% to about 0.001%, about 0.3% to about 0.001%, about 0.2% to about 0.001%, about 0.1% to about 0.001%, about 0.09% to about 0.001%, about 0.08% to about 0.001%, about 0.07% to about 0.001%, about 0.06% to about 0.001%, about 0.05% to about 0.001%, about 0.04% to about 0.001%, about 0.03% to about 0.001%, about 0.02% to about 0.001%, about 0.01% to about 0.001%, or about 0.005% to about 0.001% by weight after 18 months of storage.

In some embodiments, the impurity with a relative retention time of about 0.74 is from about 1.5% to about 0.01%, about 1.4% to about 0.01%, about 1.3% to about 0.01%, about 1.2% to about 0.01%, about 1.1% to about 0.01%, about 1.0% to about 0.01%, about 0.9% to about 0.01%, about 0.8% to about 0.01%, about 0.7% to about 0.01%, about 0.6% to about 0.01%, about 0.5% to about 0.01%, about 0.4% to about 0.01%, about 0.3% to about 0.01%, about 0.2% to about 0.01%, about 0.1% to about 0.01%, about 0.09% to about 0.01%, about 0.08% to about 0.01%, about 0.07% to about 0.01%, about 0.06% to about 0.01%, about 0.05% to about 0.01%, about 0.04% to about 0.01%, about 0.03% to about 0.01%, or about 0.02% to about 0.01% by weight after 18 months of storage.

In some embodiments, the impurity with a relative retention time of about 0.74 is from about 1.5% to about 0.1%, about 1.4% to about 0.1%, about 1.3% to about 0.1%, about 1.2% to about 0.1%, about 1.1% to about 0.1%, about 1.0% to about 0.1%, about 0.9% to about 0.1%, about 0.8% to about 0.1%, about 0.7% to about 0.1%, about 0.6% to about 0.1%, about 0.5% to about 0.1%, about 0.4% to about 0.1%, about 0.3% to about 0.1%, or about 0.2% to about 0.1% by weight after 18 months of storage.

In some embodiments, the impurity with a relative retention time of about 0.74 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 18 months of storage. In some embodiments, the impurity with a relative retention time of about 0.74 is less than about 1.5% by weight after 18 months of storage. In some embodiments, the impurity with a relative retention time of about 0.74 is less than about 1.4% by weight after 18 months of storage. In some embodiments, the impurity with a relative retention time of about 0.74 is less than about 1.3% by weight after 18 months of storage. In some embodiments, the impurity with a relative retention time of about 0.74 is less than about 1.2% by weight after 18 months of storage. In some embodiments, the impurity with a relative retention time of about 0.74 is less than about 1.1% by weight after 18 months of storage. In some embodiments, the impurity with a relative retention time of about 0.74 is less than about 1.0% by weight after 18 months of storage. In some embodiments, the impurity with a relative retention time of about 0.74 is less than about 0.9% by weight after 18 months of storage. In some embodiments, the impurity with a relative retention time of about 0.74 is less than about 0.8% by weight after 18 months of storage. In some embodiments, the impurity with a relative retention time of about 0.74 is less than about 0.7% by weight after 18 months of storage. In some embodiments, the impurity with a relative retention time of about 0.74 is less than about 0.6% by weight after 18 months of storage. In some embodiments, the impurity with a relative retention time of about 0.74 is less than about 0.5% by weight after 18 months of storage. In some embodiments, the impurity with a relative retention time of about 0.74 is less than about 0.4% by weight after 18 months of storage. In some embodiments, the impurity with a relative retention time of about 0.74 is less than about 0.3% by weight after 18 months of storage. In some embodiments, the impurity with a relative retention time of about 0.74 is less than about 0.2% by weight after 18 months of storage. In some embodiments, the impurity with a relative retention time of about 0.74 is less than about 0.1% by weight after 18 months of storage. In some embodiments, the impurity with a relative retention time of about 0.74 is less than about 0.09% by weight after 18 months of storage. In some embodiments, the impurity with a relative retention time of about 0.74 is less than about 0.08% by weight after 18 months of storage. In some embodiments, the impurity with a relative retention time of about 0.74 is less than about 0.07% by weight after 18 months of storage. In some embodiments, the impurity with a relative retention time of about 0.74 is less than about 0.06% by weight after 18 months of storage. In some embodiments, the impurity with a relative retention time of about 0.74 is less than about 0.05% by weight after 18 months of storage. In some embodiments, the impurity with a relative retention time of about 0.74 is less than about 0.04% by weight after 18 months of storage. In some embodiments, the impurity with a relative retention time of about 0.74 is less than about 0.03% by weight after 18 months of storage. In some embodiments, the impurity with a relative retention time of about 0.74 is less than about 0.02% by weight after 18 months of storage. In some embodiments, the impurity with a relative retention time of about 0.74 is less than about 0.01% by weight after 18 months of storage. In some embodiments, the impurity with a relative retention time of about 0.74 is less than about 0.005% by weight after 18 months of storage. In some embodiments, the impurity with a relative retention time of about 0.74 is less than about 0.001% by weight after 18 months of storage.

In some embodiments, the impurity with a relative retention time of about 0.74 is from less than about 1.5% to about 0.001%, less than about 1.4% to about 0.001%, less than about 1.3% to about 0.001%, less than about 1.2% to about 0.001%, less than about 1.1% to about 0.001%, less than about 1.0% to about 0.001%, less than about 0.9% to about 0.001%, less than about 0.8% to about 0.001%, less than about 0.7% to about 0.001%, less than about 0.6% to about 0.001%, less than about 0.5% to about 0.001%, less than about 0.4% to about 0.001%, less than about 0.3% to about 0.001%, less than about 0.2% to about 0.001%, less than about 0.1% to about 0.001%, less than about 0.09% to about 0.001%, less than about 0.08% to about 0.001%, less than about 0.07% to about 0.001%, less than about 0.06% to about 0.001%, less than about 0.05% to about 0.001%, less than about 0.04% to about 0.001%, less than about 0.03% to about 0.001%, less than about 0.02% to about 0.001%, less than about 0.01% to about 0.001%, or less than about 0.005% to about 0.001% by weight after 18 months of storage.

In some embodiments, the impurity with a relative retention time of about 0.74 is from less than about 1.5% to about 0.01%, less than about 1.4% to about 0.01%, less than about 1.3% to about 0.01%, less than about 1.2% to about 0.01%, less than about 1.1% to about 0.01%, less than about 1.0% to about 0.01%, less than about 0.9% to about 0.01%, less than about 0.8% to about 0.01%, less than about 0.7% to about 0.01%, less than about 0.6% to about 0.01%, less than about 0.5% to about 0.01%, less than about 0.4% to about 0.01%, less than about 0.3% to about 0.01%, less than about 0.2% to about 0.01%, less than about 0.1% to about 0.01%, less than about 0.09% to about 0.01%, less than about 0.08% to about 0.01%, less than about 0.07% to about 0.01%, less than about 0.06% to about 0.01%, less than about 0.05% to about 0.01%, less than about 0.04% to about 0.01%, less than about 0.03% to about 0.01%, or less than about 0.02% to about 0.01% by weight after 18 months of storage.

In some embodiments, the impurity with a relative retention time of about 0.74 is from less than about 1.5% to about 0.1%, less than about 1.4% to about 0.1%, less than about 1.3% to about 0.1%, less than about 1.2% to about 0.1%, less than about 1.1% to about 0.1%, less than about 1.0% to about 0.1%, less than about 0.9% to about 0.1%, less than about 0.8% to about 0.1%, less than about 0.7% to about 0.1%, less than about 0.6% to about 0.1%, less than about 0.5% to about 0.1%, less than about 0.4% to about 0.1%, less than about 0.3% to about 0.1%, or less than about 0.2% to about 0.1% by weight after 18 months of storage.

In some embodiments, the total impurity comprises an impurity with a relative retention time of about 0.79. In some embodiments, the total impurity comprises an impurity with a relative retention time of about 0.79±0.01, about 0.79±0.02, about 0.79±0.03, about 0.79±0.04, about 0.79±0.05, about 0.79±0.06, about 0.79±0.07, about 0.79±0.08, about 0.79±0.09, or about 0.79±0.10.

In some embodiments, the impurity with a relative retention time of about 0.79 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight. In some embodiments, the impurity with a relative retention time of about 0.79 is about 1.5% by weight. In some embodiments, the impurity with a relative retention time of about 0.79 is about 1.4% by weight. In some embodiments, the impurity with a relative retention time of about 0.79 is about 1.3% by weight. In some embodiments, the impurity with a relative retention time of about 0.79 is about 1.2% by weight. In some embodiments, the impurity with a relative retention time of about 0.79 is about 1.1% by weight. In some embodiments, the impurity with a relative retention time of about 0.79 is about 1.0% by weight. In some embodiments, the impurity with a relative retention time of about 0.79 is about 0.9% by weight. In some embodiments, the impurity with a relative retention time of about 0.79 is about 0.8% by weight. In some embodiments, the impurity with a relative retention time of about 0.79 is about 0.7% by weight. In some embodiments, the impurity with a relative retention time of about 0.79 is about 0.6% by weight. In some embodiments, the impurity with a relative retention time of about 0.79 is about 0.5% by weight. In some embodiments, the impurity with a relative retention time of about 0.79 is about 0.4% by weight. In some embodiments, the impurity with a relative retention time of about 0.79 is about 0.3% by weight. In some embodiments, the impurity with a relative retention time of about 0.79 is about 0.2% by weight. In some embodiments, the impurity with a relative retention time of about 0.79 is about 0.1% by weight. In some embodiments, the impurity with a relative retention time of about 0.79 is about 0.09% by weight. In some embodiments, the impurity with a relative retention time of about 0.79 is about 0.08% by weight. In some embodiments, the impurity with a relative retention time of about 0.79 is about 0.07% by weight. In some embodiments, the impurity with a relative retention time of about 0.79 is about 0.06% by weight. In some embodiments, the impurity with a relative retention time of about 0.79 is about 0.05% by weight. In some embodiments, the impurity with a relative retention time of about 0.79 is about 0.04% by weight. In some embodiments, the impurity with a relative retention time of about 0.79 is about 0.03% by weight. In some embodiments, the impurity with a relative retention time of about 0.79 is about 0.02% by weight. In some embodiments, the impurity with a relative retention time of about 0.79 is about 0.01% by weight. In some embodiments, the impurity with a relative retention time of about 0.79 is about 0.005% by weight. In some embodiments, the impurity with a relative retention time of about 0.79 is about 0.001% by weight.

In some embodiments, the impurity with a relative retention time of about 0.79 is from about 1.5% to about 0.001%, about 1.4% to about 0.001%, about 1.3% to about 0.001%, about 1.2% to about 0.001%, about 1.1% to about 0.001%, about 1.0% to about 0.001%, about 0.9% to about 0.001%, about 0.8% to about 0.001%, about 0.7% to about 0.001%, about 0.6% to about 0.001%, about 0.5% to about 0.001%, about 0.4% to about 0.001%, about 0.3% to about 0.001%, about 0.2% to about 0.001%, about 0.1% to about 0.001%, about 0.09% to about 0.001%, about 0.08% to about 0.001%, about 0.07% to about 0.001%, about 0.06% to about 0.001%, about 0.05% to about 0.001%, about 0.04% to about 0.001%, about 0.03% to about 0.001%, about 0.02% to about 0.001%, about 0.01% to about 0.001%, or about 0.005% to about 0.001% by weight.

In some embodiments, the impurity with a relative retention time of about 0.79 is from about 1.5% to about 0.01%, about 1.4% to about 0.01%, about 1.3% to about 0.01%, about 1.2% to about 0.01%, about 1.1% to about 0.01%, about 1.0% to about 0.01%, about 0.9% to about 0.01%, about 0.8% to about 0.01%, about 0.7% to about 0.01%, about 0.6% to about 0.01%, about 0.5% to about 0.01%, about 0.4% to about 0.01%, about 0.3% to about 0.01%, about 0.2% to about 0.01%, about 0.1% to about 0.01%, about 0.09% to about 0.01%, about 0.08% to about 0.01%, about 0.07% to about 0.01%, about 0.06% to about 0.01%, about 0.05% to about 0.01%, about 0.04% to about 0.01%, about 0.03% to about 0.01%, or about 0.02% to about 0.01% by weight.

In some embodiments, the impurity with a relative retention time of about 0.79 is from about 1.5% to about 0.1%, about 1.4% to about 0.1%, about 1.3% to about 0.1%, about 1.2% to about 0.1%, about 1.1% to about 0.1%, about 1.0% to about 0.1%, about 0.9% to about 0.1%, about 0.8% to about 0.1%, about 0.7% to about 0.1%, about 0.6% to about 0.1%, about 0.5% to about 0.1%, about 0.4% to about 0.1%, about 0.3% to about 0.1%, or about 0.2% to about 0.1% by weight.

In some embodiments, the impurity with a relative retention time of about 0.79 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight. In some embodiments, the impurity with a relative retention time of about 0.79 is less than about 1.5% by weight. In some embodiments, the impurity with a relative retention time of about 0.79 is less than about 1.4% by weight. In some embodiments, the impurity with a relative retention time of about 0.79 is less than about 1.3% by weight. In some embodiments, the impurity with a relative retention time of about 0.79 is less than about 1.2% by weight. In some embodiments, the impurity with a relative retention time of about 0.79 is less than about 1.1% by weight. In some embodiments, the impurity with a relative retention time of about 0.79 is less than about 1.0% by weight. In some embodiments, the impurity with a relative retention time of about 0.79 is less than about 0.9% by weight. In some embodiments, the impurity with a relative retention time of about 0.79 is less than about 0.8% by weight. In some embodiments, the impurity with a relative retention time of about 0.79 is less than about 0.7% by weight. In some embodiments, the impurity with a relative retention time of about 0.79 is less than about 0.6% by weight. In some embodiments, the impurity with a relative retention time of about 0.79 is less than about 0.5% by weight. In some embodiments, the impurity with a relative retention time of about 0.79 is less than about 0.4% by weight. In some embodiments, the impurity with a relative retention time of about 0.79 is less than about 0.3% by weight. In some embodiments, the impurity with a relative retention time of about 0.79 is less than about 0.2% by weight. In some embodiments, the impurity with a relative retention time of about 0.79 is less than about 0.1% by weight. In some embodiments, the impurity with a relative retention time of about 0.79 is less than about 0.09% by weight. In some embodiments, the impurity with a relative retention time of about 0.79 is less than about 0.08% by weight. In some embodiments, the impurity with a relative retention time of about 0.79 is less than about 0.07% by weight. In some embodiments, the impurity with a relative retention time of about 0.79 is less than about 0.06% by weight. In some embodiments, the impurity with a relative retention time of about 0.79 is less than about 0.05% by weight. In some embodiments, the impurity with a relative retention time of about 0.79 is less than about 0.04% by weight. In some embodiments, the impurity with a relative retention time of about 0.79 is less than about 0.03% by weight. In some embodiments, the impurity with a relative retention time of about 0.79 is less than about 0.02% by weight. In some embodiments, the impurity with a relative retention time of about 0.79 is less than about 0.01% by weight. In some embodiments, the impurity with a relative retention time of about 0.79 is less than about 0.005% by weight. In some embodiments, the impurity with a relative retention time of about 0.79 is less than about 0.001% by weight.

In some embodiments, the impurity with a relative retention time of about 0.79 is from less than about 1.5% to about 0.001%, less than about 1.4% to about 0.001%, less than about 1.3% to about 0.001%, less than about 1.2% to about 0.001%, less than about 1.1% to about 0.001%, less than about 1.0% to about 0.001%, less than about 0.9% to about 0.001%, less than about 0.8% to about 0.001%, less than about 0.7% to about 0.001%, less than about 0.6% to about 0.001%, less than about 0.5% to about 0.001%, less than about 0.4% to about 0.001%, less than about 0.3% to about 0.001%, less than about 0.2% to about 0.001%, less than about 0.1% to about 0.001%, less than about 0.09% to about 0.001%, less than about 0.08% to about 0.001%, less than about 0.07% to about 0.001%, less than about 0.06% to about 0.001%, less than about 0.05% to about 0.001%, less than about 0.04% to about 0.001%, less than about 0.03% to about 0.001%, less than about 0.02% to about 0.001%, less than about 0.01% to about 0.001%, or less than about 0.005% to about 0.001% by weight.

In some embodiments, the impurity with a relative retention time of about 0.79 is from less than about 1.5% to about 0.01%, less than about 1.4% to about 0.01%, less than about 1.3% to about 0.01%, less than about 1.2% to about 0.01%, less than about 1.1% to about 0.01%, less than about 1.0% to about 0.01%, less than about 0.9% to about 0.01%, less than about 0.8% to about 0.01%, less than about 0.7% to about 0.01%, less than about 0.6% to about 0.01%, less than about 0.5% to about 0.01%, less than about 0.4% to about 0.01%, less than about 0.3% to about 0.01%, less than about 0.2% to about 0.01%, less than about 0.1% to about 0.01%, less than about 0.09% to about 0.01%, less than about 0.08% to about 0.01%, less than about 0.07% to about 0.01%, less than about 0.06% to about 0.01%, less than about 0.05% to about 0.01%, less than about 0.04% to about 0.01%, less than about 0.03% to about 0.01%, or less than about 0.02% to about 0.01% by weight.

In some embodiments, the impurity with a relative retention time of about 0.79 is from less than about 1.5% to about 0.1%, less than about 1.4% to about 0.1%, less than about 1.3% to about 0.1%, less than about 1.2% to about 0.1%, less than about 1.1% to about 0.1%, less than about 1.0% to about 0.1%, less than about 0.9% to about 0.1%, less than about 0.8% to about 0.1%, less than about 0.7% to about 0.1%, less than about 0.6% to about 0.1%, less than about 0.5% to about 0.1%, less than about 0.4% to about 0.1%, less than about 0.3% to about 0.1%, or less than about 0.2% to about 0.1% by weight.

In some embodiments, the impurity with a relative retention time of about 0.79 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 0 months of storage. In some embodiments, the impurity with a relative retention time of about 0.79 is about 1.5% by weight after 0 months of storage. In some embodiments, the impurity with a relative retention time of about 0.79 is about 1.4% by weight after 0 months of storage. In some embodiments, the impurity with a relative retention time of about 0.79 is about 1.3% by weight after 0 months of storage. In some embodiments, the impurity with a relative retention time of about 0.79 is about 1.2% by weight after 0 months of storage. In some embodiments, the impurity with a relative retention time of about 0.79 is about 1.1% by weight after 0 months of storage. In some embodiments, the impurity with a relative retention time of about 0.79 is about 1.0% by weight after 0 months of storage. In some embodiments, the impurity with a relative retention time of about 0.79 is about 0.9% by weight after 0 months of storage. In some embodiments, the impurity with a relative retention time of about 0.79 is about 0.8% by weight after 0 months of storage. In some embodiments, the impurity with a relative retention time of about 0.79 is about 0.7% by weight after 0 months of storage. In some embodiments, the impurity with a relative retention time of about 0.79 is about 0.6% by weight after 0 months of storage. In some embodiments, the impurity with a relative retention time of about 0.79 is about 0.5% by weight after 0 months of storage. In some embodiments, the impurity with a relative retention time of about 0.79 is about 0.4% by weight after 0 months of storage. In some embodiments, the impurity with a relative retention time of about 0.79 is about 0.3% by weight after 0 months of storage. In some embodiments, the impurity with a relative retention time of about 0.79 is about 0.2% by weight after 0 months of storage. In some embodiments, the impurity with a relative retention time of about 0.79 is about 0.1% by weight after 0 months of storage. In some embodiments, the impurity with a relative retention time of about 0.79 is about 0.09% by weight after 0 months of storage. In some embodiments, the impurity with a relative retention time of about 0.79 is about 0.08% by weight after 0 months of storage. In some embodiments, the impurity with a relative retention time of about 0.79 is about 0.07% by weight after 0 months of storage. In some embodiments, the impurity with a relative retention time of about 0.79 is about 0.06% by weight after 0 months of storage. In some embodiments, the impurity with a relative retention time of about 0.79 is about 0.05% by weight after 0 months of storage. In some embodiments, the impurity with a relative retention time of about 0.79 is about 0.04% by weight after 0 months of storage. In some embodiments, the impurity with a relative retention time of about 0.79 is about 0.03% by weight after 0 months of storage. In some embodiments, the impurity with a relative retention time of about 0.79 is about 0.02% by weight after 0 months of storage. In some embodiments, the impurity with a relative retention time of about 0.79 is about 0.01% by weight after 0 months of storage. In some embodiments, the impurity with a relative retention time of about 0.79 is about 0.005% by weight after 0 months of storage. In some embodiments, the impurity with a relative retention time of about 0.79 is about 0.001% by weight after 0 months of storage.

In some embodiments, the impurity with a relative retention time of about 0.79 is from about 1.5% to about 0.001%, about 1.4% to about 0.001%, about 1.3% to about 0.001%, about 1.2% to about 0.001%, about 1.1% to about 0.001%, about 1.0% to about 0.001%, about 0.9% to about 0.001%, about 0.8% to about 0.001%, about 0.7% to about 0.001%, about 0.6% to about 0.001%, about 0.5% to about 0.001%, about 0.4% to about 0.001%, about 0.3% to about 0.001%, about 0.2% to about 0.001%, about 0.1% to about 0.001%, about 0.09% to about 0.001%, about 0.08% to about 0.001%, about 0.07% to about 0.001%, about 0.06% to about 0.001%, about 0.05% to about 0.001%, about 0.04% to about 0.001%, about 0.03% to about 0.001%, about 0.02% to about 0.001%, about 0.01% to about 0.001%, or about 0.005% to about 0.001% by weight after 0 months of storage.

In some embodiments, the impurity with a relative retention time of about 0.79 is from about 1.5% to about 0.01%, about 1.4% to about 0.01%, about 1.3% to about 0.01%, about 1.2% to about 0.01%, about 1.1% to about 0.01%, about 1.0% to about 0.01%, about 0.9% to about 0.01%, about 0.8% to about 0.01%, about 0.7% to about 0.01%, about 0.6% to about 0.01%, about 0.5% to about 0.01%, about 0.4% to about 0.01%, about 0.3% to about 0.01%, about 0.2% to about 0.01%, about 0.1% to about 0.01%, about 0.09% to about 0.01%, about 0.08% to about 0.01%, about 0.07% to about 0.01%, about 0.06% to about 0.01%, about 0.05% to about 0.01%, about 0.04% to about 0.01%, about 0.03% to about 0.01%, or about 0.02% to about 0.01% by weight after 0 months of storage.

In some embodiments, the impurity with a relative retention time of about 0.79 is from about 1.5% to about 0.1%, about 1.4% to about 0.1%, about 1.3% to about 0.1%, about 1.2% to about 0.1%, about 1.1% to about 0.1%, about 1.0% to about 0.1%, about 0.9% to about 0.1%, about 0.8% to about 0.1%, about 0.7% to about 0.1%, about 0.6% to about 0.1%, about 0.5% to about 0.1%, about 0.4% to about 0.1%, about 0.3% to about 0.1%, or about 0.2% to about 0.1% by weight after 0 months of storage.

In some embodiments, the impurity with a relative retention time of about 0.79 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 0 months of storage. In some embodiments, the impurity with a relative retention time of about 0.79 is less than about 1.5% by weight after 0 months of storage. In some embodiments, the impurity with a relative retention time of about 0.79 is less than about 1.4% by weight after 0 months of storage. In some embodiments, the impurity with a relative retention time of about 0.79 is less than about 1.3% by weight after 0 months of storage. In some embodiments, the impurity with a relative retention time of about 0.79 is less than about 1.2% by weight after 0 months of storage. In some embodiments, the impurity with a relative retention time of about 0.79 is less than about 1.1% by weight after 0 months of storage. In some embodiments, the impurity with a relative retention time of about 0.79 is less than about 1.0% by weight after 0 months of storage. In some embodiments, the impurity with a relative retention time of about 0.79 is less than about 0.9% by weight after 0 months of storage. In some embodiments, the impurity with a relative retention time of about 0.79 is less than about 0.8% by weight after 0 months of storage. In some embodiments, the impurity with a relative retention time of about 0.79 is less than about 0.7% by weight after 0 months of storage. In some embodiments, the impurity with a relative retention time of about 0.79 is less than about 0.6% by weight after 0 months of storage. In some embodiments, the impurity with a relative retention time of about 0.79 is less than about 0.5% by weight after 0 months of storage. In some embodiments, the impurity with a relative retention time of about 0.79 is less than about 0.4% by weight after 0 months of storage. In some embodiments, the impurity with a relative retention time of about 0.79 is less than about 0.3% by weight after 0 months of storage. In some embodiments, the impurity with a relative retention time of about 0.79 is less than about 0.2% by weight after 0 months of storage. In some embodiments, the impurity with a relative retention time of about 0.79 is less than about 0.1% by weight after 0 months of storage. In some embodiments, the impurity with a relative retention time of about 0.79 is less than about 0.09% by weight after 0 months of storage. In some embodiments, the impurity with a relative retention time of about 0.79 is less than about 0.08% by weight after 0 months of storage. In some embodiments, the impurity with a relative retention time of about 0.79 is less than about 0.07% by weight after 0 months of storage. In some embodiments, the impurity with a relative retention time of about 0.79 is less than about 0.06% by weight after 0 months of storage. In some embodiments, the impurity with a relative retention time of about 0.79 is less than about 0.05% by weight after 0 months of storage. In some embodiments, the impurity with a relative retention time of about 0.79 is less than about 0.04% by weight after 0 months of storage. In some embodiments, the impurity with a relative retention time of about 0.79 is less than about 0.03% by weight after 0 months of storage. In some embodiments, the impurity with a relative retention time of about 0.79 is less than about 0.02% by weight after 0 months of storage. In some embodiments, the impurity with a relative retention time of about 0.79 is less than about 0.01% by weight after 0 months of storage. In some embodiments, the impurity with a relative retention time of about 0.79 is less than about 0.005% by weight after 0 months of storage. In some embodiments, the impurity with a relative retention time of about 0.79 is less than about 0.001% by weight after 0 months of storage.

In some embodiments, the impurity with a relative retention time of about 0.79 is from less than about 1.5% to about 0.001%, less than about 1.4% to about 0.001%, less than about 1.3% to about 0.001%, less than about 1.2% to about 0.001%, less than about 1.1% to about 0.001%, less than about 1.0% to about 0.001%, less than about 0.9% to about 0.001%, less than about 0.8% to about 0.001%, less than about 0.7% to about 0.001%, less than about 0.6% to about 0.001%, less than about 0.5% to about 0.001%, less than about 0.4% to about 0.001%, less than about 0.3% to about 0.001%, less than about 0.2% to about 0.001%, less than about 0.1% to about 0.001%, less than about 0.09% to about 0.001%, less than about 0.08% to about 0.001%, less than about 0.07% to about 0.001%, less than about 0.06% to about 0.001%, less than about 0.05% to about 0.001%, less than about 0.04% to about 0.001%, less than about 0.03% to about 0.001%, less than about 0.02% to about 0.001%, less than about 0.01% to about 0.001%, or less than about 0.005% to about 0.001% by weight after 0 months of storage.

In some embodiments, the impurity with a relative retention time of about 0.79 is from less than about 1.5% to about 0.01%, less than about 1.4% to about 0.01%, less than about 1.3% to about 0.01%, less than about 1.2% to about 0.01%, less than about 1.1% to about 0.01%, less than about 1.0% to about 0.01%, less than about 0.9% to about 0.01%, less than about 0.8% to about 0.01%, less than about 0.7% to about 0.01%, less than about 0.6% to about 0.01%, less than about 0.5% to about 0.01%, less than about 0.4% to about 0.01%, less than about 0.3% to about 0.01%, less than about 0.2% to about 0.01%, less than about 0.1% to about 0.01%, less than about 0.09% to about 0.01%, less than about 0.08% to about 0.01%, less than about 0.07% to about 0.01%, less than about 0.06% to about 0.01%, less than about 0.05% to about 0.01%, less than about 0.04% to about 0.01%, less than about 0.03% to about 0.01%, or less than about 0.02% to about 0.01% by weight after 0 months of storage.

In some embodiments, the impurity with a relative retention time of about 0.79 is from less than about 1.5% to about 0.1%, less than about 1.4% to about 0.1%, less than about 1.3% to about 0.1%, less than about 1.2% to about 0.1%, less than about 1.1% to about 0.1%, less than about 1.0% to about 0.1%, less than about 0.9% to about 0.1%, less than about 0.8% to about 0.1%, less than about 0.7% to about 0.1%, less than about 0.6% to about 0.1%, less than about 0.5% to about 0.1%, less than about 0.4% to about 0.1%, less than about 0.3% to about 0.1%, or less than about 0.2% to about 0.1% by weight after 0 months of storage.

In some embodiments, the impurity with a relative retention time of about 0.79 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 12 months of storage. In some embodiments, the impurity with a relative retention time of about 0.79 is about 1.5% by weight after 12 months of storage. In some embodiments, the impurity with a relative retention time of about 0.79 is about 1.4% by weight after 12 months of storage. In some embodiments, the impurity with a relative retention time of about 0.79 is about 1.3% by weight after 12 months of storage. In some embodiments, the impurity with a relative retention time of about 0.79 is about 1.2% by weight after 12 months of storage. In some embodiments, the impurity with a relative retention time of about 0.79 is about 1.1% by weight after 12 months of storage. In some embodiments, the impurity with a relative retention time of about 0.79 is about 1.0% by weight after 12 months of storage. In some embodiments, the impurity with a relative retention time of about 0.79 is about 0.9% by weight after 12 months of storage. In some embodiments, the impurity with a relative retention time of about 0.79 is about 0.8% by weight after 12 months of storage. In some embodiments, the impurity with a relative retention time of about 0.79 is about 0.7% by weight after 12 months of storage. In some embodiments, the impurity with a relative retention time of about 0.79 is about 0.6% by weight after 12 months of storage. In some embodiments, the impurity with a relative retention time of about 0.79 is about 0.5% by weight after 12 months of storage. In some embodiments, the impurity with a relative retention time of about 0.79 is about 0.4% by weight after 12 months of storage. In some embodiments, the impurity with a relative retention time of about 0.79 is about 0.3% by weight after 12 months of storage. In some embodiments, the impurity with a relative retention time of about 0.79 is about 0.2% by weight after 12 months of storage. In some embodiments, the impurity with a relative retention time of about 0.79 is about 0.1% by weight after 12 months of storage. In some embodiments, the impurity with a relative retention time of about 0.79 is about 0.09% by weight after 12 months of storage. In some embodiments, the impurity with a relative retention time of about 0.79 is about 0.08% by weight after 12 months of storage. In some embodiments, the impurity with a relative retention time of about 0.79 is about 0.07% by weight after 12 months of storage. In some embodiments, the impurity with a relative retention time of about 0.79 is about 0.06% by weight after 12 months of storage. In some embodiments, the impurity with a relative retention time of about 0.79 is about 0.05% by weight after 12 months of storage. In some embodiments, the impurity with a relative retention time of about 0.79 is about 0.04% by weight after 12 months of storage. In some embodiments, the impurity with a relative retention time of about 0.79 is about 0.03% by weight after 12 months of storage. In some embodiments, the impurity with a relative retention time of about 0.79 is about 0.02% by weight after 12 months of storage. In some embodiments, the impurity with a relative retention time of about 0.79 is about 0.01% by weight after 12 months of storage. In some embodiments, the impurity with a relative retention time of about 0.79 is about 0.005% by weight after 12 months of storage. In some embodiments, the impurity with a relative retention time of about 0.79 is about 0.001% by weight after 12 months of storage.

In some embodiments, the impurity with a relative retention time of about 0.79 is from about 1.5% to about 0.001%, about 1.4% to about 0.001%, about 1.3% to about 0.001%, about 1.2% to about 0.001%, about 1.1% to about 0.001%, about 1.0% to about 0.001%, about 0.9% to about 0.001%, about 0.8% to about 0.001%, about 0.7% to about 0.001%, about 0.6% to about 0.001%, about 0.5% to about 0.001%, about 0.4% to about 0.001%, about 0.3% to about 0.001%, about 0.2% to about 0.001%, about 0.1% to about 0.001%, about 0.09% to about 0.001%, about 0.08% to about 0.001%, about 0.07% to about 0.001%, about 0.06% to about 0.001%, about 0.05% to about 0.001%, about 0.04% to about 0.001%, about 0.03% to about 0.001%, about 0.02% to about 0.001%, about 0.01% to about 0.001%, or about 0.005% to about 0.001% by weight after 12 months of storage.

In some embodiments, the impurity with a relative retention time of about 0.79 is from about 1.5% to about 0.01%, about 1.4% to about 0.01%, about 1.3% to about 0.01%, about 1.2% to about 0.01%, about 1.1% to about 0.01%, about 1.0% to about 0.01%, about 0.9% to about 0.01%, about 0.8% to about 0.01%, about 0.7% to about 0.01%, about 0.6% to about 0.01%, about 0.5% to about 0.01%, about 0.4% to about 0.01%, about 0.3% to about 0.01%, about 0.2% to about 0.01%, about 0.1% to about 0.01%, about 0.09% to about 0.01%, about 0.08% to about 0.01%, about 0.07% to about 0.01%, about 0.06% to about 0.01%, about 0.05% to about 0.01%, about 0.04% to about 0.01%, about 0.03% to about 0.01%, or about 0.02% to about 0.01% by weight after 12 months of storage.

In some embodiments, the impurity with a relative retention time of about 0.79 is from about 1.5% to about 0.1%, about 1.4% to about 0.1%, about 1.3% to about 0.1%, about 1.2% to about 0.1%, about 1.1% to about 0.1%, about 1.0% to about 0.1%, about 0.9% to about 0.1%, about 0.8% to about 0.1%, about 0.7% to about 0.1%, about 0.6% to about 0.1%, about 0.5% to about 0.1%, about 0.4% to about 0.1%, about 0.3% to about 0.1%, or about 0.2% to about 0.1% by weight after 12 months of storage.

In some embodiments, the impurity with a relative retention time of about 0.79 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 12 months of storage.

In some embodiments, the impurity with a relative retention time of about 0.79 is less than about 1.5% by weight after 12 months of storage. In some embodiments, the impurity with a relative retention time of about 0.79 is less than about 1.4% by weight after 12 months of storage. In some embodiments, the impurity with a relative retention time of about 0.79 is less than about 1.3% by weight after 12 months of storage. In some embodiments, the impurity with a relative retention time of about 0.79 is less than about 1.2% by weight after 12 months of storage. In some embodiments, the impurity with a relative retention time of about 0.79 is less than about 1.1% by weight after 12 months of storage. In some embodiments, the impurity with a relative retention time of about 0.79 is less than about 1.0% by weight after 12 months of storage. In some embodiments, the impurity with a relative retention time of about 0.79 is less than about 0.9% by weight after 12 months of storage. In some embodiments, the impurity with a relative retention time of about 0.79 is less than about 0.8% by weight after 12 months of storage. In some embodiments, the impurity with a relative retention time of about 0.79 is less than about 0.7% by weight after 12 months of storage. In some embodiments, the impurity with a relative retention time of about 0.79 is less than about 0.6% by weight after 12 months of storage. In some embodiments, the impurity with a relative retention time of about 0.79 is less than about 0.5% by weight after 12 months of storage. In some embodiments, the impurity with a relative retention time of about 0.79 is less than about 0.4% by weight after 12 months of storage. In some embodiments, the impurity with a relative retention time of about 0.79 is less than about 0.3% by weight after 12 months of storage. In some embodiments, the impurity with a relative retention time of about 0.79 is less than about 0.2% by weight after 12 months of storage. In some embodiments, the impurity with a relative retention time of about 0.79 is less than about 0.1% by weight after 12 months of storage. In some embodiments, the impurity with a relative retention time of about 0.79 is less than about 0.09% by weight after 12 months of storage. In some embodiments, the impurity with a relative retention time of about 0.79 is less than about 0.08% by weight after 12 months of storage. In some embodiments, the impurity with a relative retention time of about 0.79 is less than about 0.07% by weight after 12 months of storage. In some embodiments, the impurity with a relative retention time of about 0.79 is less than about 0.06% by weight after 12 months of storage. In some embodiments, the impurity with a relative retention time of about 0.79 is less than about 0.05% by weight after 12 months of storage. In some embodiments, the impurity with a relative retention time of about 0.79 is less than about 0.04% by weight after 12 months of storage. In some embodiments, the impurity with a relative retention time of about 0.79 is less than about 0.03% by weight after 12 months of storage. In some embodiments, the impurity with a relative retention time of about 0.79 is less than about 0.02% by weight after 12 months of storage. In some embodiments, the impurity with a relative retention time of about 0.79 is less than about 0.01% by weight after 12 months of storage. In some embodiments, the impurity with a relative retention time of about 0.79 is less than about 0.005% by weight after 12 months of storage. In some embodiments, the impurity with a relative retention time of about 0.79 is less than about 0.001% by weight after 12 months of storage.

In some embodiments, the impurity with a relative retention time of about 0.79 is from less than about 1.5% to about 0.001%, less than about 1.4% to about 0.001%, less than about 1.3% to about 0.001%, less than about 1.2% to about 0.001%, less than about 1.1% to about 0.001%, less than about 1.0% to about 0.001%, less than about 0.9% to about 0.001%, less than about 0.8% to about 0.001%, less than about 0.7% to about 0.001%, less than about 0.6% to about 0.001%, less than about 0.5% to about 0.001%, less than about 0.4% to about 0.001%, less than about 0.3% to about 0.001%, less than about 0.2% to about 0.001%, less than about 0.1% to about 0.001%, less than about 0.09% to about 0.001%, less than about 0.08% to about 0.001%, less than about 0.07% to about 0.001%, less than about 0.06% to about 0.001%, less than about 0.05% to about 0.001%, less than about 0.04% to about 0.001%, less than about 0.03% to about 0.001%, less than about 0.02% to about 0.001%, less than about 0.01% to about 0.001%, or less than about 0.005% to about 0.001% by weight after 12 months of storage.

In some embodiments, the impurity with a relative retention time of about 0.79 is from less than about 1.5% to about 0.01%, less than about 1.4% to about 0.01%, less than about 1.3% to about 0.01%, less than about 1.2% to about 0.01%, less than about 1.1% to about 0.01%, less than about 1.0% to about 0.01%, less than about 0.9% to about 0.01%, less than about 0.8% to about 0.01%, less than about 0.7% to about 0.01%, less than about 0.6% to about 0.01%, less than about 0.5% to about 0.01%, less than about 0.4% to about 0.01%, less than about 0.3% to about 0.01%, less than about 0.2% to about 0.01%, less than about 0.1% to about 0.01%, less than about 0.09% to about 0.01%, less than about 0.08% to about 0.01%, less than about 0.07% to about 0.01%, less than about 0.06% to about 0.01%, less than about 0.05% to about 0.01%, less than about 0.04% to about 0.01%, less than about 0.03% to about 0.01%, or less than about 0.02% to about 0.01% by weight after 12 months of storage.

In some embodiments, the impurity with a relative retention time of about 0.79 is from less than about 1.5% to about 0.1%, less than about 1.4% to about 0.1%, less than about 1.3% to about 0.1%, less than about 1.2% to about 0.1%, less than about 1.1% to about 0.1%, less than about 1.0% to about 0.1%, less than about 0.9% to about 0.1%, less than about 0.8% to about 0.1%, less than about 0.7% to about 0.1%, less than about 0.6% to about 0.1%, less than about 0.5% to about 0.1%, less than about 0.4% to about 0.1%, less than about 0.3% to about 0.1%, or less than about 0.2% to about 0.1% by weight after 12 months of storage.

In some embodiments, the impurity with a relative retention time of about 0.79 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 18 months of storage. In some embodiments, the impurity with a relative retention time of about 0.79 is about 1.5% by weight after 18 months of storage. In some embodiments, the impurity with a relative retention time of about 0.79 is about 1.4% by weight after 18 months of storage. In some embodiments, the impurity with a relative retention time of about 0.79 is about 1.3% by weight after 18 months of storage. In some embodiments, the impurity with a relative retention time of about 0.79 is about 1.2% by weight after 18 months of storage. In some embodiments, the impurity with a relative retention time of about 0.79 is about 1.1% by weight after 18 months of storage. In some embodiments, the impurity with a relative retention time of about 0.79 is about 1.0% by weight after 18 months of storage. In some embodiments, the impurity with a relative retention time of about 0.79 is about 0.9% by weight after 18 months of storage. In some embodiments, the impurity with a relative retention time of about 0.79 is about 0.8% by weight after 18 months of storage. In some embodiments, the impurity with a relative retention time of about 0.79 is about 0.7% by weight after 18 months of storage. In some embodiments, the impurity with a relative retention time of about 0.79 is about 0.6% by weight after 18 months of storage. In some embodiments, the impurity with a relative retention time of about 0.79 is about 0.5% by weight after 18 months of storage. In some embodiments, the impurity with a relative retention time of about 0.79 is about 0.4% by weight after 18 months of storage. In some embodiments, the impurity with a relative retention time of about 0.79 is about 0.3% by weight after 18 months of storage. In some embodiments, the impurity with a relative retention time of about 0.79 is about 0.2% by weight after 18 months of storage. In some embodiments, the impurity with a relative retention time of about 0.79 is about 0.1% by weight after 18 months of storage. In some embodiments, the impurity with a relative retention time of about 0.79 is about 0.09% by weight after 18 months of storage. In some embodiments, the impurity with a relative retention time of about 0.79 is about 0.08% by weight after 18 months of storage. In some embodiments, the impurity with a relative retention time of about 0.79 is about 0.07% by weight after 18 months of storage. In some embodiments, the impurity with a relative retention time of about 0.79 is about 0.06% by weight after 18 months of storage. In some embodiments, the impurity with a relative retention time of about 0.79 is about 0.05% by weight after 18 months of storage. In some embodiments, the impurity with a relative retention time of about 0.79 is about 0.04% by weight after 18 months of storage. In some embodiments, the impurity with a relative retention time of about 0.79 is about 0.03% by weight after 18 months of storage. In some embodiments, the impurity with a relative retention time of about 0.79 is about 0.02% by weight after 18 months of storage. In some embodiments, the impurity with a relative retention time of about 0.79 is about 0.01% by weight after 18 months of storage. In some embodiments, the impurity with a relative retention time of about 0.79 is about 0.005% by weight after 18 months of storage. In some embodiments, the impurity with a relative retention time of about 0.79 is about 0.001% by weight after 18 months of storage.

In some embodiments, the impurity with a relative retention time of about 0.79 is from about 1.5% to about 0.001%, about 1.4% to about 0.001%, about 1.3% to about 0.001%, about 1.2% to about 0.001%, about 1.1% to about 0.001%, about 1.0% to about 0.001%, about 0.9% to about 0.001%, about 0.8% to about 0.001%, about 0.7% to about 0.001%, about 0.6% to about 0.001%, about 0.5% to about 0.001%, about 0.4% to about 0.001%, about 0.3% to about 0.001%, about 0.2% to about 0.001%, about 0.1% to about 0.001%, about 0.09% to about 0.001%, about 0.08% to about 0.001%, about 0.07% to about 0.001%, about 0.06% to about 0.001%, about 0.05% to about 0.001%, about 0.04% to about 0.001%, about 0.03% to about 0.001%, about 0.02% to about 0.001%, about 0.01% to about 0.001%, or about 0.005 to about 0.001% by weight after 18 months of storage.

In some embodiments, the impurity with a relative retention time of about 0.79 is from about 1.5% to about 0.01%, about 1.4% to about 0.01%, about 1.3% to about 0.01%, about 1.2% to about 0.01%, about 1.1% to about 0.01%, about 1.0% to about 0.01%, about 0.9% to about 0.01%, about 0.8% to about 0.01%, about 0.7% to about 0.01%, about 0.6% to about 0.01%, about 0.5% to about 0.01%, about 0.4% to about 0.01%, about 0.3% to about 0.01%, about 0.2% to about 0.01%, about 0.1% to about 0.01%, about 0.09% to about 0.01%, about 0.08% to about 0.01%, about 0.07% to about 0.01%, about 0.06% to about 0.01%, about 0.05% to about 0.01%, about 0.04% to about 0.01%, about 0.03% to about 0.01%, or about 0.02% to about 0.01% by weight after 18 months of storage.

In some embodiments, the impurity with a relative retention time of about 0.79 is from about 1.5% to about 0.1%, about 1.4% to about 0.1%, about 1.3% to about 0.1%, about 1.2% to about 0.1%, about 1.1% to about 0.1%, about 1.0% to about 0.1%, about 0.9% to about 0.1%, about 0.8% to about 0.1%, about 0.7% to about 0.1%, about 0.6% to about 0.1%, about 0.5% to about 0.1%, about 0.4% to about 0.1%, about 0.3% to about 0.1%, or about 0.2% to about 0.1% by weight after 18 months of storage.

In some embodiments, the impurity with a relative retention time of about 0.79 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 18 months of storage. In some embodiments, the impurity with a relative retention time of about 0.79 is less than about 1.5% by weight after 18 months of storage. In some embodiments, the impurity with a relative retention time of about 0.79 is less than about 1.4% by weight after 18 months of storage. In some embodiments, the impurity with a relative retention time of about 0.79 is less than about 1.3% by weight after 18 months of storage. In some embodiments, the impurity with a relative retention time of about 0.79 is less than about 1.2% by weight after 18 months of storage. In some embodiments, the impurity with a relative retention time of about 0.79 is less than about 1.1% by weight after 18 months of storage. In some embodiments, the impurity with a relative retention time of about 0.79 is less than about 1.0% by weight after 18 months of storage. In some embodiments, the impurity with a relative retention time of about 0.79 is less than about 0.9% by weight after 18 months of storage. In some embodiments, the impurity with a relative retention time of about 0.79 is less than about 0.8% by weight after 18 months of storage. In some embodiments, the impurity with a relative retention time of about 0.79 is less than about 0.7% by weight after 18 months of storage. In some embodiments, the impurity with a relative retention time of about 0.79 is less than about 0.6% by weight after 18 months of storage. In some embodiments, the impurity with a relative retention time of about 0.79 is less than about 0.5% by weight after 18 months of storage. In some embodiments, the impurity with a relative retention time of about 0.79 is less than about 0.4% by weight after 18 months of storage. In some embodiments, the impurity with a relative retention time of about 0.79 is less than about 0.3% by weight after 18 months of storage. In some embodiments, the impurity with a relative retention time of about 0.79 is less than about 0.2% by weight after 18 months of storage. In some embodiments, the impurity with a relative retention time of about 0.79 is less than about 0.1% by weight after 18 months of storage. In some embodiments, the impurity with a relative retention time of about 0.79 is less than about 0.09% by weight after 18 months of storage. In some embodiments, the impurity with a relative retention time of about 0.79 is less than about 0.08% by weight after 18 months of storage. In some embodiments, the impurity with a relative retention time of about 0.79 is less than about 0.07% by weight after 18 months of storage. In some embodiments, the impurity with a relative retention time of about 0.79 is less than about 0.06% by weight after 18 months of storage. In some embodiments, the impurity with a relative retention time of about 0.79 is less than about 0.05% by weight after 18 months of storage. In some embodiments, the impurity with a relative retention time of about 0.79 is less than about 0.04% by weight after 18 months of storage. In some embodiments, the impurity with a relative retention time of about 0.79 is less than about 0.03% by weight after 18 months of storage. In some embodiments, the impurity with a relative retention time of about 0.79 is less than about 0.02% by weight after 18 months of storage. In some embodiments, the impurity with a relative retention time of about 0.79 is less than about 0.01% by weight after 18 months of storage. In some embodiments, the impurity with a relative retention time of about 0.79 is less than about 0.005% by weight after 18 months of storage. In some embodiments, the impurity with a relative retention time of about 0.79 is less than about 0.001% by weight after 18 months of storage.

In some embodiments, the impurity with a relative retention time of about 0.79 is from less than about 1.5% to about 0.001%, less than about 1.4% to about 0.001%, less than about 1.3% to about 0.001%, less than about 1.2% to about 0.001%, less than about 1.1% to about 0.001%, less than about 1.0% to about 0.001%, less than about 0.9% to about 0.001%, less than about 0.8% to about 0.001%, less than about 0.7% to about 0.001%, less than about 0.6% to about 0.001%, less than about 0.5% to about 0.001%, less than about 0.4% to about 0.001%, less than about 0.3% to about 0.001%, less than about 0.2% to about 0.001%, less than about 0.1% to about 0.001%, less than about 0.09% to about 0.001%, less than about 0.08% to about 0.001%, less than about 0.07% to about 0.001%, less than about 0.06% to about 0.001%, less than about 0.05% to about 0.001%, less than about 0.04% to about 0.001%, less than about 0.03% to about 0.001%, less than about 0.02% to about 0.001%, less than about 0.01% to about 0.001%, or less than about 0.005% to about 0.001% by weight after 18 months of storage.

In some embodiments, the impurity with a relative retention time of about 0.79 is from less than about 1.5% to about 0.01%, less than about 1.4% to about 0.01%, less than about 1.3% to about 0.01%, less than about 1.2% to about 0.01%, less than about 1.1% to about 0.01%, less than about 1.0% to about 0.01%, less than about 0.9% to about 0.01%, less than about 0.8% to about 0.01%, less than about 0.7% to about 0.01%, less than about 0.6% to about 0.01%, less than about 0.5% to about 0.01%, less than about 0.4% to about 0.01%, less than about 0.3% to about 0.01%, less than about 0.2% to about 0.01%, less than about 0.1% to about 0.01%, less than about 0.09% to about 0.01%, less than about 0.08% to about 0.01%, less than about 0.07% to about 0.01%, less than about 0.06% to about 0.01%, less than about 0.05% to about 0.01%, less than about 0.04% to about 0.01%, less than about 0.03% to about 0.01%, or less than about 0.02% to about 0.01% by weight after 18 months of storage.

In some embodiments, the impurity with a relative retention time of about 0.79 is from less than about 1.5% to about 0.1%, less than about 1.4% to about 0.1%, less than about 1.3% to about 0.1%, less than about 1.2% to about 0.1%, less than about 1.1% to about 0.1%, less than about 1.0% to about 0.1%, less than about 0.9% to about 0.1%, less than about 0.8% to about 0.1%, less than about 0.7% to about 0.1%, less than about 0.6% to about 0.1%, less than about 0.5% to about 0.1%, less than about 0.4% to about 0.1%, less than about 0.3% to about 0.1%, or less than about 0.2% to about 0.1% by weight after 18 months of storage.

In some embodiments, the total impurity comprises one or more impurities with a specific relative retention time. In some embodiments, the specific relative retention time is any one of the retention times shown in Tables 5-7. In some embodiments, the specific relative retention time is about 0.33, about 0.36, about 0.43, about 0.50, about 0.54, about 0.59, about 0.63, about 0.68, about 0.74, about 0.79, about 0.85, about 0.91, about 1.15, about 1.34, about 1.62, or about 1.71. In some embodiments, the specific relative retention time has a range of about ±0.01, about ±0.02, about ±0.03, about ±0.04, about ±0.05, about ±0.06, about ±0.07, about ±0.08, about ±0.09, or about ±0.10.

In some embodiments, the impurity with a specific relative retention time is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 0 months, 12 months, or 18 months of storage. In some embodiments, the impurity with a specific relative retention time is about 1.5% by weight after 0 months, 12 months, or 18 months of storage. In some embodiments, the impurity with a specific relative retention time is about 1.4% by weight after 0 months, 12 months, or 18 months of storage. In some embodiments, the impurity with a specific relative retention time is about 1.3% by weight after 0 months, 12 months, or 18 months of storage. In some embodiments, the impurity with a specific relative retention time is about 1.2% by weight after 0 months, 12 months, or 18 months of storage. In some embodiments, the impurity with a specific relative retention time is about 1.1% by weight after 0 months, 12 months, or 18 months of storage. In some embodiments, the impurity with a specific relative retention time is about 1.0% by weight after 0 months, 12 months, or 18 months of storage. In some embodiments, the impurity with a specific relative retention time is about 0.9% by weight after 0 months, 12 months, or 18 months of storage. In some embodiments, the impurity with a specific relative retention time is about 0.8% by weight after 0 months, 12 months, or 18 months of storage. In some embodiments, the impurity with a specific relative retention time is about 0.7% by weight after 0 months, 12 months, or 18 months of storage. In some embodiments, the impurity with a specific relative retention time is about 0.6% by weight after 0 months, 12 months, or 18 months of storage. In some embodiments, the impurity with a specific relative retention time is about 0.5% by weight after 0 months, 12 months, or 18 months of storage. In some embodiments, the impurity with a specific relative retention time is about 0.4% by weight after 0 months, 12 months, or 18 months of storage. In some embodiments, the impurity a specific relative retention time is about 0.3% by weight after 0 months, 12 months, or 18 months of storage. In some embodiments, the impurity a specific relative retention time is about 0.2% by weight after 0 months, 12 months, or 18 months of storage. In some embodiments, the impurity a specific relative retention time is about 0.1% by weight after 0 months, 12 months, or 18 months of storage. In some embodiments, the impurity a specific relative retention time is about 0.09% by weight after 0 months, 12 months, or 18 months of storage. In some embodiments, the impurity a specific relative retention time is about 0.08% by weight after 0 months, 12 months, or 18 months of storage. In some embodiments, the impurity a specific relative retention time is about 0.07% by weight after 0 months, 12 months, or 18 months of storage. In some embodiments, the impurity a specific relative retention time is about 0.06% by weight after 0 months, 12 months, or 18 months of storage. In some embodiments, the impurity a specific relative retention time is about 0.05% by weight after 0 months, 12 months, or 18 months of storage. In some embodiments, the impurity a specific relative retention time is about 0.04% by weight after 0 months, 12 months, or 18 months of storage. In some embodiments, the impurity a specific relative retention time is about 0.03% by weight after 0 months, 12 months, or 18 months of storage. In some embodiments, the impurity a specific relative retention time is about 0.02% by weight after 0 months, 12 months, or 18 months of storage. In some embodiments, the impurity a specific relative retention time is about 0.01% by weight after 0 months, 12 months, or 18 months of storage. In some embodiments, the impurity a specific relative retention time is about 0.005% by weight after 0 months, 12 months, or 18 months of storage. In some embodiments, the impurity a specific relative retention time is about 0.001% by weight after 0 months, 12 months, or 18 months of storage.

In some embodiments, the impurity a specific relative retention time is from about 1.5% to about 0.001%, about 1.4% to about 0.001%, about 1.3% to about 0.001%, about 1.2% to about 0.001%, about 1.1% to about 0.001%, about 1.0% to about 0.001%, about 0.9% to about 0.001%, about 0.8% to about 0.001%, about 0.7% to about 0.001%, about 0.6% to about 0.001%, about 0.5% to about 0.001%, about 0.4% to about 0.001%, about 0.3% to about 0.001%, about 0.2% to about 0.001%, about 0.1% to about 0.001%, about 0.09% to about 0.001%, about 0.08% to about 0.001%, about 0.07% to about 0.001%, about 0.06% to about 0.001%, about 0.05% to about 0.001%, about 0.04% to about 0.001%, about 0.03% to about 0.001%, about 0.02% to about 0.001%, about 0.01% to about 0.001%, or about 0.005% to about 0.001% by weight after 0 months, 12 months, or 18 months of storage.

In some embodiments, the impurity a specific relative retention time is from about 1.5% to about 0.01%, about 1.4% to about 0.01%, about 1.3% to about 0.01%, about 1.2% to about 0.01%, about 1.1% to about 0.01%, about 1.0% to about 0.01%, about 0.9% to about 0.01%, about 0.8% to about 0.01%, about 0.7% to about 0.01%, about 0.6% to about 0.01%, about 0.5% to about 0.01%, about 0.4% to about 0.01%, about 0.3% to about 0.01%, about 0.2% to about 0.01%, about 0.1% to about 0.01%, about 0.09% to about 0.01%, about 0.08% to about 0.01%, about 0.07% to about 0.01%, about 0.06% to about 0.01%, about 0.05% to about 0.01%, about 0.04% to about 0.01%, about 0.03% to about 0.01%, or about 0.02% to about 0.01% by weight after 0 months, 12 months, or 18 months of storage.

In some embodiments, the impurity a specific relative retention time is from about 1.5% to about 0.1%, about 1.4% to about 0.1%, about 1.3% to about 0.1%, about 1.2% to about 0.1%, about 1.1% to about 0.1%, about 1.0% to about 0.1%, about 0.9% to about 0.1%, about 0.8% to about 0.1%, about 0.7% to about 0.1%, about 0.6% to about 0.1%, about 0.5% to about 0.1%, about 0.4% to about 0.1%, about 0.3% to about 0.1%, or about 0.2% to about 0.1% by weight after 0 months, 12 months, or 18 months of storage.

In some embodiments, the impurity a specific relative retention time is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 0 months, 12 months, or 18 months of storage. In some embodiments, the impurity a specific relative retention time is less than about 1.5% by weight after 0 months, 12 months, or 18 months of storage. In some embodiments, the impurity a specific relative retention time is less than about 1.4% by weight after 0 months, 12 months, or 18 months of storage. In some embodiments, the impurity a specific relative retention time is less than about 1.3% by weight after 0 months, 12 months, or 18 months of storage. In some embodiments, the impurity a specific relative retention time is less than about 1.2% by weight after 0 months, 12 months, or 18 months of storage. In some embodiments, the impurity a specific relative retention time is less than about 1.1% by weight after 0 months, 12 months, or 18 months of storage. In some embodiments, the impurity a specific relative retention time is less than about 1.0% by weight after 0 months, 12 months, or 18 months of storage. In some embodiments, the impurity a specific relative retention time is less than about 0.9% by weight after 0 months, 12 months, or 18 months of storage. In some embodiments, the impurity a specific relative retention time is less than about 0.8% by weight after 0 months, 12 months, or 18 months of storage. In some embodiments, the impurity a specific relative retention time is less than about 0.7% by weight after 0 months, 12 months, or 18 months of storage. In some embodiments, the impurity a specific relative retention time is less than about 0.6% by weight after 0 months, 12 months, or 18 months of storage. In some embodiments, the impurity a specific relative retention time is less than about 0.5% by weight by weight after 0 months, 12 months, or 18 months of storage. In some embodiments, the impurity a specific relative retention time is less than about 0.4% by weight after 0 months, 12 months, or 18 months of storage. In some embodiments, the impurity a specific relative retention time is less than about 0.3% by weight after 0 months, 12 months, or 18 months of storage. In some embodiments, the impurity a specific relative retention time is less than about 0.2% by weight after 0 months, 12 months, or 18 months of storage. In some embodiments, the impurity a specific relative retention time is less than about 0.1% by weight after 0 months, 12 months, or 18 months of storage. In some embodiments, the impurity a specific relative retention time is less than about 0.09% by weight after 0 months, 12 months, or 18 months of storage. In some embodiments, the impurity a specific relative retention time is less than about 0.08% by weight after 0 months, 12 months, or 18 months of storage. In some embodiments, the impurity a specific relative retention time is less than about 0.07% by weight after 0 months, 12 months, or 18 months of storage. In some embodiments, the impurity a specific relative retention time is less than about 0.06% by weight after 0 months, 12 months, or 18 months of storage. In some embodiments, the impurity a specific relative retention time is less than about 0.05% by weight after 0 months, 12 months, or 18 months of storage. In some embodiments, the impurity a specific relative retention time is less than about 0.04% by weight after 0 months, 12 months, or 18 months of storage. In some embodiments, the impurity a specific relative retention time is less than about 0.03% by weight after 0 months, 12 months, or 18 months of storage. In some embodiments, the impurity a specific relative retention time is less than about 0.02% by weight after 0 months, 12 months, or 18 months of storage. In some embodiments, the impurity a specific relative retention time is less than about 0.01% by weight after 0 months, 12 months, or 18 months of storage. In some embodiments, the impurity a specific relative retention time is less than about 0.005% by weight after 0 months, 12 months, or 18 months of storage. In some embodiments, the impurity a specific relative retention time is less than about 0.001% by weight after 0 months, 12 months, or 18 months of storage.

In some embodiments, the impurity a specific relative retention time is from less than about 1.5% to about 0.001%, less than about 1.4% to about 0.001%, less than about 1.3% to about 0.001%, less than about 1.2% to about 0.001%, less than about 1.1% to about 0.001%, less than about 1.0% to about 0.001%, less than about 0.9% to about 0.001%, less than about 0.8% to about 0.001%, less than about 0.7% to about 0.001%, less than about 0.6% to about 0.001%, less than about 0.5% to about 0.001%, less than about 0.4% to about 0.001%, less than about 0.3% to about 0.001%, less than about 0.2% to about 0.001%, less than about 0.1% to about 0.001%, less than about 0.09% to about 0.001%, less than about 0.08% to about 0.001%, less than about 0.07% to about 0.001%, less than about 0.06% to about 0.001%, less than about 0.05% to about 0.001%, less than about 0.04% to about 0.001%, less than about 0.03% to about 0.001%, less than about 0.02% to about 0.001%, less than about 0.01% to about 0.001%, or less than about 0.005% to about 0.001% by weight after 0 months, 12 months, or 18 months of storage.

In some embodiments, the impurity a specific relative retention time is from less than about 1.5% to about 0.01%, less than about 1.4% to about 0.01%, less than about 1.3% to about 0.01%, less than about 1.2% to about 0.01%, less than about 1.1% to about 0.01%, less than about 1.0% to about 0.01%, less than about 0.9% to about 0.01%, less than about 0.8% to about 0.01%, less than about 0.7% to about 0.01%, less than about 0.6% to about 0.01%, less than about 0.5% to about 0.01%, less than about 0.4% to about 0.01%, less than about 0.3% to about 0.01%, less than about 0.2% to about 0.01%, less than about 0.1% to about 0.01%, less than about 0.09% to about 0.01%, less than about 0.08% to about 0.01%, less than about 0.07% to about 0.01%, less than about 0.06% to about 0.01%, less than about 0.05% to about 0.01%, less than about 0.04% to about 0.01%, less than about 0.03% to about 0.01%, or less than about 0.02% to about 0.01% by weight after 0 months, 12 months, or 18 months of storage.

In some embodiments, the impurity a specific relative retention time is from less than about 1.5% to about 0.1%, less than about 1.4% to about 0.1%, less than about 1.3% to about 0.1%, less than about 1.2% to about 0.1%, less than about 1.1% to about 0.1%, less than about 1.0% to about 0.1%, less than about 0.9% to about 0.1%, less than about 0.8% to about 0.1%, less than about 0.7% to about 0.1%, less than about 0.6% to about 0.1%, less than about 0.5% to about 0.1%, less than about 0.4% to about 0.1%, less than about 0.3% to about 0.1%, or less than about 0.2% to about 0.1% by weight after 0 months, 12 months, or 18 months of storage.

Stability

It is recognized herein that the compositions described herein have improved shelf life. In some embodiments, the benoxinate component and/or the fluorescein component (including the pharmaceutically acceptable salt or salts thereof) of the compositions described herein minimally degrade after storage (i.e., after 12 months and/or 18 months of storage).

In some embodiments, the composition comprises at least about 85% of the benoxinate component that has not degraded after 12 months of storage. In some embodiments, the composition comprises at least about 90% of the benoxinate component that has not degraded after 12 months of storage. In some embodiments, the composition comprises at least about 92% of the benoxinate component that has not degraded after 12 months of storage. In some embodiments, the composition comprises at least about 95% of the benoxinate component that has not degraded after 12 months of storage. In some embodiments, the composition comprises at least about 100% of the benoxinate component that has not degraded after 12 months of storage. In some embodiments, the composition comprises at least about 85%, at least about 90%, at least about 91%, at least about 92%, at least about 93%, at least about 94%, at least about 95%, at least about 96%, at least about 97%, at least about 98%, at least about 99%, or at least about 100% of the benoxinate component that has not degraded after 12 months of storage. In some embodiments, the composition comprises about 85%, about 90%, about 91%, about 92%, about 93%, about 94%, about 95%, about 96%, about 97%, about 98%, about 99%, or about 100% of the benoxinate component that has not degraded after 12 months of storage.

In some embodiments, the composition comprises at least about 85% of the benoxinate component that has not degraded after 18 months of storage. In some embodiments, the composition comprises at least about 90% of the benoxinate component that has not degraded after 18 months of storage. In some embodiments, the composition comprises at least about 92% of the benoxinate component that has not degraded after 18 months of storage. In some embodiments, the composition comprises at least about 95% of the benoxinate component that has not degraded after 18 months of storage. In some embodiments, the composition comprises at least about 100% of the benoxinate component that has not degraded after 18 months of storage. In some embodiments, the composition comprises at least about 85%, at least about 90%, at least about 91%, at least about 92%, at least about 93%, at least about 94%, at least about 95%, at least about 96%, at least about 97%, at least about 98%, at least about 99%, or at least about 100% of the benoxinate component that has not degraded after 18 months of storage. In some embodiments, the composition comprises about 85%, about 90%, about 91%, about 92%, about 93%, about 94%, about 95%, about 96%, about 97%, about 98%, about 99%, or about 100% of the benoxinate component that has not degraded after 18 months of storage.

In some embodiments, the composition comprises at least about 85% of the fluorescein component that has not degraded after 12 months of storage. In some embodiments, the composition comprises at least about 90% of the fluorescein component that has not degraded after 12 months of storage. In some embodiments, the composition comprises at least about 95% of the fluorescein component that has not degraded after 12 months of storage. In some embodiments, the composition comprises at least about 97% of the fluorescein component that has not degraded after 12 months of storage. In some embodiments, the composition comprises at least about 98% of the fluorescein component that has not degraded after 12 months of storage. In some embodiments, the composition comprises at least about 99% of the fluorescein component that has not degraded after 12 months of storage. In some embodiments, the composition comprises at least about 100% of the fluorescein component that has not degraded after 12 months of storage. In some embodiments, the composition comprises about 85% of the fluorescein component that has not degraded after 12 months of storage. In some embodiments, the composition comprises about 90% of the fluorescein component that has not degraded after 12 months of storage. In some embodiments, the composition comprises about 95% of the fluorescein component that has not degraded after 12 months of storage. In some embodiments, the composition comprises about 97% of the fluorescein component that has not degraded after 12 months of storage. In some embodiments, the composition comprises about 98% of the fluorescein component that has not degraded after 12 months of storage. In some embodiments, the composition comprises about 99% of the fluorescein component that has not degraded after 12 months of storage. In some embodiments, the composition comprises about 100% of the fluorescein component that has not degraded after 12 months of storage.

In some embodiments, the composition comprises at least about 85% of the fluorescein component that has not degraded after 18 months of storage. In some embodiments, the composition comprises at least about 90% of the fluorescein component that has not degraded after 18 months of storage. In some embodiments, the composition comprises at least about 95% of the fluorescein component that has not degraded after 18 months of storage. In some embodiments, the composition comprises at least about 97% of the fluorescein component that has not degraded after 18 months of storage. In some embodiments, the composition comprises at least about 98% of the fluorescein component that has not degraded after 18 months of storage. In some embodiments, the composition comprises at least about 99% of the fluorescein component that has not degraded after 18 months of storage. In some embodiments, the composition comprises at least about 100% of the fluorescein component that has not degraded after 18 months of storage. In some embodiments, the composition comprises about 85% of the fluorescein component that has not degraded after 18 months of storage. In some embodiments, the composition comprises about 90% of the fluorescein component that has not degraded after 18 months of storage. In some embodiments, the composition comprises about 95% of the fluorescein component that has not degraded after 18 months of storage. In some embodiments, the composition comprises about 97% of the fluorescein component that has not degraded after 18 months of storage. In some embodiments, the composition comprises about 98% of the fluorescein component that has not degraded after 18 months of storage. In some embodiments, the composition comprises about 99% of the fluorescein component that has not degraded after 18 months of storage. In some embodiments, the composition comprises about 100% of the fluorescein component that has not degraded after 18 months of storage.

In some embodiments, the composition described herein is stored at from about 2° C. to about 8° C. In some embodiments, the composition described herein is stored at from about 2° C. to about 8° C. for 12 months. In some embodiments, the composition described herein is stored at from about 2° C. to about 8° C. for 18 months. In some embodiments, the composition described herein is stored at about 2° C., about 3° C., about 4° C., about 5° C., about 6° C., about 7° C., or about 8° C. In some embodiments, the composition described herein is stored at about 2° C., about 3° C., about 4° C., about 5° C., about 6° C., about 7° C., or about 8° C. for 12 months. In some embodiments, the composition described herein is stored at about 2° C., about 3° C., about 4° C., about 5° C., about 6° C., about 7° C., or about 8° C. for 18 months.

Methods/Uses

In some embodiments, the compositions described herein are suitable for ophthalmic use. In some embodiments, the composition is used in tonometry.

Also described herein in one aspect is a method for removing foreign bodies and sutures in a subject in need thereof comprising administering an effective amount, such as a therapeutically effective amount, of any one of the compositions described herein.

In another aspect, described herein is a method for conducting an ocular examination in a subject in need thereof comprising: administering an effective amount, such as a therapeutically effective amount, of any one of the compositions described herein. In some embodiments, the method further comprises measuring the intraocular pressure of the eye.

Certain Terminology

As used herein, the term "about" is used synonymously with the term "approximately." Illustratively, the use of the term "about" with regard to a specific amount indicates values slightly outside the cited values, e.g., plus or minus 0.1% to 10%. In some embodiments, "about" indicates values that are plus or minus 10%.

The term "acceptable" with respect to a formulation, composition or ingredient, as used herein, means having no persistent detrimental effect on the general health of the subject being treated.

The term "carrier," as used herein, refers to relatively nontoxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

As used herein, the following terms have the following meanings: NA=not available; ND=not detected; RRT=relative retention time; Q.S=quantity sufficient; and NMT=not more than.

All of the various embodiments or options described herein can be combined in any and all variations. The following Examples serve only to illustrate the invention and are not to be construed in any way to limit the invention.

EXAMPLES

Example 1: Exemplary Fluorescein and Benoxinate Ophthalmic Solution

Fluorescein and benoxinate ophthalmic solution is supplied in a glass bottle with a sterilized dropper applicator in a 5 mL size.

Active agents include the following: benoxinate hydrochloride 4 mg (0.4%) and fluorescein sodium 2.5 mg (0.25%).

A preservative, such as Chlorobutanol 10 mg (1%), is included.

Inactive agents include the following: povidone, boric acid, purified water USP, and optionally hydrochloric acid (to adjust pH).

The composition of fluorescein and benoxinate is listed below in the following table.

TABLE 1

Exemplary Fluorescein and Benoxinate Solution

| Component | Formulation Quantity (%w/v) | Function | Quality Standard |
|---|---|---|---|
| Benoxinate hydrochloride | 0.4% | Active Ingredient | USP |
| Fluorescein sodium | 0.25% | Active Ingredient | — |
| Povidone | 10% to 20% | Viscosity agent | — |
| Boric Acid | — | Buffering Agent | — |
| Purified Water | Q.S | Diluent | — |
| Hydrochloric Acid | As needed | pH adjustment | — |
| Chlorobutanol | — | Preservative | — |

Example 2: Stability Tests of Fluorescein and Benoxinate Compositions

HPLC Method A as described herein was used to analyze the compositions containing fluorescein and benoxinate prior to and after storage (12 months and 18 months at 2° C. to 8° C.).

The following table shows the compositions comprising fluorescein and benoxinate that were analyzed. Formulations 1-8 are commercially available fluorescein and benoxinate ophthalmic solutions. Formulations 9-11 are exemplary compositions comprising fluorescein and benoxinate as described in Example 1.

TABLE 2

Fluorescein and Benoxinate Formulations
Formulation No.

Formulation 1
Formulation 2
Formulation 3
Formulation 4
Formulation 5
Formulation 6
Formulation 7
Formulation 8
Formulation 9
Formulation 10
Formulation 11

The formulations as noted in Table 2 were analyzed by HPLC Method A to assess the individual impurities and total impurities present in each formulation at the following time points: after 0 months of storage, after 12 months of storage, and after 18 months of storage.

FIG. 1A shows an overlay HPLC chromatogram of Formulation 7, Run 1 after 12 months of storage. FIG. 1B shows an overlay HPLC chromatogram of Formulation 7, Run 2 after 12 months of storage. FIG. 1C shows an overlay HPLC chromatogram of Formulation 7, Run 1 after 18 months of storage. FIG. 1D shows an overlay HPLC chromatogram of Formulation 7, Run 2, after 18 months of storage.

Figure 2F:
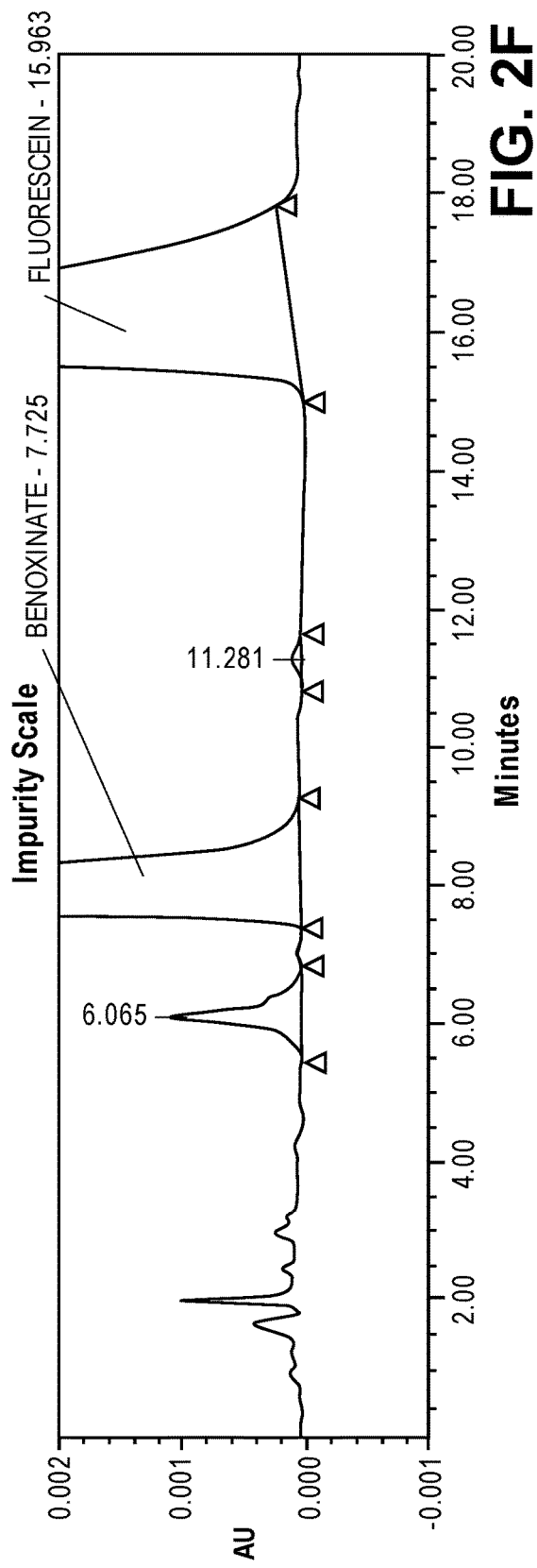
FIG. 2F shows an overlay HPLC chromatogram of Formulation 8, Run 2, after 18 months of storage.

FIG. 2A shows an overlay HPLC chromatogram of Formulation 8, Run 1 after 0 months of storage. FIG. 2B shows an overlay HPLC chromatogram of Formulation 8, Run 2 after 0 months of storage. FIG. 2C shows an overlay HPLC chromatogram of Formulation 8, Run 1 after 12 months of storage. FIG. 2D shows an overlay HPLC chromatogram of Formulation 8, Run 2, after 12 months of storage. FIG. 2E shows an overlay HPLC chromatogram of Formulation 8, Run 1 after 18 months of storage. FIG. 2F shows an overlay HPLC chromatogram of Formulation 8, Run 2, after 18 months of storage.

The HPLC chromatograms of Formulations 1-6 show similar impurity peaks as shown in the HPLC chromatograms of FIG. 1A-1D and FIG. 2A-2F.

Figure 3C:
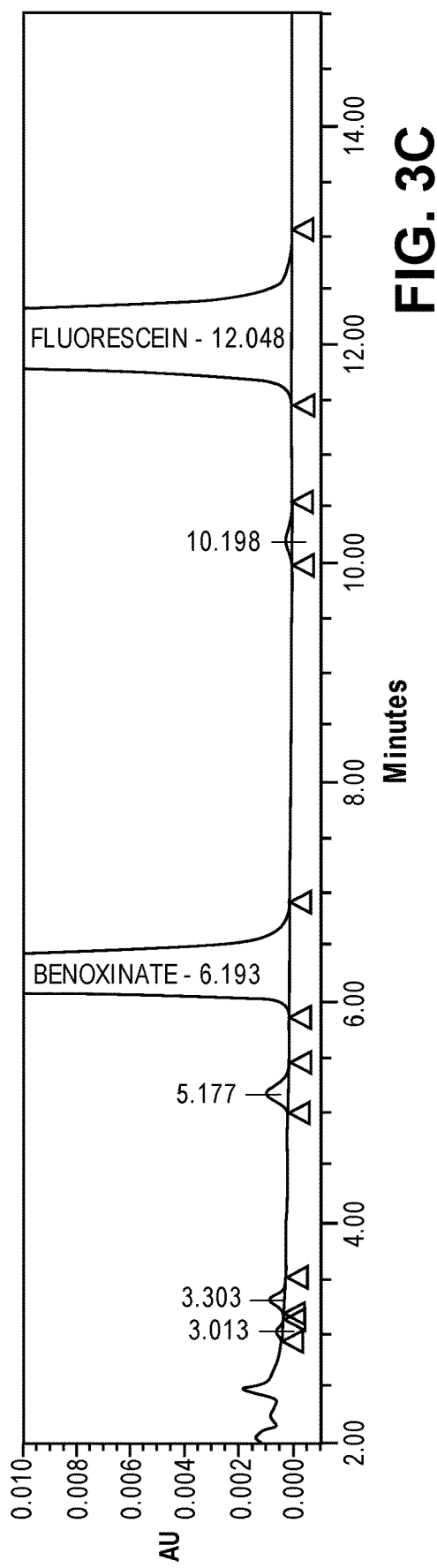
FIG. 3C shows an overlay HPLC chromatogram of Formulation 9, Run 1 after 12 months of storage.
Figure 3D:
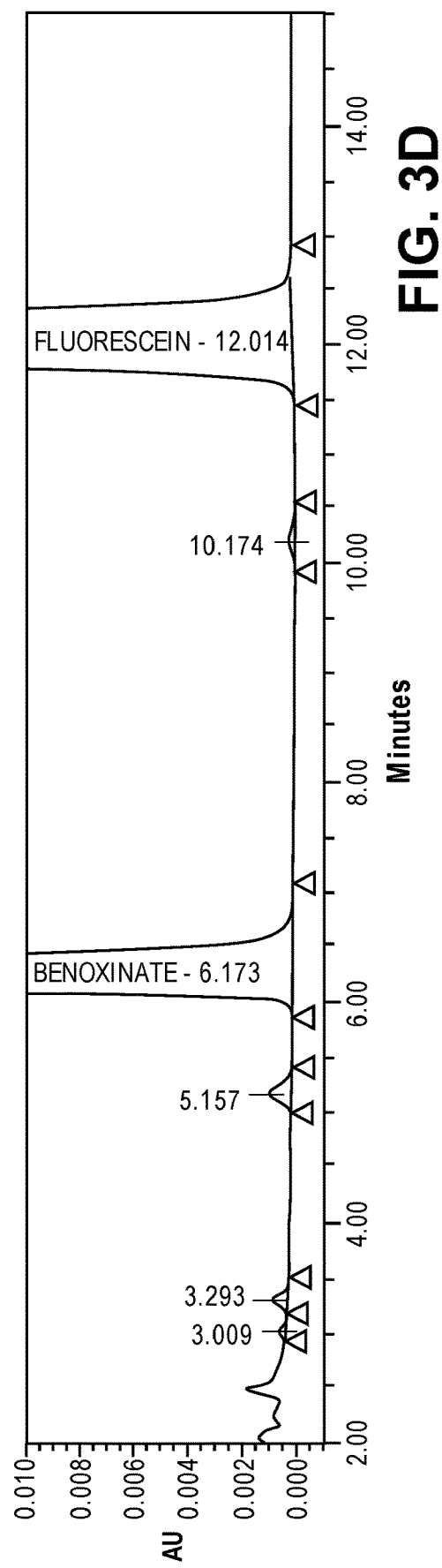
FIG. 3D shows an overlay HPLC chromatogram of Formulation 9, Run 2, after 12 months of storage.

FIG. 3A shows an overlay HPLC chromatogram of Formulation 9, Run 1 after 0 months of storage. FIG. 3B shows an overlay HPLC chromatogram of Formulation 9, Run 2 after 0 months of storage. FIG. 3C shows an overlay HPLC chromatogram of Formulation 9, Run 1 after 12 months of storage. FIG. 3D shows an overlay HPLC chromatogram of Formulation 9, Run 2, after 12 months of storage. FIG. 3E shows an overlay HPLC chromatogram of Formulation 9, Run 1 after 18 months of storage. FIG. 3F shows an overlay HPLC chromatogram of Formulation 9, Run 2, after 18 months of storage.

Figure 4A:
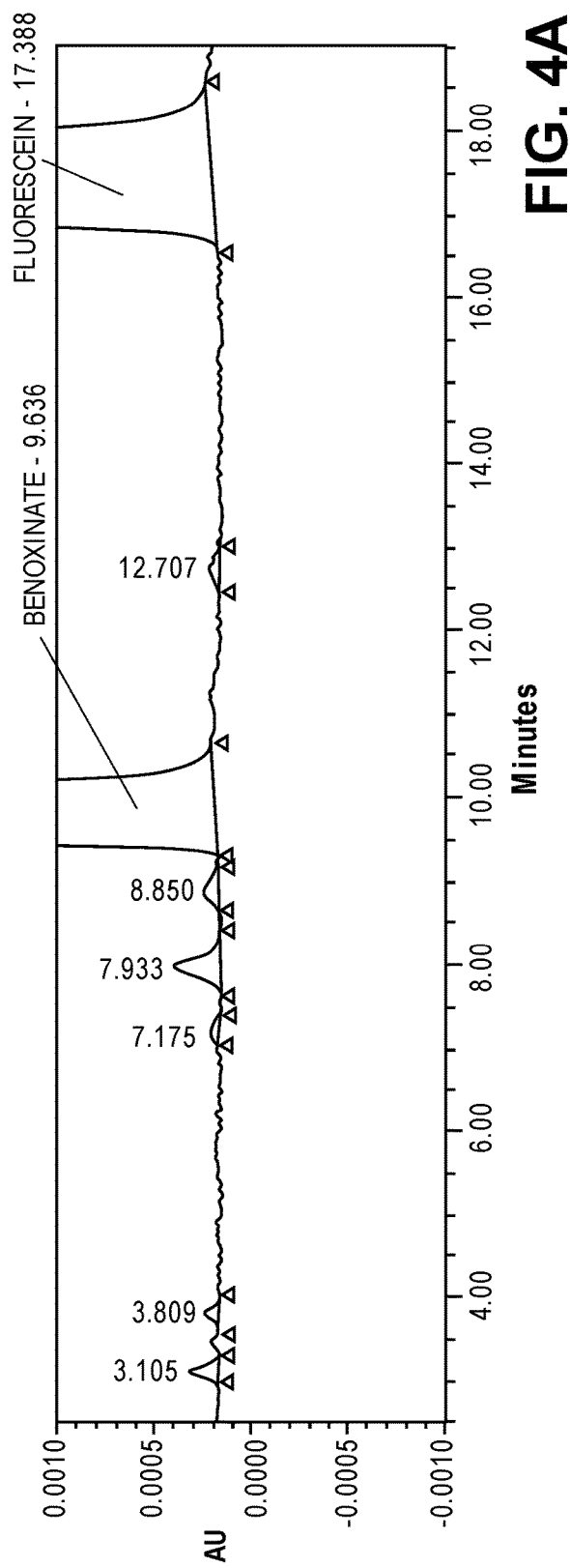
FIG. 4A shows an overlay HPLC chromatogram of Formulation 10, Run 1 after 0 months of storage.
Figure 4B:
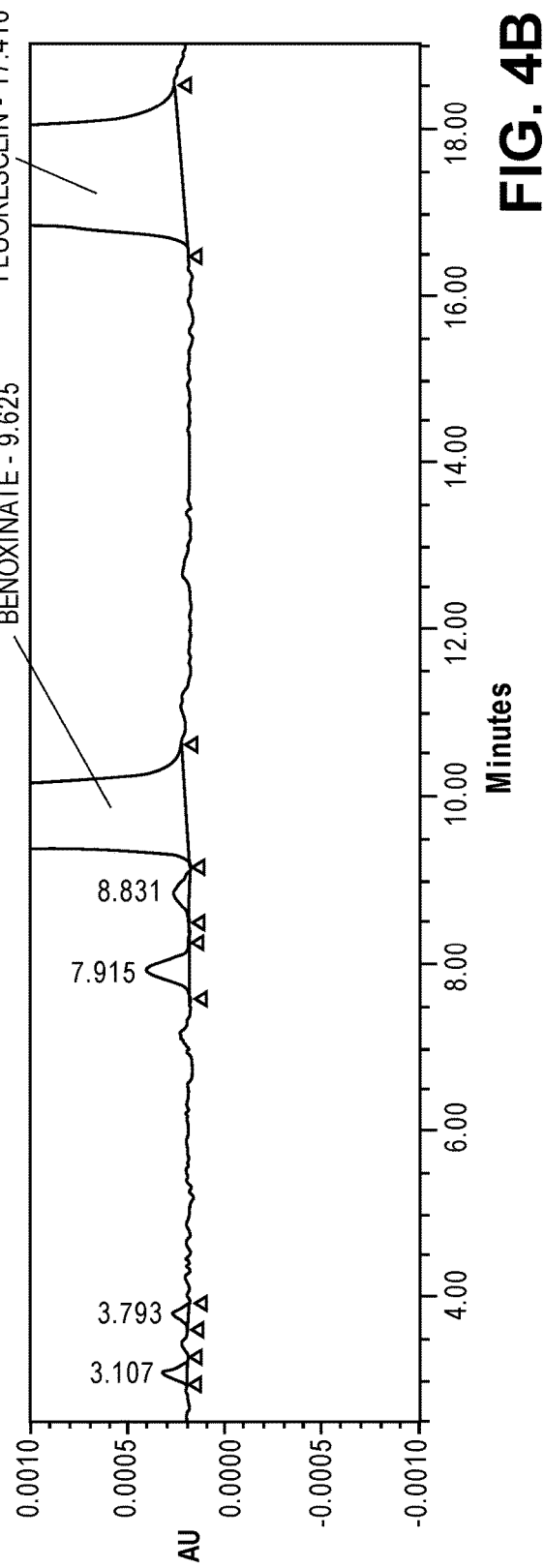
FIG. 4B shows an overlay HPLC chromatogram of Formulation 10, Run 2 after 0 months of storage.
Figure 4C:
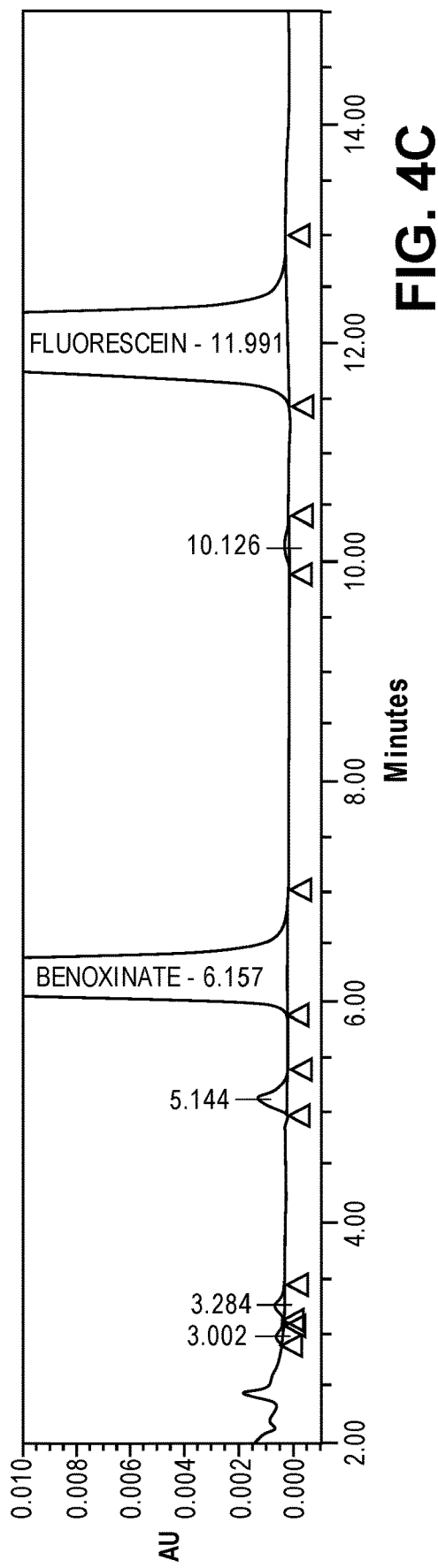
FIG. 4C shows an overlay HPLC chromatogram of Formulation 10, Run 1 after 12 months of storage.
Figure 4D:
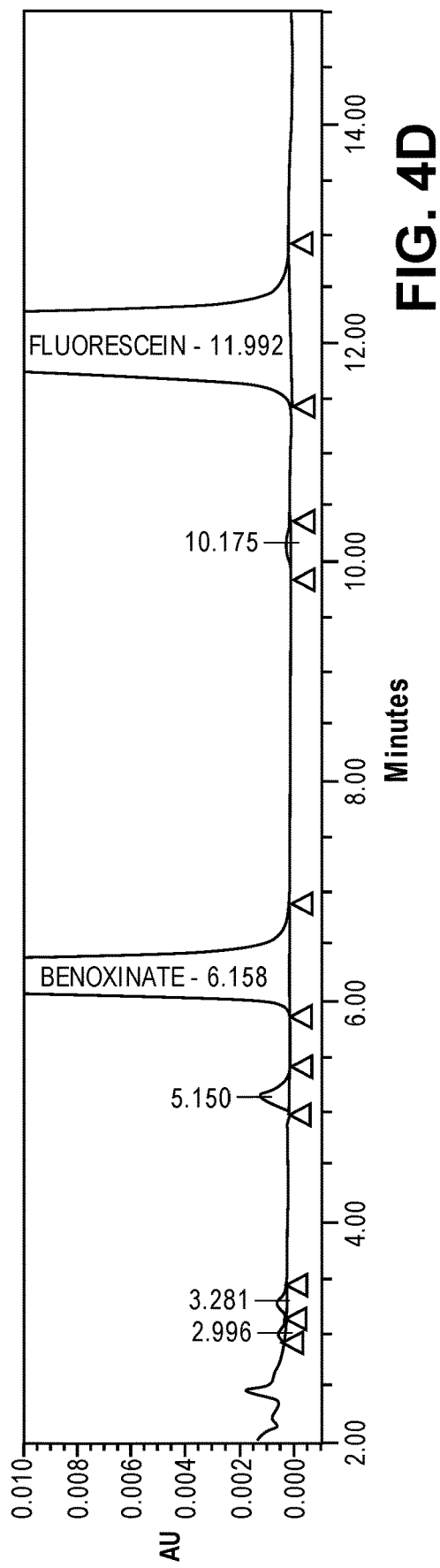
FIG. 4D shows an overlay HPLC chromatogram of Formulation 10, Run 2, after 12 months of storage.

FIG. 4A shows an overlay HPLC chromatogram of Formulation 10, Run 1 after 0 months of storage. FIG. 4B shows an overlay HPLC chromatogram of Formulation 10, Run 2 after 0 months of storage. FIG. 4C shows an overlay HPLC chromatogram of Formulation 10, Run 1 after 12 months of storage. FIG. 4D shows an overlay HPLC chromatogram of Formulation 10, Run 2, after 12 months of storage. FIG. 4E shows an overlay HPLC chromatogram of Formulation 10, Run 1 after 18 months of storage. FIG. 4F shows an overlay HPLC chromatogram of Formulation 10, Run 2, after 18 months of storage.

Figure 5A:
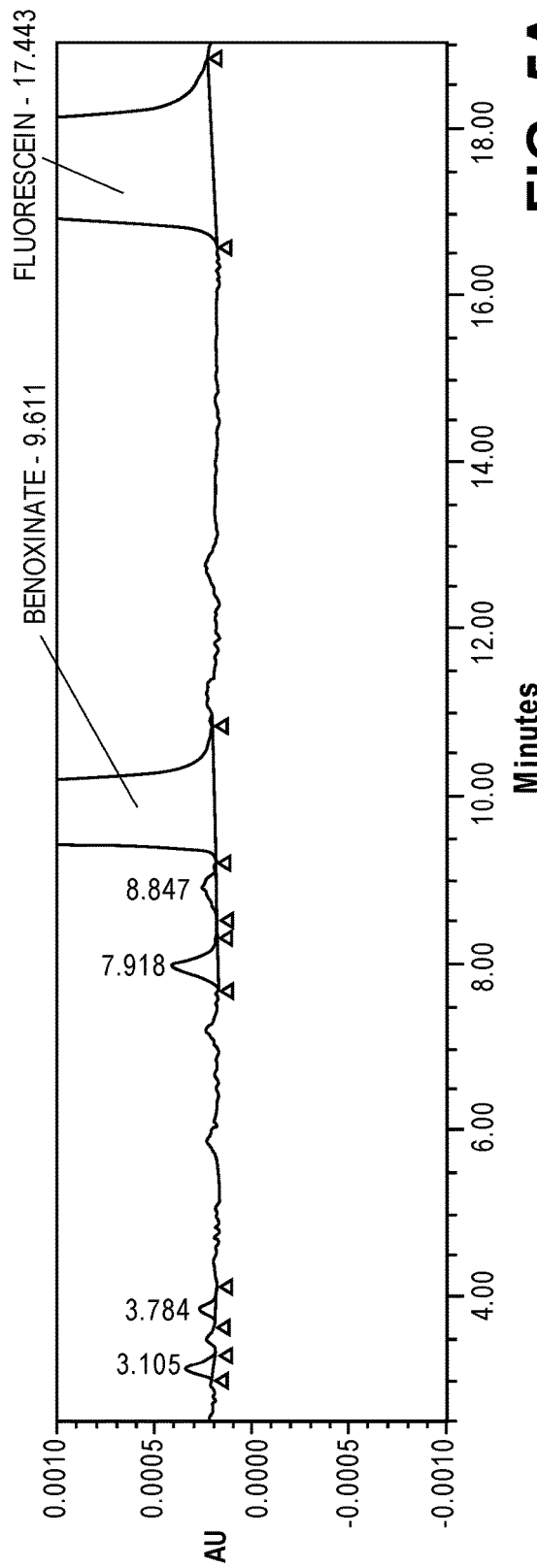
FIG. 5A shows an overlay HPLC chromatogram of Formulation 11, Run 1 after 0 months of storage.
Figure 5B:
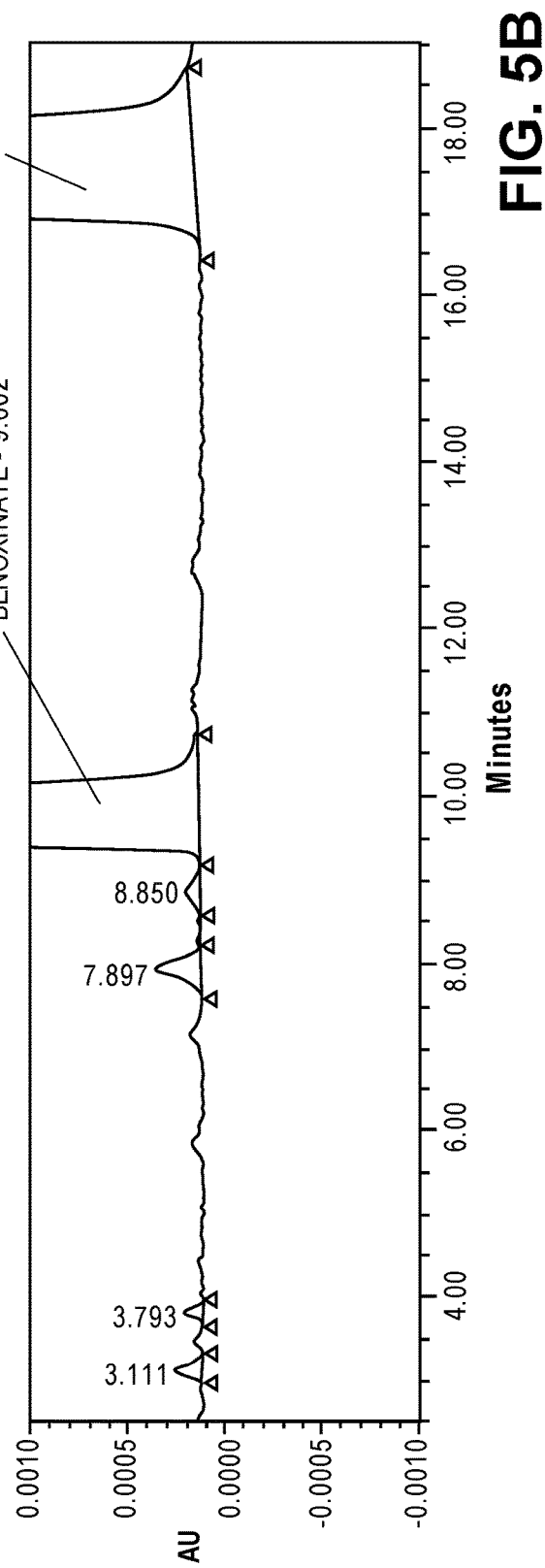
FIG. 5B shows an overlay HPLC chromatogram of Formulation 11, Run 2 after 0 months of storage.

FIG. 5A shows an overlay HPLC chromatogram of Formulation 11, Run 1 after 0 months of storage. FIG. 5B shows an overlay HPLC chromatogram of Formulation 11, Run 2 after 0 months of storage. FIG. 5C shows an overlay HPLC chromatogram of Formulation 11, Run 1 after 12 months of storage. FIG. 5D shows an overlay HPLC chromatogram of Formulation 11, Run 2, after 12 months of storage. FIG. 5E shows an overlay HPLC chromatogram of Formulation 11, Run 1 after 18 months of storage. FIG. 5F shows an overlay HPLC chromatogram of Formulation 11, Run 2, after 18 months of storage.

Table 3 shows the total impurity as determined by HPLC Method A for Formulations 1-8 at the following time points: after 0 months of storage, after 12 months of storage, and after 18 months of storage.

TABLE 3

Total Impurities for Formulations 1-8

| Formulation No. | % Total Impurity after 0 months | % Total Impurity after 12 months | % Total Impurity after 18 months |
|---|---|---|---|
| Formulation 1 | 1.20 | 1.70 | 1.10 |
| Formulation 2 | 1.11 | 0.74 | 1.42 |
| Formulation 3 | 1.60 | 0.94 | 1.04 |
| Formulation 4 | 1.70 | 1.05 | 1.17 |
| Formulation 5 | 1.80 | 1.13 | 1.02 |
| Formulation 6 | 1.70 | 1.12 | 0.80 |
| Formulation 7 | 1.50 | 1.40 | 1.58 |
| Formulation 8 | 1.56 | 1.18 | 0.90 |
| Average | 1.52 | 1.16 | 1.13 |
| Min | 1.11 | 0.74 | 0.80 |
| Max | 1.80 | 1.70 | 1.58 |
| STD Dev | 0.25 | 0.29 | 0.26 |

Table 4 shows the total impurity as determined by HPLC Method A for Formulations 9-11 at the following time points: after 0 months of storage, after 12 months of storage, and after 18 months of storage.

TABLE 4

Total Impurities for Formulations 9-11

| Formulation No. | % Total Impurity after 0 months | % Total Impurity after 12 months | % Total Impurity after 18 months |
|---|---|---|---|
| Formulation 9 | 0.27 | 0.63 | 0.62 |
| Formulation 10 | 0.26 | 0.66 | 0.47 |
| Formulation 11 | 0.23 | 0.74 | 0.58 |
| Average | 0.25 | 0.68 | 0.56 |
| Min | 0.23 | 0.63 | 0.47 |
| Max | 0.27 | 0.74 | 0.62 |

Figure 6:
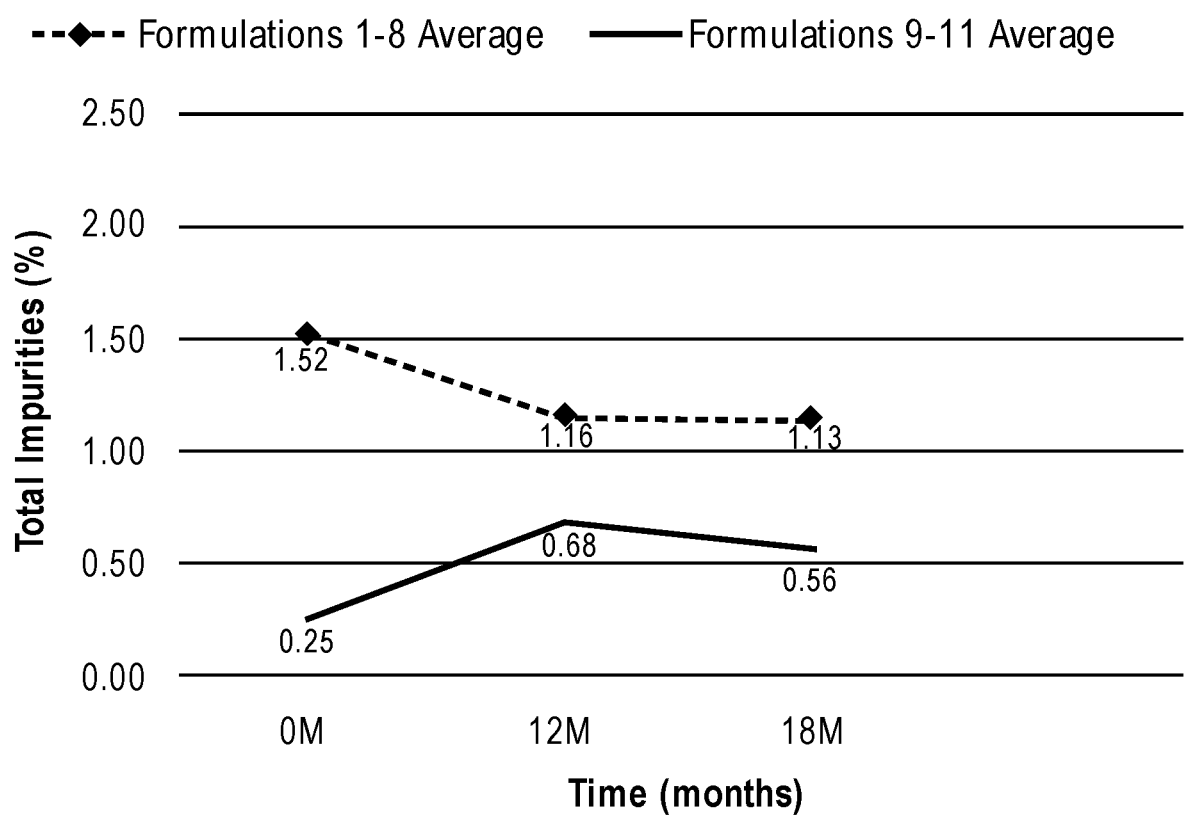
FIG. 6 shows the average of the total impurities for formulations 1-8 and formulations 9-11 as determined by HPLC Method A at the following time points: after 0 months of storage, after 12 months of storage, and after 18 months of storage.

FIG. 6 shows the average of the total impurities for formulations 1-8 and formulations 9-11 as determined by HPLC Method A at the following time points: after 0 months of storage, after 12 months of storage, and after 18 months of storage.

Table 5 shows average of each impurity, including total impurity, as determined by HPLC Method A for Formulations 1-8 and Formulations 9-11 after 0 months of storage.

TABLE 5

Specific Impurities After 0 Months of Storage

| Impurity Description | % Impurity for Formulations 1-8 | % Impurity for Formulations 9-11 | Notes |
|---|---|---|---|
| Specified unidentified impurity #1 (RRT 0.33) NMT 0.50% | ND | 0.05 | — |
| Specified unidentified impurity #2 (RRT 0.36) NMT 0.50% | 0.05 | ND | — |
| Unspecified unidentified impurity NMT 0.10% | ND | 0.05 | — |
| Specified unidentified impurity #3 (RRT 0.43) NMT 0.50% | 0.13 | ND | — |
| Specified unidentified impurity #4 (RRT 0.5) NMT 0.50% | 0.06 | ND | — |
| Specified unidentified impurity #5 (RRT 0.54) NMT 0.50% | ND | ND | — |
| Specified unidentified impurity #6 (RRT 0.59) NMT 0.50% | ND | ND | — |
| Specified unidentified impurity #7 (RRT 0.63) NMT 0.50% | ND | ND | — |
| Specified unidentified impurity #8 (RRT 0.68) NMT 1.50% | 1.4 | ND | — |
| Specified unidentified impurity #9 (RRT 0.74) NMT 2.00% | 1.55 | ND | — |
| Specified unidentified impurity #10 (RRT0.79) NMT 1.50% | 0.42 | ND | — |
| Specified unidentified impurity #11 (RRT 0.85) NMT 1.50% | 0.08 | 0.14 | — |
| Specified Identified Impurity: 2-(2,4 Dihydroxy Benzoyl) Benzoic Acid (RRT 0.91) NMT 1.50% | ND | 0.05 | — |
| Specified Unidentified Impurity# 12 (RRT 1.15) NMT 0.50% | ND | ND | — |
| Specified Unidentified Impurity #13 (RRT 1.34) NMT 0.50% | ND | ND | — |
| Specified Identified Impurity: 4 amino 3 Butoxy Benzoic Acid (RRT 1.62) NMT 1.00% | ND | ND | — |
| Specified Unidentified Impurity #14 (RRT 1.71) NMT 1.00% | ND | ND | — |
| Total Impurities | 3.69 | 0.29 | — |

Table 6 shows each impurity, including total impurity, as determined by HPLC Method A for Formulations 1-8 and Formulations 9-11 after 12 months of storage.

TABLE 6

Specific Impurities After 12 Months of Storage

| Impurity Description | % Impurity for Formulations 1-8 | % Impurity for Formulations 9-11 | Notes |
|---|---|---|---|
| Specified unidentified impurity #1 (RRT 0.33) NMT 0.50% | ND | ND | — |
| Specified unidentified impurity #2 (RRT 0.36) NMT 0.50% | ND | ND | — |
| Unspecified unidentified impurity NMT 0.10% | ND | ND | — |
| Specified unidentified impurity #3 (RRT 0.43) NMT 0.50% | 0.11 | ND | Only detected in Formulation 6 |
| Specified unidentified impurity #4 (RRT 0.5) NMT 0.50% | ND | 0.047 | — |
| Specified unidentified impurity #5 (RRT 0.54) NMT 0.50% | ND | 0.12 | — |
| Specified unidentified impurity #6 (RRT 0.59) NMT 0.50% | ND | ND | — |
| Specified unidentified impurity #7 (RRT 0.63) NMT 0.50% | ND | ND | — |
| Specified unidentified impurity #8 (RRT 0.68) NMT 1.50% | 0.91 | ND | — |
| Specified unidentified impurity #9 (RRT 0.74) NMT 2.00% | 0.44 | ND | Only detected for in Formulation 2 |
| Specified unidentified impurity #10 (RRT 0.79) NMT 1.50% | 0.57 | ND | Only detected in Formulation 1 and Formulation 3 |
| Specified unidentified impurity #11 (RRT 0.85) NMT 1.50% | 0.33 | 0.41 | — |
| Specified Identified Impurity: 2-(2,4 Dihydroxy Benzoyl) Benzoic Acid (RRT 0.91) NMT 1.50% | ND | ND | — |
| Specified Unidentified Impurity# 12 (RRT 1.15) NMT 0.50% | ND | ND | — |
| Specified Unidentified Impurity #13 (RRT 1.34) NMT 0.50% | ND | ND | — |
| Specified Identified Impurity: 4 amino 3 Butoxy Benzoic Acid (RRT 1.62) NMT 1.00% | ND | 0.11 | — |
| Specified Unidentified Impurity #14 (RRT 1.71) NMT 1.00% | ND | ND | — |
| Total Impurities | 2.36 | 0.687 | — |

Table 7 shows each impurity, including total impurity, as determined by HPLC Method A for Formulations 1-8 and Formulations 9-11 after 18 months of storage.

TABLE 7

Specific Impurities After 18 Months of Storage

| Impurity Description | % Impurity for Formulations 1-8 | % Impurity for Formulations 9-11 | Notes |
|---|---|---|---|
| Specified unidentified impurity #1 (RRT 0.33) NMT 0.50% | 0.19 | ND | Only detected in Formulation 1 |
| Specified unidentified impurity #2 (RRT 0.36) NMT 0.50% | 0.13 | ND | — |
| Unspecified unidentified impurity NMT 0.10% | ND | 0.09 (RRT 1.55) | — |
| Specified unidentified impurity #3 (RRT 0.43) NMT 0.50% | 0.17 | ND | Only detected in Formulation 6 |
| Specified unidentified impurity #4 (RRT 0.5) NMT 0.50% | ND | 0.047 | — |
| Specified unidentified impurity #5 (RRT 0.54) NMT 0.50% | ND | 0.12 | — |
| Specified unidentified impurity #6 (RRT 0.59) NMT 0.50% | ND | ND | — |
| Specified unidentified impurity #7 (RRT 0.63) NMT 0.50% | ND | ND | — |
| Specified unidentified impurity #8 (RRT 0.68) NMT 1.50% | 0.76 | ND | — |
| Specified unidentified impurity #9 (RRT 0.74) NMT 2.00% | 0.5 | ND | Only detected in Formulation 2 |
| Specified unidentified impurity #10 (RRT 0.79) NMT 1.50% | 0.79 | ND | Only detected in Formulation 1 and Formulation 3 |
| Specified unidentified impurity #11 (RRT 0.85) NMT 1.50% | 0.39 | 0.41 | — |
| Specified Identified Impurity: 2-(2,4 Dihydroxy Benzoyl) Benzoic Acid (RRT 0.91) NMT 1.50% | ND | ND | — |
| Specified Unidentified Impurity# 12 (RRT 1.15) NMT 0.50% | ND | ND | — |
| Specified Unidentified Impurity #13 (RRT 1.34) NMT 0.50% | ND | ND | — |
| Specified Identified Impurity: 4 amino 3 Butoxy Benzoic Acid (RRT 1.62) NMT 1.00% | ND | 0.11 | — |
| Specified Unidentified Impurity #14 (RRT 1.71) NMT 1.00% | ND | ND | — |
| Total Impurities | 2.93 | 0.687 | — |

Table 8 shows the loss of benoxinate and fluorescein for Formulations 1-8 and Formulations 9-11 after 0 months of storage, 12 months of storage, and 18 months of storage.

TABLE 8

Loss of Benoxinate and Fluorescein After 0 Months, 12 Month, and 18 Months of Storage

| | Initial % Loss of | % Loss at 12 M compared to initial | % Loss at 18 M compared to initial |
|---|---|---|---|

TABLE 8-continued

Loss of Benoxinate and Fluorescein After 0
Months, 12 Month, and 18 Months of Storage

| Formulation No | Benoxinate | assay % | assay % |
|---|---|---|---|
| Formulations 1-8 (2-8° C.) | 0% | 8.52% | 10.43% |
| Formulations 9-11 (2-8° C.) | 0% | 3.03% | 5.0% |

| | Initial % Loss of Fluorescein | % Loss at 12 M compared to initial assay % | % Loss at 18 M compared to initial assay % |
|---|---|---|---|
| Formulations 1-8 (2-8° C.) | 0% | 2.0% | 2.6% |
| Formulations 9-11 (2-8° C.) | 0% | 0.36% | 0.09% |

EMBODIMENTS

Embodiment 1

A composition comprising: a) a fluorescein component; and b) benoxinate component; wherein the composition comprises a total impurity of about 1.5% or less by weight, and wherein the total impurity comprises one or more impurities with relative retention times from about 0.10 to about 1.90 under HPLC Method A.

Embodiment 2

The composition of embodiment 1, wherein the total impurity is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight.

Embodiment 3

The composition of embodiment 1, wherein the total impurity is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight.

Embodiment 4

The composition of any one of embodiments 1-3, wherein the total impurity is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 0 months of storage.

Embodiment 5

The composition of any one of embodiments 1-3, wherein the total impurity is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 0 months of storage.

Embodiment 6

The composition of any one of embodiments 1-5, wherein the total impurity is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 12 months storage.

Embodiment 7

The composition of any one of embodiments 1-5, wherein the total impurity is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 12 months of storage.

Embodiment 8

The composition of any one of embodiments 1-7, wherein the total impurity is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 18 months storage.

Embodiment 9

The composition of claim any one of embodiments 1-7, wherein the total impurity is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 18 months of storage.

Embodiment 10

The composition of any one of embodiments 1-9, wherein the total impurity comprises an impurity with a relative retention time of about 0.43.

Embodiment 11

The composition of embodiment 10, wherein the impurity with a relative retention time of about 0.43 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight.

Embodiment 12

The composition of embodiment 10, wherein the impurity with a relative retention time of about 0.43 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight.

Embodiment 13

The composition of any one of embodiments 10-12, wherein the impurity with a relative retention time of about 0.43 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 0 months of storage.

Embodiment 14

The composition of any one of embodiments 10-12, wherein the impurity with a relative retention time of about 0.43 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 0 months of storage.

Embodiment 15

The composition of any one of embodiments 10-14, wherein the impurity with a relative retention time of about 0.43 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 12 months storage.

Embodiment 16

The composition of any one of embodiments 10-14, wherein the impurity with a relative retention time of about 0.43 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 12 months of storage.

Embodiment 17

The composition of any one of embodiments 10-16, wherein the impurity with a relative retention time of about 0.43 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 18 months storage.

Embodiment 18

The composition of any one of embodiments 10-16, wherein the impurity with a relative retention time of about 0.43 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 18 months of storage.

Embodiment 19

The composition of any one of embodiments 1-18, wherein the total impurity comprises an impurity with a relative retention time of about 0.68.

Embodiment 20

The composition of embodiment 19, wherein the impurity with a relative retention time of about 0.68 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight.

Embodiment 21

The composition of embodiment 19, wherein the impurity with a relative retention time of about 0.68 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight.

Embodiment 22

The composition of any one of embodiment 19-21, wherein the impurity with a relative retention time of about 0.68 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 0 months of storage.

Embodiment 23

The composition of any one of embodiment 19-21, wherein the impurity with a relative retention time of about 0.68 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 0 months of storage.

Embodiment 24

The composition of any one of embodiment 19-23, wherein the impurity with a relative retention time of about 0.68 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 12 months storage.

Embodiment 25

The composition of any one of embodiment 19-23, wherein the impurity with a relative retention time of about 0.68 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 12 months of storage.

Embodiment 26

The composition of any one of embodiments 19-25, wherein the impurity with a relative retention time of about 0.68 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 18 months storage.

Embodiment 27

The composition of any one of embodiments 19-25, wherein the impurity with a relative retention time of about 0.68 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 18 months of storage.

Embodiment 28

The composition of any one of embodiments 1-27, wherein the total impurity comprises an impurity with a relative retention time of about 0.74.

Embodiment 29

The composition of claim 28, wherein the impurity with a relative retention time of about 0.74 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight.

Embodiment 30

The composition of embodiment 28, wherein the impurity with a relative retention time of about 0.74 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight.

Embodiment 31

The composition of any one of embodiments 28-30, wherein the impurity with a relative retention time of about 0.74 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 0 months of storage.

Embodiment 32

The composition of any one of embodiments 28-30, wherein the impurity with a relative retention time of about 0.74 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 0 months of storage.

Embodiment 33

The composition of any one of embodiments 28-32, wherein the impurity with a relative retention time of about 0.74 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 12 months storage.

Embodiment 34

The composition of any one of embodiments 28-32, wherein the impurity with a relative retention time of about 0.74 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 12 months of storage.

Embodiment 35

The composition of any one of embodiments 28-34, wherein the impurity with a relative retention time of about 0.74 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 18 months storage.

Embodiment 36

The composition of any one of embodiments 28-34, wherein the impurity with a relative retention time of about 0.74 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 18 months of storage.

Embodiment 37

The composition of any one of embodiments 1-36, wherein the total impurity comprises an impurity with a relative retention time of about 0.79.

Embodiment 38

The composition of embodiment 37, wherein the impurity with a relative retention time of about 0.79 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight.

Embodiment 39

The composition of embodiment 37, wherein the impurity with a relative retention time of about 0.79 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight.

Embodiment 40

The composition of any one of embodiments 37-39, wherein the impurity with a relative retention time of about 0.79 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 0 months of storage.

Embodiment 41

The composition of any one of embodiments 37-39, wherein the impurity with a relative retention time of about 0.79 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 0 months of storage.

Embodiment 42

The composition of any one of embodiments 37-41, wherein the impurity with a relative retention time of about 0.79 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 12 months storage.

Embodiment 43

The composition of any one of embodiments 37-41, wherein the impurity with a relative retention time of about 0.79 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 12 months of storage.

Embodiment 44

The composition of any one of embodiments 37-43, wherein the impurity with a relative retention time of about 0.79 is about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.005%, or about 0.001% by weight after 18 months storage.

Embodiment 45

The composition of any one of embodiments 37-43, wherein the impurity with a relative retention time of about 0.79 is less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, less than about 0.01%, less than about 0.005%, or less than about 0.001% by weight after 18 months of storage.

Embodiment 46

The composition of any one of embodiments 1-45, wherein the composition comprises at least about 90% of the benoxinate component that has not degraded after 12 months of storage.

Embodiment 47

The composition of any one of embodiments 1-46, wherein the composition comprises at least about 90% of the benoxinate component that has not degraded after 18 months of storage.

Embodiment 48

The composition of any one of embodiments 1-47, wherein the composition comprises at least about 97% of the fluorescein component that has not degraded after 12 months of storage.

Embodiment 49

The composition of any one of embodiments 1-48, wherein the composition comprises at least about 97% of the fluorescein component that has not degraded after 18 months of storage.

Embodiment 50

The composition of any one of embodiments 4-9, 13-18, 22-27, 31-36, and 40-49, wherein the composition is stored at from about 2° C. to about 8° C.

Embodiment 51

The composition of any one of embodiments 1-50, wherein the composition comprises about 0.25% by weight of the fluorescein component.

Embodiment 52

The composition of any one of embodiments 1-51, wherein the fluorescein component comprises fluorescein or the pharmaceutically acceptable salt thereof.

Embodiment 53

The composition of embodiment 52, wherein the pharmaceutically acceptable salt of fluorescein is the sodium salt.

Embodiment 54

The composition of any one of embodiments 1-53, wherein the composition comprises about 0.40% by weight of the benoxinate component.

Embodiment 55

The composition of any one of embodiments 1-54, wherein the benoxinate component comprises benoxinate or the pharmaceutically acceptable salt thereof.

Embodiment 56

The composition of embodiment 55, wherein the pharmaceutically acceptable salt of benoxinate is the hydrochloride salt.

Embodiment 57

The composition of any one of embodiments 1-56, wherein the composition has a pH of about 4.3 to about 5.3.

Embodiment 58

The composition of any one of embodiments 1-57, wherein the composition further comprises one or more inactive agents.

Embodiment 59

The composition of embodiments 58, wherein the inactive agents are boric acid, povidone, purified water, or hydrochloric acid.

Embodiment 60

The composition of any one of embodiments 1-59, wherein the composition further comprises a preservative.

Embodiment 61

The composition of embodiments 60, wherein the preservative is chlorobutanol or any other suitable ophthalmic preservative.

Embodiment 62

The composition of any one of embodiments 1-61, wherein composition is suitable for ophthalmic use.

Embodiment 63

The composition of embodiment 62, wherein the composition is used in tonometry.

Embodiment 64

A method for removing foreign bodies and sutures in a subject in need thereof comprising administering a therapeutically effective amount of any one of the compositions of embodiments 1-61.

Embodiment 65

A method for conducting an ocular examination in a subject in need thereof comprising: administering a therapeutically effective amount of any one of the compositions of embodiments 1-61.

Embodiment 66

The method of embodiment 65, further comprising measuring the intraocular pressure of the eye.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for administering a disclosing agent and an anesthetic to an eye of a subject in need of an ophthalmic procedure, comprising topically administering to the eye of the subject a composition comprising:
    (a) a fluorescein component; and
    (b) a benoxinate component;
    wherein the composition comprises a total impurity of about 1.5% or less by weight, and wherein the total impurity comprises one or more impurities with relative retention times from about 0.10 to about 1.90 under HPLC Method A.

2. The method of claim 1, wherein the total impurity is about 1.5% or less by weight after 12 months of storage.

3. The method of claim 1, wherein the total impurity is less than about 1.0% by weight after 12 months of storage.

4. The method of claim 1, wherein the total impurity comprises an impurity with a relative retention time of about 0.43.

5. The method of claim 4, wherein the impurity with a relative retention time of about 0.43 is less than about 1.0% by weight after 12 months of storage.

6. The method of claim 1, wherein the total impurity comprises an impurity with a relative retention time of about 0.68.

7. The method of claim 6, wherein the impurity with a relative retention time of about 0.68 is less than about 1.0% by weight after 12 months of storage.

8. The method of claim 1, wherein the total impurity comprises an impurity with a relative retention time of about 0.74.

9. The method of claim 8, wherein the impurity with a relative retention time of about 0.74 is less than about 1.0% by weight after 12 months of storage.

10. The method of claim 1, wherein the total impurity comprises an impurity with a relative retention time of about 0.79.

11. The method of claim 10, wherein the impurity with a relative retention time of about 0.79 is less than about 1.0% by weight after 12 months of storage.

12. The method of claim 1, wherein the composition comprises about 0.25% by weight of the fluorescein component.

13. The method of claim 1, wherein the fluorescein component comprises fluorescein or the pharmaceutically acceptable salt thereof.

14. The method of claim 13, wherein the pharmaceutically acceptable salt of fluorescein is the sodium salt.

15. The method of claim 1, wherein the composition comprises about 0.40% by weight of the benoxinate component.

16. The method of claim 1, wherein the benoxinate component comprises benoxinate or the pharmaceutically acceptable salt thereof.

17. The method of claim 16, wherein the pharmaceutically acceptable salt of benoxinate is the hydrochloride salt.

18. The method of claim 1, wherein the composition further comprises one or more inactive agents selected from boric acid, povidone, purified water, and hydrochloric acid.

19. The method of claim 1, wherein the composition further comprises a preservative.

20. The method of claim 19 wherein the preservative is chlorobutanol or any other suitable ophthalmic preservative.

21. The method of claim 1, wherein the ophthalmic procedure is a conjunctival procedure, a corneal procedure, a tear fluid dynamics evaluation, or a gonioscopy.

22. The method of claim 1, wherein the procedure is tonometry.

23. The method of claim 1, wherein the anesthetizing is corneal anesthesis.

* * * * *